US009567647B2

(12) United States Patent
Ishikawa

(10) Patent No.: US 9,567,647 B2
(45) Date of Patent: Feb. 14, 2017

(54) **PRIMER AND PROBE FOR DETECTION OF *MYCOBACTERIUM AVIUM* AND METHOD FOR DETECTION OF *MYCOBACTERIUM AVIUM* BY USING THE PRIMER OR PROBE**

(75) Inventor: Tomokazu Ishikawa, Hyogo (JP)

(73) Assignee: WAKO PURE CHEMICAL INDUSTRIES, LTD., Osaka (JP)

( * ) Notice: Subject to any disclaimer, the term of this patent is extended or adjusted under 35 U.S.C. 154(b) by 579 days.

(21) Appl. No.: 12/519,141

(22) PCT Filed: Nov. 16, 2007

(86) PCT No.: PCT/JP2007/072324

§ 371 (c)(1),
(2), (4) Date: Jun. 12, 2009

(87) PCT Pub. No.: WO2008/075520

PCT Pub. Date: Jun. 26, 2008

(65) Prior Publication Data

US 2010/0291555 A1 Nov. 18, 2010

(30) Foreign Application Priority Data

Dec. 18, 2006 (JP) ................................ 2006-339884
Dec. 28, 2006 (JP) ................................ 2006-356189

(51) Int. Cl.
*C12Q 1/68* (2006.01)

(52) U.S. Cl.
CPC ........... *C12Q 1/689* (2013.01); *G01N 2333/35* (2013.01)

(58) Field of Classification Search
None
See application file for complete search history.

(56) References Cited

U.S. PATENT DOCUMENTS

| | | | | |
|---|---|---|---|---|
| 5,681,705 | A | 10/1997 | Schram et al. | |
| 5,691,143 | A | 11/1997 | Bustos et al. | |
| 6,465,638 | B2 | 10/2002 | Gorman et al. | |
| 2001/0019822 | A1 | 9/2001 | Gorman et al. | |
| 2001/0053519 | A1* | 12/2001 | Fodor et al. | 435/6 |
| 2004/0029129 | A1* | 2/2004 | Wang | C07K 14/195 435/6.18 |
| 2006/0088833 | A1 | 4/2006 | Bange et al. | |

FOREIGN PATENT DOCUMENTS

| | | | |
|---|---|---|---|
| EP | 0792937 | A2 | 9/1997 |
| EP | 1223225 | A1 | 7/2002 |
| EP | 1 881 068 | A1 | 1/2008 |
| JP | 10-4984 | | 1/1998 |
| JP | 11-69999 | | 3/1999 |
| JP | 3111213 | | 9/2000 |
| JP | 2001-103986 | | 4/2001 |
| JP | 2005-204582 | | 8/2005 |
| WO | WO 03/085129 | A1 | 10/2003 |
| WO | WO 2006/121134 | A1 | 11/2006 |

OTHER PUBLICATIONS

NEB catalog (1998/1999), pp. 121, 284.*
Paustian et al. (Journal of Bacteriology, Apr. 2005, p. 2406-2415).*
*Mycobacterium avium* subsp. paratuberculosis str. k10, complete genome (GenBank AE016958.1, Dec. 29, 2005, 1973 pages; obtained from http://www.ncbi.nlm.nih.gov/nuccore/41400296?sat=13&satkey=7195600 on Sep. 27, 2011.*
Avaniss-Aghajani et al. (Journal of Clinical Microbiology, Jan. 1996, p. 98-102).*
Rothstein et al. (PNAS USA, vol. 91, p. 4155-4159, May 1994).*
International Preliminary Report on Patentability and Written Opinion of the International Searching Authority for International Application No. PCT/JP2007/072324, mailed Jul. 2, 2009, 8 pages.
Database DDBJ/EMBL/GenBank [online] Accession No. CP000479, http://www.ncbi.nlm.nih.gov/entrez/viewer.fcgi?db=nuccore&id=118163506, Dec. 12, 2006 uploaded, Fleischmann R.D., et al., Definition: *Mycobacterium Avium* 104, complete genome.
Supplementary European Search Report (Art. 153(7) EPC), and European Search Opinion from the European Patent Office for International Application No. PCT/JP2007/072324, mailed Dec. 16, 2009, 14 pages.
Poly, F. et al., "Identification of Campylobacter jejuni ATCC 43431-Specific Genes by Whole Microbial Genome Comparisons," Journal of Bacteriology, vol. 186, No. 14, pp. 4781-4795, (Jul. 2004).
Chen, Z.-H. et al, "Identification and Differentiation of *Mycobacterium avium* and M. intracellulare by PCR," Journal of Clinical Microbiology, vol. 34, No. 5, pp. 1267-1269, (May 1996).
Sritharan, V. et al., "Specificity of Diagnostic PCR Amplification for *M. avium* Using the Probe pMAV22," Molecular and Cellular Probes, vol. 9, No. 1, pp. 71-74, (1995).
Frothingham, R. et al., "Sequence-Based Differentiation of Strains in *Mycobacterium avium* Complex," Journal of Bacteriology, vol. 175, No. 10, pp. 2818-2825, (May 1993).
Partial European Search Report (R. 64 EPC) from the European Patent Office for European Application No. 11168275.3, mailed Sep. 15, 2011, 8 pages.

* cited by examiner

*Primary Examiner* — Juliet Switzer
(74) *Attorney, Agent, or Firm* — Finnegan, Henderson, Farabow, Garrett & Dunner LLP

(57) ABSTRACT

The object of the present invention is to provide a novel primer for use in the detection of *Mycobacterium avium* (*M. avium*), and a method for detection of *M. avium* conveniently, rapidly and with high precision by using the primer. More specifically, disclosed are an oligonucleotide which comprises a part or an entire of the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, or a part or an entire of the sequence complementary to the nucleotide sequence, and which is capable of hybridizing with the nucleotide sequence for a *Mycobacterium avium* gene; a primer and a probe for use in the detection of *M. avium*, which comprises the oligonucleotide; and a method for detection of *M. avium* using the primer and/or probe.

15 Claims, 4 Drawing Sheets

Copy number of genome

PRIMER AND PROBE FOR DETECTION OF *MYCOBACTERIUM AVIUM* AND METHOD FOR DETECTION OF *MYCOBACTERIUM AVIUM* BY USING THE PRIMER OR PROBE

RELATED APPLICATIONS

This application is a national phase filing of International Application No. PCT/JP2007/072324, filed on Nov. 16, 2007, which claims priority from Japanese Patent Application No. 2006-339884, filed Dec. 18, 2006, and Japanese Patent Application No. 2006-356189, filed Dec. 28, 2006. Each of these applications are incorporated herein by reference for all purposes.

TECHNICAL FIELD

The present invention relates to a method for detection and/or identification of *Mycobacterium avium* (hereinafter, described as *M. avium*) in clinical laboratory testing through the use of nucleic acid amplification and detection system.

BACKGROUND ART

Nontuberculous *mycobacterium* is a gram positive *bacillus* having acid-fast characteristics classified into genus *Mycobacterium* (hereinafter, optionally abbreviated simply as M.), and is a kind of acid-fast bacterium other than tuberculosis complex and *Mycobacterium leprae*. Fifteen to 20% of cases showing positive for sputum smear examination for acid-fast bacterium have been diagnosed to be nontuberculous *mycobacterium* by subsequent examinations for identification of bacterial strain.

Among nontuberculous mycobacteria, clinically problematic known bacterial strain includes *M. avium*, *Mycobacterium intracellulare* (hereinafter, abbreviated as "*M. intracellulare*"), *Mycobacterium kansasii*, *Mycobacterium marinum*, *Mycobacterium gordonae*, *Mycobacterium szulgai*, *Mycobacterium xenopi*, *Mycobacterium fortuitum*, *Mycobacterium chelonei*, *Mycobacterium abscessus*, and so on.

Above all, the commonly noted strains are *M. avium* and *M. intracellulare*. Since *M. avium* and *M. intracellulare* are closely resemble each other and difficult to distinguish between them, *M. intracellulare* and *M. avium* have been referred to collectively as *Mycobacterium avium* complex (MAC). About 70% of patients with nontuberculous mycobacteria disease are MAC infection, and the second large population is *M. kansasii* infection accounting 20%. And the rest of 10% are the infection by other bacterial strains.

In general, the nontuberculous mycobacteria have weak toxicity, and they are believed to be harmless to a healthy subject. However, on rare occasions, they may exert infectivity to human. Among them, the MAC is known to cause sometimes aftereffects of tuberculosis (lung infectious disease), or to cause opportunistic infections to a compromised patient such as AIDS patient. Therefore, it is particularly important in the therapy to detect the nontuberculous mycobacteria with rapidity and preciseness.

In addition, in recent years, the incidence of nontuberculous *mycobacterium* infection demonstrates upward trend, and therefore, development of a method for discriminating tuberculosis bacterium from nontuberculous mycobacteria in a short period of time has been desired strongly. Moreover, from the viewpoint of the fact that the method of detecting/diagnosing *M. avium* and *M. intracellulare* by nucleic acid amplification technology has been included in health insurance coverage, its diagnostic significance is obviously great.

In addition, most of the nontuberculous mycobacteria demonstrate resistance against antituberucular agents. Therefore, when a patient is suspected of acid-fast bacterium infection, differential diagnosis whether the disease is tuberculosis or nontuberculous *mycobacterium* disease is quite important to decide a course of treatment. Further, as a method for treatment of the diseases caused by nontuberculous mycobacteria may vary depending on the individual species of bacterium, the identification of bacterial strain is also quite important. However, nontuberculous *mycobacterium* diseases do not show any specific clinical symptom. Therefore, it is quite difficult to differentiate tuberculosis from nontuberculous *mycobacterium* disease by clinical observation and histopathological manifestation, and to specify the species of the nontuberculous *mycobacterium*. Consequently, the diagnosis whether the disease is tuberculosis or nontuberculous *mycobacterium* disease has to be determined by bacterial identification of the infected bacterium.

A typical method for identification of bacterium to be carried out for the diagnosis of nontuberculous *mycobacterium* disease is sputum smear examination. However, by this test, what can be figured out is only whether the pathogenic bacterium is "positive for acid-fast bacterium" or not and whether the pathogenic bacterium is tuberculosis bacterium or nontuberculous *mycobacterium* cannot be differentiated. Therefore, when the result of the sputum smear examination is positive, bacterial culture examination by isolation culture on a culture medium such as Ogawa's medium has to be carried out to differentiate between tuberculosis bacterium and nontuberculous *mycobacterium*. And further, by performing additional biochemical examinations, bacterial species of the infected bacterium is identified. However, in general, growth of bacterium belonging to genus *Mycobacterium* is slow; for example, it takes 3 to 4 weeks only for its isolation culture. And further, it requires additional 2 to 3 weeks to obtain the results of various biochemical tests for the identification of bacterial species. Accordingly, the conventional basic method, in which a diagnostic outcome on whether the disease is tuberculosis or not is obtained by conducting the above described smear examination and a cell culture examination, is a considerably time-consuming method.

On the other hand, in recent years, a technology of detecting bacteria on a genetic level has been developed. For example, a diagnostic technique utilizing the nucleic acid amplification technology such as polymerase chain reaction (PCR) and the like has been studied as a useful means for detecting bacteria. Because of high sensitivity of this method, even if there are only several cells of the bacteria in a sample, the bacteria can be detected. In addition, this method has an advantage that the detection (identification of bacterial species) can be completed in a short time (in 4 days at the longest). However, in the usual PCR method, the number of bacterial count cannot be determined. In addition, in this method, cells are detected regardless of live cells or dead cells. Further, if some bacteria exist in the sample, the determination is made positive regardless of size of the bacterial count. Therefore, by the PCR method, diagnosis on whether the bacteria detected in a patient are infectious or not will be uncertain. Furthermore, the method has a problem such as providing a frequent false positive judgment due to its too high sensitivity.

With respect to the method for detection of *M. avium* using the PCR method, there is a method for detection of MAC nucleic acid using a multiple primer set of oligonucleotide primers specific for 2 or more of gene regions comprising, for example, MacSequevar gene region, 19 kD protein (MAV 19k) gene region of *M. avium*, and ribosomal protein s1 gene region of *M. intracellulare* (Patent Literature 1). However, by this method, discrimination between *M. avium* and *M. intracellulare* cannot be achieved. In addition, the Patent Literature 1 has also disclosed an Msqv-Av probe which is a primer capable of detecting only *M. avium*, and an MAV 19K primer specific for nucleic acid from *M. avium*. However, even by the detection method using these probe and primer, there also disclosed some cases where *M. avium* can not be identified clearly as *M. avium* depending on the type of strain. That is, the specificity of these probe and primer for *M. avium* is far from satisfactory.

In addition, a method in which PCR is carried out by using a primer capable of amplifying a DNA nucleotide sequence nipping insertion site of the gene insertion sequence IS901, and by determining whether it is avian tuberculosis bacterium (*M. avium*) or *M. intracellulare* based on the chain length of obtained primer extension product (Patent Literature 2) has also been known. However, in the PCR using aforementioned primer, the primer extension product can be obtained in either the case where the sample is avian tuberculosis bacterium (*M. avium*) and the case of *M. intracellulare*, and therefore, this determination method can not be said as a specific method for *M. avium*. In addition, the method, whereby the discrimination between both bacterial strains is carried out based on the chain length of the primer extension product is cumbersome; and it is conceivable that different determination may be made by different judge; and in consequence, it cannot be said that the method is a reliable determination method.

Other than the PCR method, there is a determination method through the use of Strand Displacement Amplification Method (SDA method). For example, JP-A-H10-4984 (Patent Literature 3) discloses a method in which 63 nucleotide segment of BCG85-B gene coding a part of α-antigen of *mycobacterium* is targeted. In this method, using a primer which is capable of amplifying the target sequence in the BCG85-B gene owned by both *M. avium* and *M. intracellulare*, nucleic acid amplification reaction is carried out by the SDA method. And then, MAC is detected based on the results. That is, the primer used in aforementioned method is a primer capable of amplifying both *M. avium* and *M. intracellulare*. However, in this method, as a matter of course, a primer extension product will be obtained in both cases where either of *M. avium* or *M. intracellulare* exists in a sample. Because of that, MAC can be detected by this method; however, it is impossible to detect *M. avium* specifically. In addition, even when MAC is detected, there can be an instance where false-positive result is provided.

In JP-A-2001-103986 (Patent Literature 4), primers to be used for the detection of MAC, oligonucleotides to be used as a capture probe and a detection probe have been disclosed. However, aforementioned primer can amplify a 48 bp target sequence of dnaJ gene which is owned commonly by both avian tuberculosis bacteria (*M. avium*) and *M. intracellulare*. Namely, amplification reaction will take place in both cases where either of *M. avium* or *M. intracellulare* is present in a sample. Therefore, if the SDA method is practiced using aforementioned primer, the primer extension product will be detected using the capture probe and detection probe, and based on the results, detection of MAC can be achieved. However, specific detection of *M. avium* is impossible to achieve without detection of *M. intracellulare*.

Beyond that, there is a method of amplification of nucleic acid from *M. avium* through the use of LAMP (Loop-Mediated Isothermal Amplification) method, and the like. However, in the LAMP method, there are some problems, for example, the nucleotide sequence of amplified DNA cannot be determined; efficient length of DNA to be amplified is limited; and the method provides false-positive result occasionally.

In addition, there exist plural numbers of serotypes such as, for example, serotypes 4 to 6, 8 to 11 and 21 for *M. avium*, and serotypes 7, 12 to 20 and 25 for *M. intracellulare*. Therefore, it is difficult to find out a consensus sequence between strains. In consequence, it is difficult to detect all the *M. avium* having various serotypes by PCR using single primer set. This is the present situation in this field.

As described above, in such the situation, it has been desired to establish a method which enables to detect *M. avium* specifically and rapidly.

Patent Literature 1: JP-A-H11-69999
Patent Literature 2: JP-B-3111213
Patent Literature 3: JP-A-H10-4984
Patent Literature 4: JP-A-2001-103986
Patent Literature 5: JP-A-2005-204582
Non-Patent Literature 1: F. Poly et al., J. Bacteriology, 2004, 186(14), p. 4781-4795.

DISCLOSURE OF THE INVENTION

Problems to be Solved by the Invention

The present invention was made in view of the above described situation, and an object of the present invention is to provide a new primer for detection of *M. avium* which can exclude any false-positive result for the diagnosis, and a method with the use of the primer for detection of *M. avium* more conveniently, rapidly and with high precision. Further, another object of the present invention is to provide a new primer for detection of *M. avium* which can detect specifically and efficiently plural number of *M. avium* with various serotypes by single measurement, and a method with the use of it for detection of *M. avium* more conveniently, rapidly and with high precision.

The present invention was made for the purpose of solving the above described problems, and comprises the following composition.
(1) An oligonucleotide which comprises a part or an entire of the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136 (wherein, the characters of A, C, G and T represent adenine, cytosine, guanine and thymine, respectively; and T at an arbitrary position may be replaced by uracil (U); and hereinafter, same as above), or a part or an entire of the sequence complementary to the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, and which is capable of hybridizing with the nucleotide sequence for a *Mycobacterium avium* gene.

(2) A primer for detection of *Mycobacterium avium* comprising an oligonucleotide which comprises a part or an entire of the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO: 134, SEQ ID NO:135, and SEQ ID NO:136, or a part or an entire of the sequence complementary to the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, and which is capable of hybridizing with the nucleotide sequence for a *Mycobacterium avium* gene.

(3) A probe for detection of *Mycobacterium avium* comprising an oligonucleotide which comprises a part or an entire of the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, or a part or an entire of the sequence complementary to the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, and which is capable of hybridizing with the nucleotide sequence for a *Mycobacterium avium* gene.

(4) The detection method according to claim 13, characterized in that the nucleic acid amplification reaction is carried out using as a primer an oligonucleotide which comprises a part or an entire of the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, or a part or an entire of the sequence complementary to the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, and which is capable of hybridizing with the nucleotide sequence for a *Mycobacterium avium* gene, and using nucleic acid in a sample as a template, and the obtained primer extension product is detected.

(5) A reagent kit for detection of *Mycobacterium avium* comprising an oligonucleotide which comprises a part or an entire of the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, or a part or an entire of the sequence complementary to the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, and which is capable of hybridizing with the nucleotide sequence for a *Mycobacterium avium* gene, as a primer and/or a probe.

With respect to the various types of genes from *M. avium* and other living organisms which the nucleotide sequence have been determined up to today, the present inventor has conducted theoretical verification and experimental verification of sequence homology present interspecies. As a result, the present inventor has found the presence of a nucleotide sequence in the fragments of nucleotide sequence derived from *M. avium* obtained by a method using microarray technique, which is capable of hybridizing specifically with the nucleotide sequence of *M. avium* and is useful for detection of *M. avium*.

And so, on the basis of these findings, the present inventor further studied intensively and obtained oligonucleotides specific for *M. avium* (the nucleotide sequence shown in SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136), and has found that these nucleotide sequences are useful for detection of *M. avium*. And further, on the basis of these sequences, a primer and a probe for the detection of *M. avium* have been developed, and thus a method for detection of *M. avium* using these primer and probe has been established.

Effect of the Invention

According to the method for detection of *M. avium* using the primer and/or probe of the present invention, *M. avium* can be detect and diagnosed more rapidly and with high precision as compared to the conventional bacterium identification method by bacterial cell culture examination and the like. In addition, by performing the detection using the method of the present invention, any false-positive result in diagnosis can be eliminated as compared with the diagnostic method by the PCR using a conventional primer and/or a probe, and as the results, *M. avium* can be detected and diagnosed with higher accuracy and preciseness in a specific manner. In addition, by the use of the detection method of the present invention, *M. avium* cell can also be quantified.

In addition, according to the method for detection of *M. avium* using the primer and/or probe which comprises a sequence derived from the sequence shown in SEQ ID NO:130 to 136 of the present invention, namely the sequence shown in SEQ ID NO:130 to 205, the plural number of *M. avium* with various serotypes can be detected specifically and efficiently in distinction from other *Mycobacterium* genus by a single measurement. In addition, this may make detection procedure simple and also may provide such a beneficial effect that the time necessary for the diagnosis will be reduced.

EXPLANATION OF LETTERS OR NUMERALS

Figure 3:
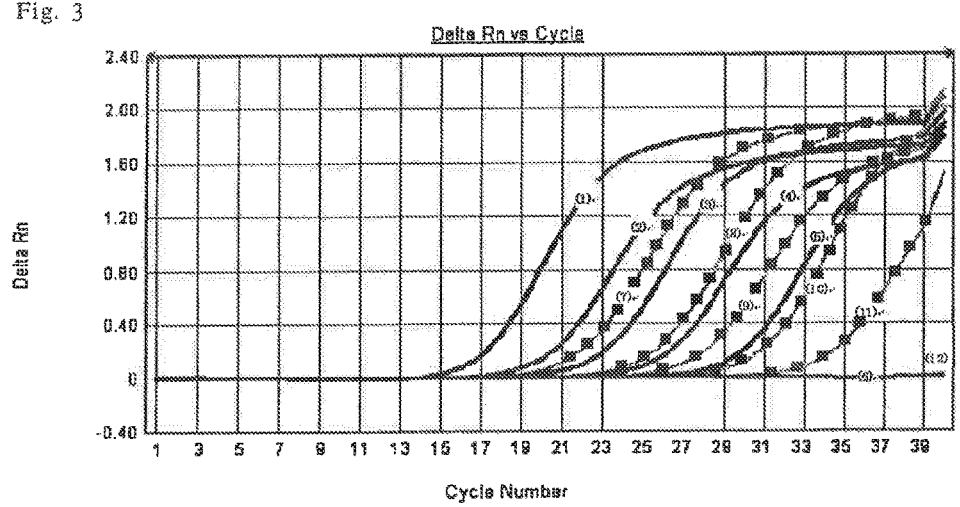
FIG. 3 shows an amplification curve obtained on the basis of the result of the real-time PCR by intercalator method obtained in Example 6 using primer 12Fw_1 and primer 12Rv_1 and using genomic DNA sample derived from *M. avium* as a template, and the amplification curve obtained on the basis of the result of the real-time PCR by intercalator method obtained in Comparative Example 1 using primer MAV19K_Fls and primer MAV19K_Rvs and using genomic DNA sample from *M. avium* as a template.

In FIG. 3, each symbols shows the result of the following cases, respectively.
(1) A case where the real-time PCR was carried out at a target of novel candidate sequence 13 at initial DNA concentration of $10^5$ copies in the DNA sample for PCR.
(2) A case where the real-time PCR was carried out at a target of novel candidate sequence 13 at initial DNA concentration of $10^4$ copies in the DNA sample for PCR.
(3) A case where the real-time PCR was carried out at a target of novel candidate sequence 13 at initial DNA concentration of $10^3$ copies in the DNA sample for PCR.
(4) A case where the real-time PCR was carried out at a target of novel candidate sequence 13 at initial DNA concentration of $10^2$ copies in the DNA sample for PCR.
(5) A case where the real-time PCR was carried out at a target of novel candidate sequence 13 at initial DNA concentration of 10 copies in the DNA sample for PCR.
(6) A case where the real-time PCR was carried out at a target of novel candidate sequence 13 at initial DNA concentration of 0 copies in the DNA sample for PCR.

In FIG. 3, (7) to (12) shows the following cases.
(7) A case where the real-time PCR was carried out at a target of a gene region for 19 kilo-Dalton protein of *M. avium* at initial DNA concentration of $10^5$ copies in the DNA sample for PCR.
(8) A case where the real-time PCR was carried out at a target of a gene region for 19 kilo-Dalton protein of *M. avium* at initial DNA concentration of $10^4$ copies in the DNA sample for PCR.
(9) A case where the real-time PCR was carried out at a target of a gene region for 19 kilo-Dalton protein of *M. avium* at initial DNA concentration of $10^3$ copies in the DNA sample for PCR.
(10) A case where the real-time PCR was carried out at a target of a gene region for 19 kilo-Dalton protein of *M. avium* at initial DNA concentration of $10^2$ copies in the DNA sample for PCR.
(11) A case where the real-time PCR was carried out at a target of a gene region for 19 kilo-Dalton protein of *M. avium* at initial DNA concentration of 10 copies in the DNA sample for PCR.
(12) A case where the real-time PCR was carried out at a target of a gene region for 19 kilo-Dalton protein of *M. avium* at initial DNA concentration of 0 copies in the DNA sample for PCR.

BEST MODE FOR CARRYING OUT THE INVENTION

In the present invention, *M. avium* gene refers to an arbitral unit of nucleotide sequence (a region) in the whole genome sequence owned by *Mycobacterium avium*.

The oligonucleotide of the present invention includes an oligonucleotide which comprises a part or an entire of the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136 (wherein, the characters of A, C, G and T represent adenine, cytosine, guanine and thymine, respectively; and T at an arbitrary position may be replaced by uracil (U); and hereinafter, the same as above), or a part or an entire of the sequence complementary to the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, and which is capable of hybridizing with the nucleotide sequence for a *M. avium* gene (hereinafter, optionally described simply as the oligonucleotide of the present invention).

As to size of the oligonucleotides involved in the present invention, an oligonucleotide consisting of a nucleotide sequence shown in SEQ ID NO:1 has 981 nucleotides; an oligonucleotide consisting of a nucleotide sequence shown in SEQ ID NO:2 has 326 nucleotides; an oligonucleotide consisting of a nucleotide sequence shown in SEQ ID NO:3 has 503 nucleotides; an oligonucleotide consisting of a nucleotide sequence shown in SEQ ID NO:4 has 587 nucleotides; and an oligonucleotide consisting of a nucleotide sequence shown in SEQ ID NO:5 has 622 nucleotides.

In addition, an oligonucleotide consisting of a nucleotide sequence shown in SEQ ID NO:37 has 1020 nucleotides; an oligonucleotide consisting of a nucleotide sequence shown in SEQ ID NO:38 has 959 nucleotides; an oligonucleotide consisting of a nucleotide sequence shown in SEQ ID NO:39 has 896 nucleotides; an oligonucleotide consisting of a nucleotide sequence shown in SEQ ID NO:40 has 744 nucleotides; and an oligonucleotide consisting of a nucleotide sequence shown in SEQ ID NO:41 has 790 nucleotides; and an oligonucleotide consisting of a nucleotide sequence shown in SEQ ID NO:42 has 569 nucleotides.

In addition, an oligonucleotide consisting of a nucleotide sequence shown in SEQ ID NO:130 has 833 nucleotides; an oligonucleotide consisting of a nucleotide sequence shown in SEQ ID NO:131 has 955 nucleotides; an oligonucleotide consisting of a nucleotide sequence shown in SEQ ID NO:132 has 810 nucleotides; an oligonucleotide consisting of a nucleotide sequence shown in SEQ ID NO:133 has 872 nucleotides; and an oligonucleotide consisting of a nucleotide sequence shown in SEQ ID NO:134 has 933 nucleotides; an oligonucleotide consisting of a nucleotide sequence shown in SEQ ID NO:135 has 630 nucleotides; and an oligonucleotide consisting of a nucleotide sequence shown in SEQ ID NO:136 has 1085 nucleotides.

An oligonucleotide involved in the present invention which comprises a part or an entire of the nucleotide sequences selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136 includes, for example, (1) an oligonucleotide comprising a nucleotide sequence having a sequence homology of not less than 70%, preferably not less than 80%, more preferably not less than 90%, further more preferably not less than 95% to the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, or (2) an oligonucleotide characterized by comprising more than 10 consecutive nucleotides, preferably more than 15 consecutive nucleotides, more preferably more than 20 consecutive nucleotides in the sequences selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, or the like.

Specific examples of oligonucleotide involved in the present invention which comprises an entire of the nucleotide sequences selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136 includes, for example, the oligonucleotides which consist of the nucleotide sequences selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, or the oligonucleotides which comprise the nucleotide sequences selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136.

Preferably, the oligonucleotide consisting of nucleotide sequence selected from SEQ ID NO:130 to 136, or the oligonucleotide comprising nucleotide sequence selected from SEQ ID NO:130 to 136 is included.

Preferable examples of oligonucleotides which comprises a part of the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136 include the oligonucleotide which comprises a part of nucleotide sequence selected from SEQ ID NO:130 to 136.

Specific examples of oligonucleotide which comprises a part of the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136 include, for example, the oligonucleotide which comprises a part or an entire of nucleotide sequence selected from SEQ ID NO:6 to 32, SEQ ID NO:43 to 129, and SEQ ID NO:137 to 205.

Preferably, the one which comprises a part or an entire of nucleotide sequence selected from SEQ ID NO:137 to 205 is included.

In addition, oligonucleotides which comprise more than 10 consecutive nucleotides, preferably more than 15 consecutive nucleotides in the nucleotide sequence selected from SEQ ID NO:6 to 32, SEQ ID NO:43 to 129, and SEQ ID NO:137 to 205 are preferable.

Specific examples of oligonucleotide which comprises an entire of the nucleotide sequence selected from SEQ ID NO:6 to 32, SEQ ID NO:43 to 129, and SEQ ID NO:137 to 205 include oligonucleotides consisting of a nucleotide sequence selected from SEQ ID NO:6 to 32, SEQ ID NO:43 to 129, and SEQ ID NO:137 to 205, or oligonucleotides comprising a nucleotide sequence selected from SEQ ID NO:6 to 32, SEQ ID NO:43 to 129, and SEQ ID NO:137 to 205.

A specific preferable example includes an oligonucleotide consisting of a nucleotide sequence selected from SEQ ID NO:137 to 205, or an oligonucleotide comprising a nucleotide sequence selected from SEQ ID NO:137 to 205.

A specific example of an oligonucleotide comprising a part of the nucleotide sequence shown in SEQ ID NO:1 includes, for example, the one which comprises a sequence selected from SEQ ID NO:6 to 9 and SEQ ID NO:24 to 25.

A specific example of an oligonucleotide comprising a part of the nucleotide sequence shown in SEQ ID NO:2 includes, for example, the one which comprises a sequence selected from SEQ ID NO:10 to 11 and SEQ ID NO:26.

A specific example of an oligonucleotide comprising a part of the nucleotide sequence shown in SEQ ID NO:3 includes, for example, the one which comprises a sequence selected from SEQ ID NO:12 to 13 and SEQ ID NO:27.

A specific example of an oligonucleotide comprising a part of the nucleotide sequence shown in SEQ ID NO:4 includes, for example, the one which comprises a sequence selected from SEQ ID NO:14 to 21 and SEQ ID NO:28 to 31.

A specific example of an oligonucleotide comprising a part of the nucleotide sequence shown in SEQ ID NO:5 includes, for example, the one which comprises a sequence selected from SEQ ID NO:22 to 23 and SEQ ID NO:32.

A specific example of an oligonucleotide comprising a part of the nucleotide sequence shown in SEQ ID NO:37 includes, for example, the one which comprises a sequence selected from SEQ ID NO:43 to 54 and SEQ ID NO:101 to 106.

A specific example of an oligonucleotide comprising a part of the nucleotide sequence shown in SEQ ID NO:38 includes the one which comprises a sequence selected from SEQ ID NO:55 to 66 and SEQ ID NO:107 to 112.

A specific example of an oligonucleotide comprising a part of the nucleotide sequence shown in SEQ ID NO:39 includes, for example, the one which comprises a sequence selected from SEQ ID NO:67 to 74 and SEQ ID NO:113 to 116.

A specific example of an oligonucleotide comprising a part of the nucleotide sequence shown in SEQ ID NO:40 includes, for example, the one which comprises a sequence selected from SEQ ID NO:75 to 82 and SEQ ID NO:117 to 120.

A specific example of an oligonucleotide comprising a part of the nucleotide sequence shown in SEQ ID NO:41 includes, for example, the one which comprises a sequence selected from SEQ ID NO:83 to 92 and SEQ ID NO:121 to 125.

A specific example of an oligonucleotide comprising a part of the nucleotide sequence shown in SEQ ID NO:42 includes, for example, the one which comprises a sequence selected from SEQ ID NO:93 to 100 and SEQ ID NO:126 to 129.

A specific example of an oligonucleotide comprising a part of the nucleotide sequence shown in SEQ ID NO:130 includes, for example, the one which comprises a sequence selected from SEQ ID NO:137 to 144 and SEQ ID NO:183 to 186.

A specific example of an oligonucleotide comprising a part of the nucleotide sequence shown in SEQ ID NO:131 includes, for example, the one which comprises a sequence selected from SEQ ID NO:145 to 148 and SEQ ID NO:187 to 188.

A specific example of an oligonucleotide comprising a part of the nucleotide sequence shown in SEQ ID NO:132 includes, for example, the one which comprises a sequence selected from SEQ ID NO:149 to 158 and SEQ ID NO:189 to 193.

A specific example of an oligonucleotide comprising a part of the nucleotide sequence shown in SEQ ID NO:133 includes, for example, the one which comprises a sequence selected from SEQ ID NO:159 to 164 and SEQ ID NO:194 to 196.

A specific example of an oligonucleotide comprising a part of the nucleotide sequence shown in SEQ ID NO:134 includes, for example, the one which comprises a sequence selected from SEQ ID NO:165 to 170 and SEQ ID NO:197 to 199.

A specific example of an oligonucleotide comprising a part of the nucleotide sequence shown in SEQ ID NO:135 includes, for example, the one which comprises a sequence selected from SEQ ID NO:171 to 174 and SEQ ID NO:200 to 201.

A specific example of an oligonucleotide comprising a part of the nucleotide sequence shown in SEQ ID NO:136 includes, for example, the one which comprises a sequence selected from SEQ ID NO:175 to 182 and SEQ ID NO:202 to 205.

An oligonucleotide involved in the present invention which comprises a part or an entire of the sequence complementary to the nucleotide sequences selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136 includes, for example, an oligonucleotide comprising a part or an entire of the nucleotide sequence which is capable of hybridizing with an oligonucleotide consisting of a nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136 of the present invention, and the like.

The above-described oligonucleotide having a part or an entire of the nucleotide sequence which is capable of hybridizing with an oligonucleotide consisting of the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136 of the present invention includes, in particular, an oligonucleotide comprising a part or an entire of the nucleotide sequence which is capable of hybridizing under high stringent condition or stringent condition with an oligonucleotide consisting of the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136 of the present invention, and the like.

It should be noted that, the phrase of "high stringent condition" used herein is, specifically, for example, "the condition where hybridization is carried out in 50% formamide at 42 to 70° C., preferably 60 to 70° C., and followed by washing with 0.2 to 2×SSC containing 0.1% sodium dodecyl sulfate (SDS) at 25 to 70° C.".

In addition, the phrase of "stringent condition" is, specifically, for example, "the condition where hybridization is carried out in 6×SSC or a hybridization solution with equivalent salt concentration at the temperature of 50 to 70° C. for 16 hours, and then, if needed, followed by pre-washing with 6×SSC or a solution with the equivalent salt concentration, and followed by washing with 1×SSC or a solution with the equivalent salt concentration and the like".

An oligonucleotide comprising a part or an entire of the sequence complementary to the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136 involved in the present invention includes, for example, (1) an oligonucleotide comprising a nucleotide sequence having a sequence homology of not less than 70%, preferably not less than 80%, more preferably not less than 90%, yet further preferably not less than 95% to the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, or (2) an oligonucleotide characterized by comprising not less than 10 consecutive nucleotides, preferably not less than 15 nucleotides, more preferably not less than 20 nucleotides in the sequence complementary to the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, and the like.

A specific example of the oligonucleotide comprising an entire of the sequence complementary to the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136 involved in the present invention includes, for example, an oligonucleotide consisting of the sequence complementary to the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, or an oligonucleotide which comprises the sequence complementary to the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136.

Preferably, an oligonucleotide consisting of the sequence complementary to the nucleotide sequence selected from SEQ ID NO:130 to 136, or an oligonucleotide which comprises the sequence complementary to the nucleotide sequence selected from SEQ ID NO:130 to 136 is included.

A preferable example of the oligonucleotide comprising a part of the sequence complementary to the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136 includes an oligonucleotide which comprises a part of the sequence complementary to the nucleotide sequence selected from SEQ ID NO:130 to 136.

A specific example of the oligonucleotide which comprises a part of the sequence complementary to the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136 includes, for example, an oligonucleotide comprising a part or an entire of the sequence complementary to the nucleotide sequence selected from SEQ ID NO:6 to 32, SEQ ID NO:43 to 129, and SEQ ID NO:137 to 205.

Preferably, an oligonucleotide which comprises a part or an entire of the sequence complementary to the nucleotide sequence selected from SEQ ID NO:137 to 205 is included.

In addition, an oligonucleotide which comprises not less than 10 consecutive nucleotides, preferably not less than 15 nucleotides in the sequence complementary to the nucleotide sequence selected from SEQ ID NO:6 to 32, SEQ ID NO:43 to 129, and SEQ ID NO:137 to 205, is preferable.

A specific example of the oligonucleotide which comprises an entire of the sequence complementary to the nucleotide sequence selected from SEQ ID NO:6 to 32, SEQ ID NO:43 to 129, and SEQ ID NO:137 to 205 includes, for example, an oligonucleotide consisting of a sequence complementary to the nucleotide sequence selected from SEQ ID NO:6 to 32, SEQ ID NO:43 to 129, and SEQ ID NO:137 to 205, or an oligonucleotide which comprises a sequence complementary to the nucleotide sequence selected from SEQ ID NO:6 to 32, SEQ ID NO:43 to 129, and SEQ ID NO:137 to 205.

A specific preferable example thereof includes an oligonucleotide consisting of a sequence complementary to the nucleotide sequence selected from SEQ ID NO:137 to 205, or an oligonucleotide which comprises a sequence complementary to the nucleotide sequence selected from SEQ ID NO:137 to 205.

The oligonucleotide which is capable of hybridizing with the nucleotide sequence of *M. avium* gene involved in the present invention includes an oligonucleotide having a nucleotide sequence capable of hybridizing with the nucleotide sequence of *M. avium* gene under the high stringent condition or the stringent condition, and the like. The high stringent condition and the stringent condition are as described above.

It should be noted that, the oligonucleotide of the present invention may be either deoxyribonucleic acid (DNA) or ribonucleic acid (RNA). In the case of ribonucleic acid, it goes without saying that thymidine residue (T) may be read as uridine (U) residue. In addition, it may be a DNA comprising uridine residue which is synthesized by exchanging T at an arbitrary position by U. Also, it may be an RNA comprising thymidine residue which is synthesized by exchanging U at an arbitrary position by T. In addition, it may be an oligonucleotide having deletion, insertion or replacement of one or plural nucleotides. One or plural nucleotides may be a modified nucleotide such as inosine (I).

Method for obtaining the oligonucleotide of the present invention includes, for example, but not limited to, a method for preparation by chemical synthesis, as is well known. In this method, it is possible to obtain an oligonucleotide having consistent quality, easily, in large scale, at low cost, as compared to the method of obtaining an oligonucleotide or a polynucleotide by genetic engineering technique using a vector and the like (cloning method).

For example, by a conventional method of DNA synthesis using a DNA synthesizer, an oligonucleotide is synthesized according to the conventional phosphoramidite method, and then purified through anion exchange column chromatography. Thus, an objective oligonucleotide of the present invention can be obtained.

Alternatively, using vendor's custom service of contract synthesis, the oligonucleotide may be purchased from the vendor.

A means for searching (screening) an oligonucleotide which can attain the purpose of the present invention include the subtraction method as described in FEMS Microbiology Letters 166: 63-70, 1998 or Systematic and Applied Microbiology 24; 109-112, 2001, which is a methodology of concentrating a candidate sequence by subtracting a nucleotide sequence which reacts with a fragment of genomic DNA derived from a species to be differentiated from a group of fragments derived from the target genomic DNA.

In addition, an approach in which differential display of amplification products from a target genomic DNA and a genomic DNA derived from species to be differentiated are prepared, that is, a methodology through the use of the arbitrarily primed polymerase chain reaction (AP-PCR) (JP-A-H11-155589) can be considered.

Further, through the use of so called microarray method, search for an oligonucleotide which can attain the purpose of the present invention can be carried out, and also the oligonucleotide of the present invention can be obtained. The brief description of the method is as follows:

Namely, for example, a shotgun clone of genomic DNA derived from M. avium is prepared, and then the DNA is purified from the obtained shotgun clone. After that, the purified DNA derived from shotgun clone is amplified by PCR and the like, and the amplified DNA is arranged on a slide glass by common procedure to prepare a microarray. In addition, a group of fluorescent labeled genomic DNA fragments (Label-1) is prepared from the genomic DNA of target *M. avium*. On the other hand, a group of fluorescent labeled DNA fragments (Label-2) is prepared separately from the genomic DNA derived from species to be differentiated. And, by performing competitive hybridization method using the Label-1 and the Label-2 in the same reaction system, the reactivity (binding potency) of the purified DNA on a microarray with each Label-1 and Label-2 is assayed. By this assay, the candidate sequence group which react more specifically with the fragments (Label-1) derived from genomic DNA of the target *M. avium* can be selected (see, for example, Non-Patent Literature 1, and so on).

By the method described above, an objective oligonucleotide which is capable of hybridizing specifically with a nucleotide sequence for a *M. avium* gene can be selected. An example of the method for selection of the oligonucleotide of the present invention using the microarray method will be described in detail as follows:

(1) Preparation of Purified Genomic DNA Derived from *M. Avium*

At first, purified genomic DNA derived from *M. avium* is obtained. For example, the genomic DNA derived from *M. avium* may be obtained commercially, or may be obtained by extraction and purification of DNA from *M. avium* strain according to the conventional procedure. Alternatively, using vendor's custom service of contract order for extraction and purification of genomic DNA from *M. avium* strain, the genomic DNA may be obtained from the vendor.

Commercially available purified genomic DNA derived from *M. avium* includes, for example, genomic DNA from *M. avium* (Mycos Research LLC, USA) and the like.

While commercially available purified DNA derived from *M. avium* may be used as it is, the conventional nucleic acid amplification reaction may be carried out for the DNA using a kit on the market and the like, and obtained amplification product may be used.

To obtain the purified genomic DNA from *M. avium* strain, the microbial cell of *M. avium* is subjected to conventional fracturing treatment (for example, the method for pulverization treatment of microbial cell by autoclaving and the use of glass beads and the like), and then extraction and purification of DNA may be carried out according to the conventional procedures.

(2) Preparation of Whole Genome Shotgun Library

As an example of the method for preparing Whole Genome Shotgun Library of *M. avium*, a method modified from the Whole Genome Shotgun method described by Venter et al. in Science, 2001 Feb. 16; 291 (5507): 1304-1351 will be described below.

First, the purified genomic DNA derived from *M. avium* obtained in the above-described (1) is diluted with an appropriate buffer solution and the like, and then shared into fragments, for example, in the presence of 20% final concentration of glycerol, by treating for about 1 to 15 minutes using a nebulizer under a pressure of 5 to 9 kPa. By this treatment, the objective size of 500 to 1,000 bp fractions (DNA fraction) can be recovered efficiently. The fraction obtained is purified using a commercially available extraction column.

After that, according to the common procedures, the obtained fraction (DNA fragments, containing objective DNA fragment) is inserted into a vector DNA by ligation, and thus the recombinant DNA (Whole Genome Shotgun Library of *M. avium*) is obtained.

The vector to be used for this purpose includes, in the case where the host cell for subsequent transformation is *E. coli*, for example, the vectors such as pBS (e.g., pBSII sk$^+$ vector (Stratagene Corp.)), pQE-TRI plasmid (Qiagen GmbH), pBluescript, pET, pGEM-3Z, pGEX and the like. Depending on the kind of vector is used, prior to the ligation, terminal of the DNA fragments may be blunted by treating with DNA polymerase and the like in advance.

After that, using the obtained recombinant DNA, an appropriate host cell is transformed to obtain a transformant.

The host cell to be used for this purpose includes, for example, *Escherichia coli*, preferably JM109, DH5α, TOP10 and so on. In addition to these, competent cells which provide high transfection efficiency for the plasmid and the phage DNA may be used. For example, *E. coli* JM109 Competent Cells (Takara Bio Inc.) and the like are included.

The transformation of the host cell may be carried out, for example, according to D. M. Morrison's method (Method in Enzymology, 68, 326-331, 1979) and the like. In addition, when a commercially available competent cell is used, the transformation may be carried out according to the protocol provided for the product.

A method for selection of the transformant which has been introduced with "the recombinant DNA having the objective DNA fragment" includes, for example, a method through the use of property of the vector used for the transformation. For example, when a vector comprising ampicillin-resistant gene is used, by culturing the transformant on a medium containing ampicillin and followed by selecting the resulting clone, the transformant which has been transformed by the recombinant DNA having the objective DNA fragment (Whole Genome Shotgun library derived from *M. avium*) can be obtained easily.

(3) Preparation of Microarray

Microarray is prepared by the following method.

Namely, from the transformant Library (Whole Genome Shotgun clone Library derived from genomic DNA of *M. avium*) obtained in the above-described (2), DNA is purified according to the conventional procedures. Using the purified DNA as a template, and using an appropriate primer [it may be a commercially available primer; for example, M13 Primer M1 (Takara Bio Inc.) and M13 Primer RV (Takara Bio Inc.) and the like], the PCR is carried out according to the conventional procedure and the resulting PCR amplification product is purified. After that, according to the conventional procedures, the purified PCR amplification product is spotted on a slide glass for microarray. The spots are irradiated with UV light (60 mJ to 300 mJ/cm$^2$) to fix the PCR amplification product (comprising target genomic DNA derived from *M. avium*) on the slide glass, and thus the microarray is prepared.

It should be noted that, on the obtained microarray, if necessary, a control sample may be fixed in parallel on the above-described microarray to select the spots comprising DNA fragment which is capable of hybridizing specifically with the nucleotide sequence for a *M. avium* gene.

For example, using a genomic DNA fragment derived from species intended to be differentiated [for example, the DNA fragment of a sequence owned by *M. intracellulare* such as rps 1 (Patent Literature 1), the DNA fragment of a nucleotide sequence specific for *M. kansasii* such as KATS2 sequence (JP-A-H11-155589), and for example, the DNA derived from bacteria other than *Mycobacterium* genus such as *E. coli*, and the like], and a known DNA fragment which gives an indication for comparing and evaluating the specificity [for example, a DNA fragment of known nucleotide sequence owned by *M. avium* such as MAV19K (Patent Literature 1)], these are fixed in parallel with the above-described PCR product derived from the shotgun clone on the slide glass. By the use of these spots as a control, precision of assay in the selection of the spot of DNA fragment which is capable of hybridizing specifically with the nucleotide sequence for a *M. avium* gene can be increased.

(4) Labeling of Target Genomic DNA with Fluorescent Dye i) Labeling of Target Genomic DNA with Fluorescent Dye For example, by the conventional method such as indirect labeling method using hexylamino-UTP, for example, the purified genomic DNA derived from *M. avium* obtained by the above described method (1) is labeled with labeling substance. In addition, genomic DNA as a control (for example, nontuberculous acid fast bacteria such as *M. intracellulare*, tuberculosis bacteria such as *M. Bovis*, and the like) is labeled with a different labeling substance from that used for labeling the purified genomic DNA derived from *M. avium*.

Labeling substance to be used for labeling the above-described DNA is the labeling substances usually used in this field, and widely used labeling substances include Cy3 (product name of Amersham Biosciences K.K.), Cy5 (product name of Amersham Biosciences K.K.), Alexa555 (product name of Invitrogen Corp.), Alexa647 (product name of Invitrogen Corp.) and the like.

For example, for an indirect labeling method which has been modified from a protocol published by DeRisi Laboratory (www.microarray.org), a labeling method using Cy3 and Cy5 as labeling substances will be explained as an example. In this method, at first, by carrying out an enzymatic extension reaction, a DNA chain which has been incorporated with a αUTP having an amino group into the molecule is produced. And, to this amino group of the DNA, a fluorescent dye (succinimide body) is coupled chemically, thereby, the DNA is labeled.

That is, at first, the starting materials (genomic DNA from *M. avium* and genomic DNA for control) are subjected to heat denaturation treatment according to the conventional procedure [otherwise, a commercially available kit such as BioPrime DNA labeling system (product of Invitrogen Corp.) may be used]. After that, to the heat treated material, 2 μl DTT, a mixed solution of dATP/dCTP/dGTP, dTTP, Ha-dUTP and Klenow enzyme are added, and the extension reaction is carried out at 37° C. for about 3 hours. The obtained reaction product is placed onto an ultrafiltration column and centrifuged at 14,000 rpm for about 4 minutes, and the concentrated solution is recovered in a microtube, and then dried thoroughly using a centrifugal vacuum drier and the like. After that, to the dried above reaction product, $NaHCO_3$ is added and mixed, and then left standing at ambient temperature for 2 to 3 minutes.

Separately, a solution of Cy3 (or Cy5) dissolved in DMSO (Cy-dye Solution Cy3, Cy-dye Solution Cy5) is prepared. This Cy-dye Solution Cy3 is added to the above-described reaction product obtained by use of DNA derived from genome for control. Also, the Cy-dye Solution Cy5 is added to the above-described reaction product obtained by use of genomic DNA derived from *M. avium*. Each mixture is incubated under light shielding at 40° C. for about 60 minutes. Further, each reaction product is added with 4 M $NH_2OH$ and mixed, and incubated under light shielding for about 15 minutes to obtain labeled product of each genomic DNA. After that, the obtained labeled product is placed onto an ultrafiltration column and centrifuged at 14,000 rpm for about 4 minutes. The concentrated solution is recovered in a microtube, and then dried thoroughly using a centrifugal vacuum drier.

ii) Fragmentation Process of the Labeled Products

To each of the labeled products of the DNA derived from each genome in dry state obtained in the above i) of (4), a solution having composition of 0.04 M Tris-acetate (pH 8.1), 0.1 M potassium acetate, and 0.03 M magnesium acetate tetrahydrate is prepared and added. To aforementioned solution, the labeled product of genomic DNA fragments in dry state is mixed in suspension. The suspension is heat-treated at 94° C. for about 15 minutes, and the fragment of labeled product of genomic DNA fragments with 100 to 300 bases is obtained (Cy3-labeled product, Cy5-labeled product).

The Cy3-labeled product and the Cy5-labeled product obtained are each placed onto an ultrafiltration column and centrifuged at 14,000 rpm for about 4 minutes, and each concentrated solution is recovered in a microtube, and then dried thoroughly using a centrifugal vacuum drier and the like.

After that, to this microtube, a reagent solution which contains salmon sperm DNA (10 mg/ml) and formamide, and adjusted the total volume to give 40 to 50 μl using ArrayHyb Hybridization buffer (SIGMA) (this composition is for a case where a size of cover glass to be used for the subsequent microarray is 24×55 mm) is added, and the dry material obtained above is mixed in suspension in the same solution, and then incubated at 95° C. for about 5 minutes to prepare a mixed solution of the Cy3- and Cy5-labeled products (a mixed solution of the fragmentation product of the Cy5-labeled product of the genomic DNA derived from *M. avium* and the fragmentation product of the Cy3-labeled product of the genomic DNA derived from the control genome). The mixed solution is kept at 70° C. until it is used for the microarray hybridization in the following (5).

(5) Microarray Hybridization (DNA-DNA Hybridization on the Array)

Next, for the microarray of Whole Genome Shotgun clone of genomic DNA derived from *M. avium*, hybridization with Cy3- and Cy5-labeled products is carried out.

For example, on a microarray of Whole Genome Shotgun clone of genomic DNA derived from *M. avium* obtained in the above-described step (3), a mixed solution of Cy3- and Cy5-labeled products prepared in the above described ii) of (4) is placed, and covered with a cover glass. The microarray is set on a Hybri-cassette, and kept at 65° C. under light shielding for not less than 8 hours to allow hybridization. After hybridization, the microarray is dipped in a 2×SSC to 0.1% SDS solution together with the cover glass at room temperature, and the cover glass is removed. After sequential washing with 1×SSC solution containing 0.03% SDS (60° C.) for 10 minutes, 0.2×SSC solution (42° C.) for 10 minutes and 0.05×SSC solution (room temperature) for 10 minutes, the microarray is dried by centrifugation at 800 rpm for 5 minutes.

(6) Measurement of Fluorescence Intensity; from Detection of Signal to Quantification Using a fluorescence readout scanner, the fluorescence intensity derived from the microarray on which the microarray hybridization has been carried out as described in the above (5) is measured. On this occasion, the fluorescence intensity is measured by 2 channels of Cy3 and Cy5, and fluorescence detection data are obtained. Quantification of the fluorescence signal may be carried out using commercially available DNA chip expression image analysis software and the like and by performing automated spot recognition, background calculation, and normalization of the fluorescence intensity ratio according to the operation manual of the software.

The Cy5-labeled product used for hybridization is a group of labeled DNA fragments prepared using the genomic DNA derived from M. avium as a material, and the Cy3-labeled product is a group of labeled DNA fragments prepared using genomic DNA for control as a material. Therefore, in the measurement of fluorescence intensity derived from Cy3 and Cy5 of a certain spot on a microarray, when the fluorescence intensity ratio of Cy5 for Cy3 is high, it indicates that the DNA fragment (PCR product) in the spot has hybridized more strongly with the Cy5-labeled product, namely, with the genomic DNA derived from M. avium. And the specificity of the DNA fragment (PCR product) for M. avium is deemed to be high.

On the other hand, in the measurement of fluorescence intensity derived from Cy3 and Cy5 of a certain spot, when the fluorescence intensity ratio of Cy5 for Cy3 is low, it indicates that there observed cross-reaction of the DNA fragment (PCR product) in the spot with the Cy3-labeled product, namely with the genomic DNA for control. In this case, and the case when the fluorescence intensity derived from Cy3 and Cy5 are detected in the same level, or no fluorescence derived from Cy3 and Cy5 is detected, the specificity of the DNA fragment (PCR product) for M. avium is deemed to be low.

And so, for example, on the basis of the fluorescence intensity ratio of Cy3/Cy5 (Ratio) detected on the microarray, the results are analyzed, for example, by making up a scatter chart (scatter plot). And screening for a specific sequence for a M. avium is carried out.

Among candidates obtained by the screening, as a result of numerical analysis of Cy3/Cy5 ratio, a clone which provides significantly specific signal for M. avium (when the fluorescence intensity derived from Cy5 is strong) is selected.

It should be noted that, when a positive control and a negative control are spotted on the microarray as described above, the fluorescence intensities of Cy3 and Cy5 in each control spot are measured. And, by looking at the tendency of fluorescence intensities, selection of the objective spot can be performed more precisely.

For example, among the candidates obtained by screening, as a result of numerical analysis of Cy3/Cy5 ratio, a spot (clone) which provides a significantly specific signal for M. avium (when the fluorescence intensity derived from Cy5 is strong), and yet provides a greater numerical value of the Ratio (the fluorescence intensity derived from Cy5 is strong) compared with that of the positive control spot specific for the above-described M. avium, is selected.

Next, using equipment usually used in this field such as a sequencer, determination of nucleotide sequence of the obtained candidate clone may be carried out according to the conventional procedures.

The primer for detection of M. avium involved in the present invention includes a primer comprising an oligonucleotide which comprises a part or an entire of the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, or a part or an entire of the sequence complementary to the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, and which is capable of hybridizing with the nucleotide sequence for a M. avium gene (hereinafter, sometimes referred to as the primer of the present invention).

In addition, the primer of the present invention may be designed, in compliance with the condition of the nucleic acid amplification reaction such as PCR (including the real-time PCR), the condition of nucleic acid hybridization and the like, by selecting an appropriate region and an appropriate length in consideration of dissociation temperature (Tm value) and the like from oligonucleotides which comprises a part or an entire of the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, or a part or an entire of the sequence complementary to the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136.

Preferably, the primer includes an oligonucleotide having a length with 10 to 50 nucleotides, more preferably 10 to 35 nucleotides, further more preferably 18 to 25 nucleotides which is considered to be a necessary nucleotide number for retaining specificity as a primer.

As to a method for designing primer, the primer may be designed using software commonly used for designing primer such as, for example, a primer design tool on the web, Primer 3 (Whitehead Institute for Biomedical Research) and the like.

A specific example of an oligonucleotide to be used for the primer of the present invention (the oligonucleotide of the present invention), which comprises a part or an entire of the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO: 134, SEQ ID NO:135, and SEQ ID NO:136, or a part or an entire of the sequence complementary to the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, and which is capable of hybridizing with the nucleotide sequence for a *M. avium* gene, is the same as described in the above explanation for the oligonucleotide of the present invention.

Specific examples of the primer of the present invention include, for example, the one which comprises an oligonucleotide comprising a part or an entire sequence selected from SEQ ID NO:6 to 32, SEQ ID NO:43 to 129 and SEQ ID NO:137 to 205, or a part or an entire sequence complementary to the sequence selected from SEQ ID NO:6 to 32, SEQ ID NO:43 to 129 and SEQ ID NO:137 to 205, and which is capable of hybridizing with the nucleotide sequence for a *M. avium* gene.

Preferable primer include an oligonucleotide which comprises a part or an entire of the nucleotide sequence selected from SEQ ID NO:6 to 23, SEQ ID NO:43 to 100 and SEQ ID NO:137 to 182, and which is capable of hybridizing with the nucleotide sequence for a *M. avium* gene, or an oligonucleotide which comprises a part or an entire of the sequence complementary to the nucleotide sequence selected from SEQ ID NO:6 to 23, SEQ ID NO:43 to 100 and SEQ ID NO:137 to 182, and which is capable of hybridizing with the nucleotide sequence for a *M. avium* gene.

More preferable primer includes a primer which comprises a part or an entire of the nucleotide sequence selected from SEQ ID NO:6, 7, 10 to 17, 22, 23, 57 to 72, 75 to 94, 137 to 205, or a primer which comprises a part or an entire of the sequence complementary to the nucleotide sequence selected from SEQ ID NO:6, 7, 10 to 17, 22, 23, 57 to 72, 75 to 94, 137 to 205.

Further more preferable primer includes a primer which comprises a part or an entire of the nucleotide sequence selected from SEQ ID NO:6, 7, 10 to 17, 22, 23, 59 to 72, 75 to 78, 81 to 94, 137 to 205, or a primer which comprises a part or an entire of the sequence complementary to the nucleotide sequence selected from SEQ ID NO:6, 7, 10 to 17, 22, 23, 59 to 72, 75 to 78, 81 to 94, 137 to 205.

Yet further more preferable primer includes a primer which comprises a part or an entire of the nucleotide sequence selected from SEQ ID NO:137 to 205, or a primer which comprises a part or an entire of the sequence complementary to the nucleotide sequence selected from SEQ ID NO:137 to 205. Among them, the primer which comprises the nucleotide sequence selected from SEQ ID NO:137-182, or the primer which comprises the sequence complementary to the nucleotide sequence selected from SEQ ID NO:137-182 is included.

It should be noted that, the primers which comprise the nucleotide sequence shown in SEQ ID NO:6 to 9 are designed based on the nucleotide sequence shown in SEQ ID NO:1.

The primers which comprise the nucleotide sequence shown in SEQ ID NO:10 to 11 are designed based on the nucleotide sequence shown in SEQ ID NO:2.

The primers which comprise the nucleotide sequence shown in SEQ ID NO:12 to 13 are designed based on the nucleotide sequence shown in SEQ ID NO:3.

The primers which comprise the nucleotide sequence shown in SEQ ID NO:14 to 21 are designed based on the nucleotide sequence shown in SEQ ID NO:4.

The primers which comprise the nucleotide sequence shown in SEQ ID NO:22 to 23 are designed based on the nucleotide sequence shown in SEQ ID NO:5.

The primers which comprise the nucleotide sequence shown in SEQ ID NO:43 to 54 are designed based on the nucleotide sequence shown in SEQ ID NO:37.

The primers which comprise the nucleotide sequence shown in SEQ ID NO:55 to 66 are designed based on the nucleotide sequence shown in SEQ ID NO:38.

The primers which comprise the nucleotide sequence shown in SEQ ID NO:67 to 74 are designed based on the nucleotide sequence shown in SEQ ID NO:39.

The primers which comprise the nucleotide sequence shown in SEQ ID NO:75 to 82 are designed based on the nucleotide sequence shown in SEQ ID NO:40.

The primers which comprise the nucleotide sequence shown in SEQ ID NO:83 to 92 are designed based on the nucleotide sequence shown in SEQ ID NO:41.

The primers which comprise the nucleotide sequence shown in SEQ ID NO:93 to 100 are designed based on the nucleotide sequence shown in SEQ ID NO:42.

The primers which comprise the nucleotide sequence shown in SEQ ID NO:137 to 144 are designed based on the nucleotide sequence shown in SEQ ID NO:130.

The primers which comprise the nucleotide sequence shown in SEQ ID NO:145-148 are designed based on the nucleotide sequence shown in SEQ ID NO:131.

The primers which comprise the nucleotide sequence shown in SEQ ID NO:149 to 158 are designed based on the nucleotide sequence shown in SEQ ID NO:132.

The primers which comprise the nucleotide sequence shown in SEQ ID NO:159 to 164 are designed based on the nucleotide sequence shown in SEQ ID NO:133.

The primers which comprise the nucleotide sequence shown in SEQ ID NO:165 to 170 are designed based on the nucleotide sequence shown in SEQ ID NO:134.

The primers which comprise the nucleotide sequence shown in SEQ ID NO:171 to 174 are designed based on the nucleotide sequence shown in SEQ ID NO:135.

The primers which comprise the nucleotide sequence shown in SEQ ID NO:175 to 182 are designed based on the nucleotide sequence shown in SEQ ID NO:136.

In addition, in the nucleotide sequence shown in SEQ ID NO:1, location of the nucleotide sequences which were designed as a primer having nucleotide sequences shown in SEQ ID NO:6 to 9 are each as follows:
SEQ ID NO:6 (003Fw_1): 804th to 823rd;
SEQ ID NO:7 (003Rv_1): 707th to 725th;
SEQ ID NO:8 (003Fw_2): 20th to 37th;
SEQ ID NO:9 (003Rv_2): 136th to 153rd.

In the nucleotide sequence shown in SEQ ID NO:2, location of the nucleotide sequences which were designed as a primer having nucleotide sequences shown in SEQ ID NO:10 to 11 are each as follows:
SEQ ID NO:10 (007Fw_1): 3rd to 21st;
SEQ ID NO:11 (007Rv_1): 122nd to 139th.

In the nucleotide sequence shown in SEQ ID NO:3, location of the nucleotide sequences which were designed as a primer having nucleotide sequences shown in SEQ ID NO:12 to 13 are each as follows:
SEQ ID NO:12 (11Fw_1): 481st to 500th;
SEQ ID NO:13 (11Rv_1): 346th to 366th.

In the nucleotide sequence shown in SEQ ID NO:4, location of the nucleotide sequences which were designed as a primer having nucleotide sequences shown in SEQ ID NO:14 to 21 are each as follows:
SEQ ID NO:14 (12Fw_1): 12th to 32nd;
SEQ ID NO:15 (12Rv_1): 143rd to 161st;
SEQ ID NO:16 (12Fw_4): 126th to 145th;
SEQ ID NO:17 (12Rv_4): 287th to 308th;

SEQ ID NO:18 (12Fw_2): 448th to 465th;
SEQ ID NO:19 (12Rv_2): 559th to 579th;
SEQ ID NO:20 (12Fw_3): 293rd to 312th;
SEQ ID NO:21 (12Rv_3): 452nd to 472nd.

In the nucleotide sequence shown in SEQ ID NO:5, location of the nucleotide sequences which were designed as a primer having nucleotide sequences shown in SEQ ID NO:22 to 23 are each as follows:
SEQ ID NO:22 (04Fw_1): 574th to 594th;
SEQ ID NO:23 (04Rv_1): 397th to 417th.

In the nucleotide sequence shown in SEQ ID NO:37, location of the nucleotide sequences which were designed as a primer having nucleotide sequences shown in SEQ ID NO:43 to 54 are each as follows:
SEQ ID NO:43 (RE01Fw_01): 765th to 783rd;
SEQ ID NO:44 (RE01Rv_01): 891st to 910th;
SEQ ID NO:45 (RE01Fw_02): 813th to 830th;
SEQ ID NO:46 (RE01Rv_02): 961st to 978th;
SEQ ID NO:47 (RE01Fw_03): 204th to 221st;
SEQ ID NO:48 (RE01Rv_03): 386th to 403rd;
SEQ ID NO:49 (RE01Fw_04): 68th to 87th;
SEQ ID NO:50 (RE01Rv_04): 190th to 207th;
SEQ ID NO:51 (RE01Fw_05): 386th to 403rd;
SEQ ID NO:52 (RE01Rv_05): 517th to 535th;
SEQ ID NO:53 (RE01Fw_06): 615th to 635th;
SEQ ID NO:54 (RE01Rv_06): 734th to 751st.

In the nucleotide sequence shown in SEQ ID NO:38, location of the nucleotide sequences which were designed as a primer having nucleotide sequences shown in SEQ ID NO:55 to 66 are each as follows:
SEQ ID NO:55 (RE04Fw_01): 206th to 224th;
SEQ ID NO:56 (RE04Rv_01): 360th to 378th;
SEQ ID NO:57 (RE04Fw_02): 35th to 52nd;
SEQ ID NO:58 (RE04Rv_02): 206th to 224th;
SEQ ID NO:59 (RE04Fw_03): 611th to 630th;
SEQ ID NO:60 (RE04Rv_03): 744th to 762nd;
SEQ ID NO:61 (RE04Fw_04): 570th to 589th;
SEQ ID NO:62 (RE04Rv_04): 727th to 746th;
SEQ ID NO:63 (RE04Fw_05): 435th to 453rd;
SEQ ID NO:64 (RE04Rv_05): 572nd to 593rd;
SEQ ID NO:65 (RE04Fw_06): 748th to 767th;
SEQ ID NO:66 (RE04Rv_06): 890th to 909th.

In the nucleotide sequence shown in SEQ ID NO:39, location of the nucleotide sequences which were designed as a primer having nucleotide sequences shown in SEQ ID NO:67 to 74 are each as follows:
SEQ ID NO:67 (RE10Fw_02): 783rd to 800th;
SEQ ID NO:68 (RE10Rv_02): 879th to 896th;
SEQ ID NO:69 (RE10Fw_03): 59th to 77th;
SEQ ID NO:70 (RE10Rv_03): 239th to 257th;
SEQ ID NO:71 (RE10Fw_04): 590th to 607th;
SEQ ID NO:72 (RE10Rv_04): 789th to 809th;
SEQ ID NO:73 (RE10Fw_05): 377th to 396th;
SEQ ID NO:74 (RE10Rv_05): 501st to 518th.

In the nucleotide sequence shown in SEQ ID NO:40, location of the nucleotide sequences which were designed as a primer having nucleotide sequences shown in SEQ ID NO:75 to 82 are each as follows:
SEQ ID NO:75 (RE11Fw_01): 264th to 281st;
SEQ ID NO:76 (RE11Rv_01): 379th to 397th;
SEQ ID NO:77 (RE11Fw_02): 106th to 123rd;
SEQ ID NO:78 (RE11Rv_02): 278th to 296th;
SEQ ID NO:79 (RE11Fw_03): 375th to 392nd;
SEQ ID NO:80 (RE11Rv_03): 531st to 548th;
SEQ ID NO:81 (RE11Fw_04): 526th to 543rd;
SEQ ID NO:82 (RE11Rv_04): 709th to 726th.

In the nucleotide sequence shown in SEQ ID NO:41, location of the nucleotide sequences which were designed as a primer having nucleotide sequences shown in SEQ ID NO:83 to 92 are each as follows:
SEQ ID NO:83 (RE23Fw_01): 34th to 53rd;
SEQ ID NO:84 (RE23Rv_01): 157th to 176th;
SEQ ID NO:85 (RE23Fw_02): 159th to 178th;
SEQ ID NO:86 (RE23Rv_02): 305th to 322nd;
SEQ ID NO:87 (RE23Fw_03): 462nd to 481st;
SEQ ID NO:88 (RE23Rv_03): 584th to 603rd;
SEQ ID NO:89 (RE23Fw_04): 436th to 453rd;
SEQ ID NO:90 (RE23Rv_04): 535th to 552nd;
SEQ ID NO:91 (RE23Fw_05): 279th to 298th;
SEQ ID NO:92 (RE23Rv_05): 401st to 419th.

In the nucleotide sequence shown in SEQ ID NO:42, location of the nucleotide sequences which were designed as a primer having nucleotide sequences shown in SEQ ID NO:93 to 100 are each as follows:
SEQ ID NO:93 (RE24Fw_01): 328th to 347th;
SEQ ID NO:94 (RE24Rv_01): 414th to 433rd;
SEQ ID NO:95 (RE24Fw_02): 178th to 196th;
SEQ ID NO:96 (RE24Rv_02): 328th to 347th;
SEQ ID NO:97 (RE24Fw_03): 103rd to 120th;
SEQ ID NO:98 (RE24Rv_03): 274th to 291st;
SEQ ID NO:99 (RE24Fw_04): 387th to 406th;
SEQ ID NO:100 (RE24Rv_04): 537th to 555th.

In the nucleotide sequence shown in SEQ ID NO:130, location of the nucleotide sequences which were designed as a primer having nucleotide sequences shown in SEQ ID NO:137 to 144 are each as follows:
SEQ ID NO:137 (Mac_06Fw01): 88th to 105th;
SEQ ID NO:138 (Mac_06Rv01): 223rd to 241st;
SEQ ID NO:139 (Mac_06Fw02): 156th to 175th;
SEQ ID NO:140 (Mac_06Rv02): 312th to 331st;
SEQ ID NO:141 (Mac_06Fw03): 460th to 478th;
SEQ ID NO:142 (Mac_06Rv03): 604th to 623rd;
SEQ ID NO:143 (Mac_06Fw04): 604th to 623rd;
SEQ ID NO:144 (Mac_06Rv04): 743rd to 760th.

In the nucleotide sequence shown in SEQ ID NO:131, location of the nucleotide sequences which were designed as a primer having nucleotide sequences shown in SEQ ID NO:145 to 148 are each as follows:
SEQ ID NO:145 (Mac_10Fw01): 94th to 113th;
SEQ ID NO:146 (Mac_10Rv01): 228th to 245th;
SEQ ID NO:147 (Mac_10Fw02): 280th to 299th;
SEQ ID NO:148 (Mac_10Rv02): 453rd to 472nd.

In the nucleotide sequence shown in SEQ ID NO:132, location of the nucleotide sequences which were designed as a primer having nucleotide sequences shown in SEQ ID NO:149 to 158 are each as follows:
SEQ ID NO:149 (Mac_11Fw01): 71st to 88th;
SEQ ID NO:150 (Mac_11Rv01): 228th to 248th;
SEQ ID NO:151 (Mac_11Fw02): 477th to 496th;
SEQ ID NO:152 (Mac_11Rv02): 596th to 615th;
SEQ ID NO:153 (Mac_11Fw03): 536th to 554th;
SEQ ID NO:154 (Mac_11Rv03): 617th to 635th;
SEQ ID NO:155 (Mac_11Fw04): 558th to 575th;
SEQ ID NO:156 (Mac_11Rv04): 671st to 688th;
SEQ ID NO:157 (Mac_11Fw05): 299th to 316th;
SEQ ID NO:158 (Mac_11Rv05): 391st to 410th.

In the nucleotide sequence shown in SEQ ID NO:133, location of the nucleotide sequences which were designed as a primer having nucleotide sequences shown in SEQ ID NO:159 to 164 are each as follows:
SEQ ID NO:159 (Mac_12Fw01): 271st to 290th;
SEQ ID NO:160 (Mac_12Rv01): 416th to 433rd;
SEQ ID NO:161 (Mac_12Fw02): 603rd to 622nd;

SEQ ID NO:162 (Mac_12Rv02): 747th to 765th;
SEQ ID NO:163 (Mac_12Fw03): 58th to 75th;
SEQ ID NO:164 (Mac_12Rv03): 198th to 216th.

In the nucleotide sequence shown in SEQ ID NO:134, location of the nucleotide sequences which were designed as a primer having nucleotide sequences shown in SEQ ID NO:165 to 170 are each as follows:
SEQ ID NO:165 (Mac_13Fw01): 108th to 126th;
SEQ ID NO:166 (Mac_13Rv01): 288th to 305th;
SEQ ID NO:167 (Mac_13Fw02): 321st to 339th;
SEQ ID NO:168 (Mac_13Rv02): 453rd to 472nd;
SEQ ID NO:169 (Mac_13Fw03): 576th to 595th;
SEQ ID NO:170 (Mac_13Rv03): 720th to 739th.

In the nucleotide sequence shown in SEQ ID NO:135, location of the nucleotide sequences which were designed as a primer having nucleotide sequences shown in SEQ ID NO:171 to 174 are each as follows:
SEQ ID NO:171 (Mac_15Fw01): 233rd to 250th;
SEQ ID NO:172 (Mac_15Rv01): 326th to 346th;
SEQ ID NO:173 (Mac_15Fw02): 442nd to 460th;
SEQ ID NO:174 (Mac_15Rv02): 527th to 546th.

In the nucleotide sequence shown in SEQ ID NO:136, location of the nucleotide sequences which were designed as a primer having nucleotide sequences shown in SEQ ID NO:175 to 182 are each as follows:
SEQ ID NO:175 (Mac_16Fw02): 848th to 867th;
SEQ ID NO:176 (Mac_16Rv02): 952nd to 969th;
SEQ ID NO:177 (Mac_16Fw03): 135th to 152nd;
SEQ ID NO:178 (Mac_16Rv03): 222nd to 240th;
SEQ ID NO:179 (Mac_16Fw05): 544th to 562nd;
SEQ ID NO:180 (Mac_16Rv05): 669th to 688th;
SEQ ID NO:181 (Mac_16Fw07): 703rd to 720th;
SEQ ID NO:182 (Mac_16Rv07): 792nd to 812th.

It should be noted that, in the above description, names of the primers denominated in the present invention are shown in parenthesis next to each SEQ ID NO.

A method for obtaining the primer of the present invention is as described above in the method for obtaining the nucleotide of the present invention.

In addition, the primer of the present invention may be labeled with a labeling substance.

The method for labeling the primer of the present invention includes the labeling methods of the oligonucleotide usually conducted in this field, and the methodology may be selected appropriately depending on the labeling substance.

As to the labeling substance to be used for labeling the primer of the present invention, any of the known labeling substances such as radioisotope and enzyme, fluorescent substance, luminescent substance, biotin and the like may be used.

For example, the radioisotope includes $^{32}P$, $^{33}P$, $^{35}S$ and the like; the enzyme includes alkaline phosphatase, horseradish peroxydase and the like; the fluorescent substance includes cyanine dye type of Cy3, Cy5 (Amersham Biosciences K.K.), Alexa555, Alexa647 (Invitrogen Corp.), fluorescein and the like; the luminescent substance includes chemiluminescent reagents including Acridinium Ester and the like.

The method for labeling the primer of the present invention with a radioisotope includes the method of labeling by incorporation of a radioisotope-labeled nucleotide into a primer at the time when the primer is synthesized, or labeling with a radioisotope after the primer is synthesized and the like. Specifically, commonly used random primer method, nick-translation method, 5'-terminal labeling method using T4 polynucleotide kinase, 3'-terminal labeling method using terminal deoxynucleotidyl transferase, RNA labeling method and the like are included.

The method for labeling the primer of the present invention with enzyme includes direct labeling methods of conventional technique in this field, in which an enzyme molecule such as alkaline phosphatase, horseradish peroxidase and the like is directly and covalently linked to the primer to be labeled.

As to the method for labeling the primer of the present invention with fluorescent substance includes, for example, a method in which the fluorescent-labeled nucleotide may be incorporated into the primer by a conventional labeling technique in this field. In addition, also, by a method of replacing a nucleotide in a sequence with a nucleotide having a linker arm (See, for example, Nucleic Acids Res., 1986, vol. 14, p. 6115), the nucleotide can be labeled with fluorescent substance. In this case, there may be a method in which a uridine having a linker arm on 5-position is synthesized chemically from deoxyuridine by a synthesis method disclosed in JP-A-S60-500717, and using it, a fluorescent substance is introduced into the above-described oligonucleotide chain.

The methods for labeling the primer of the present invention with a luminescent substance or with biotin include a conventional technique of luminescent-labeling or biotin-labeling usually performed for nucleotides in this field.

The probe for detection of M. avium involved in the present invention includes a probe comprising an oligonucleotide (an oligonucleotide of the present invention) which comprises a part or an entire of the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, or a part or an entire of the sequence complementary to the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, and which is capable of hybridizing with the nucleotide sequence for a M. avium gene (hereinafter, sometimes referred to as the probe of the present invention).

The probe of the present invention may be used, in compliance with the condition of the nucleic acid amplification reaction such as PCR (including the real-time PCR), the condition of nucleic acid hybridization and the like, by selecting an appropriate region and an appropriate length in consideration of dissociation temperature (Tm value) and the like from oligonucleotides which comprises a part or an entire of the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, or a part or an entire of the sequence complementary to the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136. In this regard, however, if the probe is intended to be retained sufficient specificity, it is desirable to design the probe in consideration of nucleotide number necessary for retaining specificity as a probe.

For example, the probe to be used for the nucleic acid hybridization method and the like (for example, Southern hybridization) includes a probe having a length of 10 to 700 nucleotides, preferably 100 to 600 nucleotides, further preferably 200 to 500 nucleotides.

In addition, for example, the probe to be used for the real-time PCR amplification method and the like (for example, TaqMan™ method, Molecular Beacon method and so on) includes the one having a length of 10 to 50 nucleotides, preferably 15 to 40 nucleotides, further preferably 20 to 30 nucleotides.

A specific example of an oligonucleotide to be used for the probe of the present invention (the oligonucleotide of the present invention), which comprises a part or an entire of the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, or a part or an entire of the sequence complementary to the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, and which is capable of hybridizing with the nucleotide sequence for a *M. avium* gene.

More preferable probe includes a probe which comprises a part or an entire of the nucleotide sequence selected from SEQ ID NO:6, 7, 10 to 17, 22 to 24, 26-29, 32, 57 to 72, 75 to 94, 108-115, 117-126, 137 to 205, or a probe which comprises a part or an entire of the sequence complementary to the nucleotide sequence selected from SEQ ID NO:6, 7, 10 to 17, 22 to 24, 26-29, 32, 57 to 72, 75 to 94, 108 to 115, 117 to 126, 137 to 205.

Further preferable probe includes a probe which comprises a part or an entire of the nucleotide sequence selected from SEQ ID NO:137 to 205, or a probe which comprises a part or an entire of the sequence complementary to the nucleotide sequence selected from SEQ ID NO:137 to 205.

It should be noted that, the nucleotide sequence selected from SEQ ID NO:24 to 32, SEQ ID NO:101 to 129 and SEQ ID NO:183 to 205, or the complementary sequence thereto is a nucleotide sequence of an oligonucleotide to be amplified by the PCR using the primer of the present invention. Combination of the forward primer and the reverse primer, and the SEQ ID NO of the nucleotide sequence to be amplified by the PCR using such combination are shown collectively in Table 1. For example, the nucleotide sequence shown in SEQ ID NO:24 indicates a nucleotide sequence of the oligonucleotide to be amplified by the PCR using an oligonucleotide having a nucleotide sequence shown in SEQ ID NO:6 as a forward primer and an oligonucleotide having a nucleotide sequence shown in SEQ ID NO:7 as a reverse primer.

TABLE 1

| Forward Primer SEQ ID NO: 6 | Reverse Primer SEQ ID NO: 7 | Sequence to be amplified SEQ ID NO: 24 | Forward Primer SEQ ID NO: 67 | Reverse Primer SEQ ID NO: 68 | Sequence to be amplified SEQ ID NO: 113 | Forward Primer SEQ ID NO: 143 | Reverse Primer SEQ ID NO: 144 | Sequence to be amplified SEQ ID NO: 186 |
|---|---|---|---|---|---|---|---|---|
| 8 | 9 | 25 | 69 | 70 | 114 | 145 | 146 | 187 |
| 10 | 11 | 26 | 71 | 72 | 115 | 147 | 148 | 188 |
| 12 | 13 | 27 | 73 | 74 | 116 | 149 | 150 | 189 |
| 14 | 15 | 28 | 75 | 76 | 117 | 151 | 152 | 190 |
| 16 | 17 | 29 | 77 | 78 | 118 | 153 | 154 | 191 |
| 18 | 19 | 30 | 79 | 80 | 119 | 155 | 156 | 192 |
| 20 | 21 | 31 | 81 | 82 | 120 | 157 | 158 | 193 |
| 22 | 23 | 32 | 83 | 84 | 121 | 159 | 160 | 194 |
| 43 | 44 | 101 | 85 | 86 | 122 | 161 | 162 | 195 |
| 45 | 46 | 102 | 87 | 88 | 123 | 163 | 164 | 196 |
| 47 | 48 | 103 | 89 | 90 | 124 | 165 | 166 | 197 |
| 49 | 50 | 104 | 91 | 92 | 125 | 167 | 168 | 198 |
| 51 | 52 | 105 | 93 | 94 | 126 | 169 | 170 | 199 |
| 53 | 54 | 106 | 95 | 96 | 127 | 171 | 172 | 200 |
| 55 | 56 | 107 | 97 | 98 | 128 | 173 | 174 | 201 |
| 57 | 58 | 108 | 99 | 100 | 129 | 175 | 176 | 202 |
| 59 | 60 | 109 | 137 | 138 | 183 | 177 | 178 | 203 |
| 61 | 62 | 110 | 139 | 140 | 184 | 179 | 180 | 204 |
| 63 | 64 | 111 | 141 | 142 | 185 | 181 | 182 | 205 |
| 65 | 66 | 112 | | | | | | | hybridizing with the nucleotide sequence for a *M. avium* gene, is the same as described in the above explanation of the oligonucleotide of the present invention.

Specific example of preferable probe of the present invention include an oligonucleotide which comprises a part or an entire of the nucleotide sequence selected from SEQ ID NO:6 to 32, SEQ ID NO:43 to 129 and SEQ ID NO:137 to 205, and which is capable of hybridizing with the nucleotide sequence for a *M. avium* gene, or an oligonucleotide which comprises a part or an entire of the sequence complementary to the nucleotide sequence selected from SEQ ID NO:6 to 32, SEQ ID NO:43 to 129 and SEQ ID NO:137 to 205, and A method for obtaining the probe of the present invention is as described above in the method for obtaining the nucleotide of the present invention.

The probe of the present invention may be labeled with a labeling substance.

As to the labeling substance to be used for labeling the probe of the present invention, any of the known labeling substances such as radioisotope and enzyme, fluorescent substance, luminescent substance, biotin and the like may be used.

The specific examples of the labeling substance and the labeling method to be used for labeling the probe of the present invention are as described in the labeling method of the primer of the present invention.

In addition, the labeled probe to be used in the detection method by the real-time PCR as described later includes the probe of the present invention which has been labeled with a labeling substance usually used in the real-time method. For example, the labeled probe of the present invention in which the 5'-terminal has been labeled with a reporter fluorescent substance [carboxyfluorescein (FAM), hexachlorofluorescein (HEX), tetrachlorofluorescein (TET) and the like] and 3'-terminal has been labeled with a quencher dye [for example, a fluorescent substance such as carboxytetramethylrhodamine (TAMRA), nonfluorescent substance such as Black Hole Quencher dye (BHQ) and 4-((4-(dimethylamino)phenyl)azo)benzoic acid (DABCYL), and the like] is included.

In the method for detection by the TaqMan™ real-time PCR method to be described hereinafter, the above described labeled probe can also be used.

Sample to be used for the detection of *M. avium* involved in the present invention includes various kinds of clinical specimen such as sputum, blood, pharyngeal mucosa, gastric juice, bronchial washing fluid, transbronchial specimen, puncture fluid such as pleural effusion, urine, pus, and the like. In addition, the sample may be the microbial cell isolated and cultured from a specimen; the nucleic acid isolated and purified from such microbial cell; or the nucleic acid amplified by the nucleic acid amplification detection system and the like.

The extraction and purification of the DNA from the above described samples may be carried out according to the conventional procedures usually used for the extraction of acid-fast bacterium (tuberculosis bacterium) DNA from a specimen.

First, the cell wall of microbial cell in the sample is needed to be broken down. The method for this purpose includes, for example, in the case where the microbial cell is used as a sample, a method for disruption of the membrane structure of tuberculosis bacterium by treating the microbial cell with surface active agent such as SDS, protein denaturing agent such as guanidine thiocyanate (GTC) and the like, and a method of physical disruption of the microbial cell using glass beads and the like.

In the case where the expectorated sputum is used as a sample, as a pretreatment, it is desirable to conduct homogenization of the specimen material by NALC (N-acetyl-L-cysteine)-NaOH method (Kent P T, Kubica G P, Pubric Health Mycobacteriology, A Guide for the Level III Laboratory, U.S. Department of Health and Human Services, Public Health Service, Center for Disease Control, Atlanta, U.S.A., 1985, p. 31-55) according to the recommendation from Center for Disease Control and Prevention (CDC).

After disruption of cell wall of the tuberculosis bacterial cell, extraction and purification of DNA may be carried out by a general method for preparation of DNA in this field (phenol-chloroform extraction, ethanol precipitation method and the like, Rapid and simple method for purification of nucleic acids, J. Clin. Microbiol., 1990, March; 28 (3), 495-503, Boom R, Sol C J, Salimans M M, Jansen C L, Wertheim-van Dillen P M, van der Noordaa J), or by the method for precipitation using isopropanol and the like.

For the extraction and purification of DNA, as various types of kits for this purpose are available on the market, such kits may be utilized. For example, the extraction and purification of the DNA may be carried out using an ion-exchange resin type DNA extraction and purification kit Genomic-tip (QIAGEN GmbH) and the like.

Taking a case as an example where the isolated and cultured microbial cell from specimen is used as a sample, the procedure is shown as follows.

For example, colonies grown on the Ogawa's medium are collected and suspended in sterile distilled water, and then centrifuged to collect microbial cell, and then the microbial cell is resuspended in distilled water. Next, after the suspension of the microbial cell is autoclaved, the cells are subjected to disruption treatment (physical disruption using glass beads and the like); the disrupted microbial cell is further centrifuged to recover supernatant fluid. The DNA may be extracted and purified from the obtained supernatant fluid by the above-described method.

The method for detection of *M. avium* involved in the present invention includes a method that utilizes an oligonucleotide (the oligonucleotide of the present invention) which comprises a part or an entire of the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, or a part or an entire of the sequence complementary to the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, and which is capable of hybridizing with the nucleotide sequence for a *M. avium* gene as a primer and/or a probe (the method using the primer and/or the probe of the present invention).

For example,
(A) A method in which, using the oligonucleotide of the present invention as a primer, the nucleic acid amplification reaction is carried out, then the obtained primer extension product is detected;
(B) A method in which the oligonucleotide of the present invention is labeled with a labeling substance, and the labeled oligonucleotide is used as a labeled probe; and the like are included. Each method will be explained below.
(A) A method in which, using the oligonucleotide of the present invention as a primer, the nucleic acid amplification reaction is carried out, then the obtained primer extension product is detected In the method (A), the method by which the nucleic acid amplification reaction is carried out using the oligonucleotide of the present invention as a primer includes, for example, a method in which, using the primer of the present invention and using nucleic acid in a sample as a template, the nucleic acid amplification reaction by DNA polymerase and the like [for example, the polymerase chain reaction (PCR) method (JP-A-S60-281); LAMP (Loop-mediated Isothermal Amplification) method (Tsugunori Notomi et al., Nucleic Acid Res., 28, e63, 2000), ICAN™ (Isothermal and Chimeric primer-initiated Amplification of Nucleic acids) method (Rinsho Byori (Clinical Pathology), 51(11), 1061-1067, 2003, November), LCR (ligase chain reaction) method (JP-A-H04-211399), SDA (strand displacement amplification) method (JP-A-H08-19394)] is carried out to allow primer extension. And, by this method, the sequence of a specific region of the nucleotide sequence for a *M. avium* gene can be amplified, and thus *M. avium* can be detected by measuring the resulting primer extension product.

Among the above described methods for the nucleic acid amplification reaction, the PCR method is quoted as the most common method; and an example of the PCR method includes, for example, the real-time amplification detection method (see, for example, the description in U.S. Pat. No. 5,210,015 and U.S. Pat. No. 5,538,848). In addition, as an example of the detection method by the real-time amplification detection method includes, for example, the real-time PCR detection method is included.

An example of the real-time PCR detection method includes TaqMan™ real-time PCR method (see, for example, the description in U.S. Pat. No. 5,538,848), MGB Eclipse Probe System method (see, for example, the description in U.S. Pat. No. 5,801,155), Molecular Beacons Probe Technology method (see, for example, the description in U.S. Pat. No. 5,925,517), LUX Fluorogenic Primer method (Invitrogen Corp.), Quenching probe-PCR (QP) method (see, for example, the description in U.S. Pat. No. 6,492,121), and the like.

Specific examples of the primer of the present invention to be used in the nucleic acid amplification reaction such as the PCR are as described above.

In addition, preferable combinations of the forward primer and the reverse primer to be used in the nucleic acid amplification reaction include the combinations shown in the above described Table 1.

Among them, preferable combinations of the forward primer and the reverse primer include, for example, the combinations shown in the following Table 2.

In Table 2, for example, the combination of No. 1 indicates "a combination in which the forward primer is an oligonucleotide comprising a nucleotide sequence shown in SEQ ID NO:6, and the reverse primer is an oligonucleotide comprising a nucleotide sequence shown in SEQ ID NO:7".

Other reagents such as deoxyribonucleoside triphosphate (dATP, dCTP, dGTP, dTTP), DNA polymerase and the like to be used for the nucleic acid amplification reaction such as the real-time PCR using the above-described primers may be the same reagents as used commonly in this field; and the condition and the procedures and so on, except for the use of the primer and the probe of the present invention, may be carried out according to general protocol of the PCR method.

Method for detection of the primer extension product obtained by the nucleic acid amplification reaction may be the conventional procedures commonly conducted in this field, and there is no specific limitation.

The detection method includes, for example, various detection methods such as intercalator method; TaqMan™ real-time PCR method (see, for example, the description in U.S. Pat. No. 5,538,848); MGB Eclipse Probe System method (see, for example, the description in U.S. Pat. No. 5,801,155); Molecular Beacons Probe Technology method (see, for example, the description in U.S. Pat. No. 5,925,517); LUX Fluorogenic Primer method (Invitrogen Corp.); Quenching probe-PCR (QP) method (see, for example, the description in U.S. Pat. No. 6,492,121); a method in which, after the nucleic acid amplification reaction is carried out, the primer extension products obtained are subjected to electrophoresis, and detection is performed based on the results of the electrophoresis; a method in which a signal derived from the obtained primer extension product obtained by the nucleic acid amplification reaction carried out using a labeled primer is measured; and the like.

Among them, the commonly used method includes, for example, the following methods:
(A-1) Intercalator method;
(A-2) TaqMan™ real-time PCR method;
(A-3) The method in which, after the nucleic acid amplification reaction is carried out, the primer extension products obtained are subjected to electrophoresis, and the detection is performed based on the results of the electrophoresis; and

TABLE 2

| No. | Forward Primer | Reverse Primer | 番号 | Forward Primer | Reverse Primer |
|---|---|---|---|---|---|
| 1 | SEQ ID NO: 6 | SEQ ID NO: 7 | 25 | SEQ ID NO: 137 | SEQ ID NO: 138 |
| 2 | 10 | 11 | 26 | 139 | 140 |
| 3 | 12 | 13 | 27 | 141 | 142 |
| 4 | 14 | 15 | 28 | 143 | 144 |
| 5 | 16 | 17 | 29 | 145 | 146 |
| 6 | 22 | 23 | 30 | 147 | 148 |
| 7 | 57 | 58 | 31 | 149 | 150 |
| 8 | 59 | 60 | 32 | 151 | 152 |
| 9 | 61 | 62 | 33 | 153 | 154 |
| 10 | 63 | 64 | 34 | 155 | 156 |
| 11 | 65 | 66 | 35 | 157 | 158 |
| 12 | 67 | 68 | 36 | 159 | 160 |
| 13 | 69 | 70 | 37 | 161 | 162 |
| 14 | 71 | 72 | 38 | 163 | 164 |
| 15 | 75 | 76 | 39 | 165 | 166 |
| 16 | 77 | 78 | 40 | 167 | 168 |
| 17 | 79 | 80 | 41 | 169 | 170 |
| 18 | 81 | 82 | 42 | 171 | 172 |
| 19 | 83 | 84 | 43 | 173 | 174 |
| 20 | 85 | 86 | 44 | 175 | 176 |
| 21 | 87 | 88 | 44 | 177 | 178 |
| 22 | 89 | 90 | 45 | 179 | 180 |
| 23 | 91 | 92 | 46 | 181 | 182 |
| 24 | 93 | 94 | | | |

(A-4) The method in which the nucleic acid amplification reaction is carried out using a labeled primer and the signal derived from the obtained primer extension product is measured.

Each of these methods will be explained below.

(A-1) Intercalator Method

Conventional intercalator method can be utilized, in which the real-time PCR is carried out using known intercalator.

For example, a method in which, using the primer of the present invention and the intercalator, the real-time PCR is carried out through the use of conventional intercalator method, is included.

That is, the intercalator is a reagent capable of generating fluorescence by binding specifically to double-stranded DNA, and generates fluorescence when excitation light is irradiated. When the DNA is increased as the result of repeated amplification by the PCR, the intercalator is incorporated into the DNA accordingly. Because the amount of intercalator incorporated into the DNA will increase in proportion to the amount of amplification product generated, the amount of primer extension product can be determined by detecting the intensity derived from fluorescence originated from the intercalator.

In this regard, however, because the intercalator binds to the entire double-stranded DNA, melting curve analysis may be carried out, as need arise, by drawing melting curve based on the measurement results of fluorescence intensity. Namely, after carrying out the PCR, the temperature of the reaction solution of PCR is increased gradually, the fluorescence intensity derived from the intercalator is measured simultaneously. In the beginning, the PCR amplification product generates fluorescence because it takes double stranded form. However, when temperature of the reaction solution of PCR reaches to a certain temperature, the amplification products will dissociate to single strand form, and therefore, the fluorescence intensity derived from the intercalator decreases rapidly. The temperature at this occasion is melting temperature (Tm value), and is an intrinsic value for the sequence of primer extension product. Whether the peak of melting curve corresponds to the peak of an objective specific product or a non-specific product can be determined from this Tm value.

In this intercalator method, any electrophoretic procedure after the real-time PCR is not necessary, and therefore, this is an effective method in the field of clinical testing and the like where a rapid determination is required.

As to the intercalator to be used in the present invention, any type of intercalator usually used in this field, for example, SYBR™ Green I (Molecular Probes Inc.), ethidium bromide, fluorine and the like can be utilized.

An example of "the method for detection of *M. avium* through the use of intercalator method" involved in the present invention will be explained as follows:

Using the primer of the present invention and the intercalator (for example, SYBR™ Green I), and using a purified DNA sample isolated from a sample (test sample) to be detected for *M. avium* as a template, the real-time PCR is carried out with the use of a polymerase such as Taq DNA polymerase. And, by the method of decreasing the temperature described above, the fluorescence intensity derived from the intercalator (SYBR™ Green I) which intercalates with the primer extension products in correlation with the amplified amount is measured.

After that, by plotting the melting temperature of the primer extension product (double-stranded DNA) as horizontal axis and the first derivation (variation) of fluorescence intensity as vertical axis, melting curve is made. Using this, melting curve analysis of the primer extension product is carried out, and thereby detection of peak is examined. When a single peak is obtained, it can be determined that the sample is positive for *M. avium*.

Or otherwise, a dilution series of the purified DNA sample solution is prepared, and for each dilution series, the real-time PCR is carried out in the same way as described above.

After that, the melting curve is made up for each dilution series of the purified DNA sample solution used as a template in the real-time PCR by plotting the melting temperature of the primer extension product (double-stranded DNA) as horizontal axis and the first derivation (variation) of fluorescence intensity as vertical axis. And then, the melting curve analysis of the primer extension product and the peak detection analysis are performed. When the peaks with identical Tm value for each primer extension product of each dilution series is detected, it may be determined that the sample is positive for *M. avium* (that is, there exists *M. avium* strain or the gene thereof, and hereinafter, the same as above).

In addition, as a control, a DNA derived from *Mycobacterium* genus other than *M. avium* is extracted and purified by conventional procedure. The real-time PCR is carried out according to the same method as described above except for the use of this DNA as a template; and fluorescence intensity derived from the SYBR™ Green I is measured in the same way; and then the melting curve analysis may be carried out. In this case, as there is no nucleotide sequence derived from *M. avium* in the sample, no peak should appear in the melting curve analysis. To determine the presence of *M. avium* more definitive, it is desirable to conduct the above described control experiment in parallel.

In addition, based on the measurement value obtained by the method through the use of the intercalator method, a standard curve can also be made up according to the conventional procedure usually performed in the real-time PCR, and thereby, using the standard curve, the quantity (copy number) of genomic DNA of *M. avium* in a sample can be obtained.

The method of making the standard curve and the assay method of *M. avium* using it will be described later.

As an example of the method for detection of *M. avium* by the real-time PCR detection method using the intercalator involved in the present invention, taking a case where *M. avium* is detected using the above described "primer 12Fw_1" and "primer 12Rv_1" of the present invention, the method will be explained as follows.

At first, by known method, the purified DNA sample is obtained from the sample (test sample) for detection of *M. avium*.

On the side, using a DNA synthesizer, an oligonucleotide (12Fw_1) consisting of the nucleotide sequence shown in SEQ ID NO:14 and an oligonucleotide (12Rv_1) consisting of the nucleotide sequence shown in SEQ ID NO:15 are synthesized by the phosphoramidite method.

Using the synthesized 12Fw_1 as a forward primer and the 12Rv_1 as a reverse primer, the real-time PCR is carried out, for example, as follows.

That is, a 10 mM Tris-HCl buffer solution (pH 8.9) containing each 50 to 2000 nM of the primer 12Fw_1 and the primer 12Rv_1, about 5-100000 times dilution of the concentrate solution of intercalator [for example, SYBR™ Green I (product name of Molecular Probe Inc.)], 1.0 to 4.0 mM $MgCl_2$, KCl, BSA, sodium cholate, 0.005 to 0.2% TritonX-100, about 0.2 mM each of dATP, dCTP, dGTP and dTTP, and 10 to 80 U/ml of polymerase (for example, Taq DNA polymerase) is prepared, and used as a reaction solution for PCR. To aforementioned reaction solution for PCR, the purified DNA sample purified from a sample (test sample) for detection of *M. avium* is added, and used as a DNA sample for PCR. This sample for PCR is placed in each well of 96-well reaction plate, and the real-time PCR is carried out using real-time PCR detection equipment and the like. The reaction is repeated for 30 to 50 cycles, and at each cycle, the fluorescence derived from the SYBR™ Green I which intercalates in correlation with the amplification quantity of the primer extension products is measured.

After that, the melting curve is depicted by plotting the melting temperature of the primer extension product (double-stranded DNA) as horizontal axis and the first derivation (variation) of fluorescence intensity as vertical axis. Using this, the melting curve analysis of the primer extension product is carried out to detect the peak. When a single peak is obtained, it may be determined that the sample is positive for *M. avium*.

Or, a dilution series of the purified DNA sample solution is prepared, and for each dilution series, the real-time PCR is carried out in the same way as described above. After that, the melting curve is depicted by plotting the melting temperature of the primer extension product (double-stranded DNA) as horizontal axis and the first derivation (variation) of fluorescence intensity as vertical axis. And, the melting curve analysis of the primer extension product is performed to analyze the detected peak.

In this instance, as for the method of detection for *M. avium*, when the peaks with identical Tm value for each primer extension product of each dilution series are detected in the melting curve analysis, it may be determined that the sample is positive for *M. avium*.

In addition, as a control, a DNA derived from *Mycobacterium* genus other than *M. avium* is extracted and purified by conventional procedure; the real-time PCR is carried out according to the same method as described above except for the use of this DNA as a template; and fluorescence intensity derived from the SYBR™ Green I is measured in the same way; and then the melting curve analysis may be carried out. In this case, as there is no nucleotide sequence derived from *M. avium* in the sample, no peak should appear in the melting curve analysis. To determine the presence of *M. avium* more definitive, it is desirable to conduct the above described control experiment in parallel.

Further, by making a standard curve, number of the genomic DNA (the copy number) of *M. avium* in the sample can be obtained. In addition, as the number is proportional to number of *M. avium* cell, the number of *M. avium* in the sample (test sample) can also be determined.

(A-2) TaqMan™ real-time PCR method (TaqMan™ probe method)

The TaqMan™ real-time PCR method is a real-time PCR method using a probe in which the 5'-terminal thereof is labeled with a fluorescent dye (reporter) such as, for example, FAM, and the 3'-terminal thereof is labeled with a quencher dye such as, for example, TAMRA, and is a method capable of detecting a small amount of target DNA with high sensitivity and quantitatively (see, for example, the description in U.S. Pat. No. 5,538,848).

Specifically, using the primer of the present invention, and a labeled probe which is labeled with a reporter fluorescent dye on the 5'-terminal and with a quencher dye on the 3'-terminal of the probe of the present invention, the PCR is carried out with the nucleic acid in a sample as a template, and then the signal derived from labeling substance released from aforementioned labeled probe is detected.

The principle of the TaqMan™ real-time PCR method is as follows.

In this method, an oligonucleotide probe, which is labeled with a fluorescent dye (reporter) on the 5'-terminal thereof and with a quencher dye on the 3'-terminal thereof, and is capable of hybridizing with a specific region in the target gene, is used. In aforementioned probe, the fluorescence derived from the reporter is suppressed by the quencher dye under normal condition. Under the state where this fluorescent probe is hybridized completely with the target gene, the PCR is carried out from the outside thereof using a DNA polymerase. As the extension reaction by the DNA polymerase progresses, the fluorescent probe is hydrolyzed away from the 5'-terminal by the exonuclease activity of the DNA polymerase, and the released reporter dye generates the fluorescence. The real-time PCR method is a method for monitoring the intensity of this fluorescence in real time, and thereby, the initial amount of the template DNA can be quantified accurately.

For the forward primer and the reverse primer to be used for the TaqMan™ real-time PCR detection method involved in the present invention, the primer of the present invention is utilized. The preferable primer includes the primer to be used in the nucleic acid amplification reaction such as the above-described PCR method, and the preferable combination thereof are also as described above.

The probe to be used for labeling with a fluorescent dye (reporter) on the 5'-terminal thereof and a quencher dye on the 3'-terminal thereof, and which is used for the TaqMan™ real-time PCR detection method involved in the present invention, may be the probe of the present invention described above. In a practical sense, a probe comprising a nucleotide sequence of primer extension product which is anticipated to be obtained when the real-time PCR is carried out by the combined use of a selected forward primer and a reverse primer, or a probe comprising a nucleotide sequence designed further from such sequence may be used.

For example, the probe which is used when the real-time PCR is carried out using Primer 12Fw_1 and Primer 12Rv_1 includes an oligonucleotide comprising a part or an entire of the nucleotide sequence shown in SEQ ID NO:28 which is anticipated to be obtained when the real-time PCR is carried out.

The reporter fluorescent substance for labeling the 5'-terminal includes carboxyfluorescein (FAM), hexachlorofluorescein (HEX), tetrachlorofluorescein (TET), Cy5, VIC and the like, however, FAM is used commonly among them. The quencher dye for labeling the 3'-terminal includes fluorescent substance such as carboxytetramethyl-rhodamine (TAMRA), nonfluorescent substance such as Black Hole Quencher dye (for example, BHQ2), 4-((4-(dimethylamino) phenyl)azo)benzoic acid (DABCYL), however, TAMRA is used commonly among them.

Other reagents to be used for the real-time PCR detection method such as deoxyribonucleoside 3-phosphate (dATP, dCTP, dGTP, dTTP) and DNA polymerase may be the same reagents as usually used in the conventional real-time PCR, and the procedure of the real-time PCR may be carried out according to the customary protocol of the real-time PCR except for the use of the primer and the probe of the present invention.

As an example of the method for detection of *M. avium* by the TaqMan™ real-time PCR detection method involved in the present invention, taking a case where *M. avium* is detected using the primer "12Fw_1" and "12Rv_1" of the present invention as an example, the method would be explained as follows First, by a known method, purified DNA sample is obtained from a sample (test sample) to be detected for *M. avium*.

On the side, using a DNA synthesizer, an oligonucleotide (12Fw_1) consisting of a nucleotide sequence shown in SEQ ID NO:14 and an oligonucleotide (12Rv_1) consisting of a nucleotide sequence shown in SEQ ID NO:15 are synthesized by the phosphoramidite method.

In addition, from a nucleotide sequence shown in SEQ ID NO:28 which is anticipated to be amplified by the PCR using 12Fw_1 and 12Rv_1 as primers, a sequence for use as a probe is designed, and an oligonucleotide having this nucleotide sequence is synthesized. The 5'-terminal of this oligonucleotide is coupled with a reporter dye of FAM, and the 3'-terminal with a reporter quencher of TAMRA by the conventional procedures, and thereby a fluorescence labeled probe is obtained.

Using the above-prepared 12Fw_1 as a forward primer and the 12Rv_1 as a reverse primer, the real-time PCR is carried out, for example, as follows.

That is, a 10 mM Tris-HCl buffer solution (pH 8.9) containing each 0.1 to 2 μM, preferably each 1 μM of the primer 12Fw_1 and the primer 12Rv_1, 100 to 1000 nM fluorescence-labeled probe, 1.0 to 4.0 mM $MgCl_2$, KCl, BSA, sodium cholate, 0.005 to 0.2% TritonX-100, each about 0.2 mM of dATP, dCTP, dGTP and dTTP, and 10 to 80 unit/ml of Taq DNA polymerase is prepared, and used as a reaction solution for PCR. To 20 μl of this reaction solution for PCR, 1 ng of the purified DNA sample is added, and obtained a sample for PCR. This sample for PCR is placed in each well of a 96-well reaction plate, and the real-time PCR is carried out using appropriate real-time PCR detection equipment and the like. The reaction is repeated 30 to 50 cycles, and at every cycle, the fluorescence intensity derived from the reporter dye is measured.

In this instance, as for the method for detection of *M. avium*, when the fluorescence derived from the reporter dye is observed, it may be determined that the sample is positive for *M. avium*.

In addition, in the real-time PCR method, as a standard curve can be made up, the number of genomic DNA (copy number) of *M. avium* in the sample can be obtained. Further, as the number is proportional to the number of *M. avium* cell, the number of *M. avium* in the sample can also be determined.

The method for preparation of the standard curve may be performed according to the conventional procedure commonly carried out in the real-time PCR method. For example, using genomic DNA sample with known copy number derived from *M. avium* as a standard, a dilution series of concentration (copy number) of the DNA sample for PCR is prepared. After that, using each of the dilution series of the DNA sample for PCR, the real-time PCR is carried out according to the above described method, and the fluorescence intensity derived from the reporter dye is measured. For each concentration of the dilution series of the DNA sample for PCR, the measured value of the fluorescence intensity (Rn, y-axis) is plotted for each cycle number of PCR (x-axis) to make up an amplification curve. After that, an Rn part where the fluorescence intensity is amplified exponentially is selected, and a threshold line (Th) is drawn. The crossing point of the Th with an amplification curve of each DNA sample for PCR is defined as threshold cycle (Ct). After that, the Ct value (y-axis) is plotted for the logarithmic value of the copy number of each DNA sample used for PCR (x-axis), and an approximated curve obtained for each Ct may be used as a standard curve.

When the real-time PCR by the intercalator method is carried out, also, a standard curve can be made by the same way based on the obtained measurement value. For example, an amplification curve is made up by plotting the measurement value of the fluorescence intensity derived from the intercalator (Rn, y-axis) for each cycle number of PCR (x-axis). After that, Ct value is obtained by the same way as described above, and the Ct value (y-axis) is plotted for the logarithmic value of the copy number of each used DNA sample for PCR (x-axis), and an approximated curve obtained for each Ct may be used as a standard curve.

For the quantitative determination of the number of the genomic DNA (copy number) of *M. avium* in the specimen, at first, the DNA is isolated and purified from the specimen to be detected for *M. avium*, and the real-time PCR of the obtained DNA sample is carried out, and an amplification curve is made up in the same manner. The Ct value at the point where the obtained amplification curve crosses the Th obtained when the standard curve is made, is obtained. By fitting the Ct value to the standard curve, the quantity (copy number) of genomic DNA of *M. avium* in the sample can be obtained.

(A-3) The method in which, after the nucleic acid amplification reaction is carried out, the primer extension products obtained are subjected to electrophoresis, and the detection is performed based on the results of the electrophoresis This method includes, for example, "the method for detection of *M. avium* characterized by comprising the following steps:

(i) carrying out a nucleic acid amplification reaction using as a primer an oligonucleotide which comprises a part or an entire of the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, or a part or an entire of the sequence complementary to the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, and which is capable of hybridizing with the nucleotide sequence for a *M. avium* gene (the primer of the present invention), and using the nucleic acid in a sample as a template, and (ii) carrying out an electrophoresis of the primer extension product obtained in the above (i), and detecting the presence of *M. avium* based on the obtained result of the electrophoresis".

Method for determination of the presence of *M. avium* based on the results of electrophoresis includes, for example, (A-3-1) a method in which the determination is made by confirming a fraction of primer extension product having objective size (number of base pair); and (A-3-2) a method in which the determination is made by hybridization using labeled probe.

Specific examples of the nucleic acid amplification reaction are as described above.

Conditions, operational procedures and the like of the electrophoresis may be in accordance with those of the conventional method usually carried out in this field.

The methods of (A-3-1) and (A-3-2) will be described below.

(A-3-1) The method in which the determination is made by confirming a fraction of primer extension product having objective size (number of base pair)

For example, first, an appropriate combination of the forward primer and the reverse primer is selected from the primer of the present invention, and with the use of it, the nucleic acid amplification reaction such as PCR is carried out. And then, the primer extension product obtained is subjected to the electrophoresis. From the combination of the forward primer and the reverse primer used for the nucleic acid amplification reaction, a size (number of base pair) of the primer extension product which is anticipated to be amplified by the PCR is estimated in advance. And, confirmation whether the electrophoretic fraction obtained is relevant to the estimated size of amplification product may be performed by a conventional method. For example, a method in which, by such a way that the type of nucleic acid is visualized by staining the obtained electrophoretic fraction with ethidium bromide and the like, the primer extension product is confirmed based on its characteristic size, is included.

Specific example of the method for determination by the method of (A-3-1) includes, for example, a method in which, after carrying out the PCR using a combination of the forward primer and the reverse primer listed in the above-described Table 1, the primer extension product obtained is subjected to electrophoresis, and when an oligonucleotide having the nucleotide sequence shown in SEQ ID NO described in Table 1, which is anticipated to be amplified by the combination of the primers, or a fraction having a size corresponding to the number of the base pair is confirmed, it may be determined that the sample is positive for *M. avium*.

Specific example of the method of (A-3-1) will be shown collectively in the following Table 3.

That is, for example, the method of No. 1 in Table 3 is "a method in which, after carrying out the PCR using an oligonucleotide comprising a nucleotide sequence shown in SEQ ID NO:6 as a forward primer, and using an oligonucleotide comprising a nucleotide sequence shown in SEQ ID NO:7 as a reverse primer, the primer extension product obtained is subjected to electrophoresis, and when a fraction of 119 base pairs or a fraction of oligonucleotide having the nucleotide sequence shown in SEQ ID NO:24 is confirmed, the sample is determined to be positive".

TABLE 3

| | | Detection target | | |
|---|---|---|---|---|
| No. | Forward Primer | Reverse Primer | Number of base pair | Nucleotide sequence |
| 1 | SEQ ID NO: 6 | SEQ ID NO: 7 | 119 | SEQ ID NO: 24 |
| 2 | 8 | 9 | 134 | 25 |
| 3 | 10 | 11 | 137 | 26 |
| 4 | 12 | 13 | 155 | 27 |
| 5 | 14 | 15 | 150 | 28 |
| 6 | 16 | 17 | 184 | 29 |
| 7 | 18 | 19 | 132 | 30 |
| 8 | 20 | 21 | 182 | 31 |
| 9 | 22 | 23 | 199 | 32 |
| 10 | 43 | 44 | 146 | 101 |
| 11 | 45 | 46 | 166 | 102 |
| 12 | 47 | 48 | 200 | 103 |
| 13 | 49 | 50 | 140 | 104 |
| 14 | 51 | 52 | 150 | 105 |
| 15 | 53 | 54 | 137 | 106 |
| 16 | 55 | 56 | 173 | 107 |
| 17 | 57 | 58 | 190 | 108 |
| 18 | 59 | 60 | 152 | 109 |
| 19 | 61 | 62 | 177 | 110 |
| 20 | 63 | 64 | 159 | 111 |
| 21 | 65 | 66 | 162 | 112 |
| 22 | 67 | 68 | 114 | 113 |
| 23 | 69 | 70 | 199 | 114 |
| 24 | 71 | 72 | 220 | 115 |
| 25 | 73 | 74 | 142 | 116 |
| 26 | 75 | 76 | 134 | 117 |
| 27 | 77 | 78 | 191 | 118 |
| 28 | 79 | 80 | 174 | 119 |
| 29 | 81 | 82 | 201 | 120 |
| 30 | 83 | 84 | 143 | 121 |
| 31 | 85 | 86 | 164 | 122 |
| 32 | SEQ ID NO: 87 | SEQ ID NO: 88 | SEQ ID NO: 142 | SEQ ID NO: 123 |
| 33 | 89 | 90 | 117 | 124 |
| 34 | 91 | 92 | 141 | 125 |
| 35 | 93 | 94 | 106 | 126 |
| 36 | 95 | 96 | 170 | 127 |
| 37 | 97 | 98 | 189 | 128 |
| 38 | 99 | 100 | 169 | 129 |
| 39 | 137 | 138 | 154 | 183 |
| 40 | 139 | 140 | 176 | 184 |
| 41 | 141 | 142 | 164 | 185 |
| 42 | 143 | 144 | 157 | 186 |
| 43 | 145 | 146 | 152 | 187 |
| 44 | 147 | 148 | 193 | 188 |
| 45 | 149 | 150 | 178 | 189 |
| 46 | 151 | 152 | 139 | 190 |
| 47 | 153 | 154 | 101 | 191 |
| 48 | 155 | 156 | 131 | 192 |
| 49 | 157 | 158 | 112 | 193 |
| 50 | 159 | 160 | 163 | 194 |
| 51 | 161 | 162 | 163 | 195 |
| 52 | 163 | 164 | 159 | 196 |
| 53 | 165 | 166 | 198 | 197 |
| 54 | 167 | 168 | 152 | 198 |
| 55 | 169 | 170 | 164 | 199 |
| 56 | 171 | 172 | 114 | 200 |
| 57 | 173 | 174 | 105 | 201 |
| 58 | 175 | 176 | 122 | 202 |
| 59 | 177 | 178 | 106 | 203 |
| 60 | 179 | 180 | 145 | 204 |
| 61 | 181 | 182 | 110 | 205 |

Among methods mentioned above, methods No. 1, 3 to 6, 9, 17 to 24, 26 to 35, 39 to 61 are preferable.

Among them, the methods No. 39 to 61 are particularly preferable.

(A-3-2) The method in which the detection is made by hybridization using labeled probe The method includes, for example, a method in which the primer extension product obtained by the nucleic acid amplification reaction is subjected to electrophoresis, and then the electrophoretic fraction obtained is tested for hybridization with a labeled probe which is the probe of the present invention labeled with a labeling substance. When the presence of a fraction hybridizing with aforementioned labeled probe is confirmed by detecting a signal derived from aforementioned labeled probe, it may be determined that the sample is positive for *M. avium*.

Specific examples of the probe to be used and the labeling substance for use in labeling the probe, and the method for labeling the probe are as described above.

An example would be described as follows. That is, a method in which, after carrying out the PCR using a combination of the forward primer and the reverse primer listed in the above-described Table 1, the primer extension product obtained is subjected to electrophoresis. On the side, a labeled probe is prepared in advance by labeling an oligonucleotide with labeling substance, which is anticipated to be amplified by combined use of the forward primer and the reverse primer in the PCR, and which has a nucleotide sequence comprising a part or an entire of the nucleotide sequence shown in SEQ ID NO in Table 1. The electrophoretic fraction is tested for hybridization with aforementioned labeled probe, and when the presence of a fraction hybridizing with aforementioned labeled probe is confirmed by detecting signal derived from aforementioned labeled probe, it may be determined that the sample is positive for M. avium.

The specific examples of these preferable methods are shown collectively in the following Table 4.

For example, the method of No. 1 in Table 4 is "a method in which, after carrying out the PCR using an oligonucleotide comprising a nucleotide sequence shown in SEQ ID NO:6 as a forward primer, and using an oligonucleotide comprising a nucleotide sequence shown in SEQ ID NO:7 as a reverse primer, the primer extension product obtained is subjected to electrophoresis. After that, the fraction obtained is tested for hybridization with a labeled probe prepared by labeling an oligonucleotide which comprises a nucleotide sequence comprising a part or an entire of the sequence shown in SEQ ID NO:24, and when the presence of a fraction hybridizing with aforementioned labeled probe is confirmed by detecting a signal derived from aforementioned labeled probe, it is determined that the sample is positive".

TABLE 4

| No. | Forward Primer | Reverse Primer | Probe |
| --- | --- | --- | --- |
| 1 | SEQ ID NO: 6 | SEQ ID NO: 7 | SEQ ID NO: 24 |
| 2 | 8 | 9 | 25 |
| 3 | 10 | 11 | 26 |
| 4 | 12 | 13 | 27 |
| 5 | 14 | 15 | 28 |
| 6 | 16 | 17 | 29 |
| 7 | 18 | 19 | 30 |
| 8 | 20 | 21 | 31 |
| 9 | 22 | 23 | 32 |
| 10 | 43 | 44 | 101 |
| 11 | 45 | 46 | 102 |
| 12 | 47 | 48 | 103 |
| 13 | 49 | 50 | 104 |
| 14 | 51 | 52 | 105 |
| 15 | 53 | 54 | 106 |
| 16 | 55 | 56 | 107 |
| 17 | 57 | 58 | 108 |
| 18 | 59 | 60 | 109 |
| 19 | 61 | 62 | 110 |
| 20 | 63 | 64 | 111 |
| 21 | 65 | 66 | 112 |
| 22 | 67 | 68 | 113 |
| 23 | 69 | 70 | 114 |
| 24 | 71 | 72 | 115 |
| 25 | 73 | 74 | 116 |
| 26 | 75 | 76 | 117 |
| 27 | 77 | 78 | 118 |
| 28 | 79 | 80 | 119 |
| 29 | 81 | 82 | 120 |
| 30 | 83 | 84 | 121 |
| 31 | 85 | 86 | 122 |
| 32 | SEQ ID NO: 87 | SEQ ID NO: 88 | SEQ ID NO: 123 |
| 33 | 89 | 90 | 124 |
| 34 | 91 | 92 | 125 |
| 35 | 93 | 94 | 126 |
| 36 | 95 | 96 | 127 |
| 37 | 97 | 98 | 128 |
| 38 | 99 | 100 | 129 |
| 39 | 137 | 138 | 183 |
| 40 | 139 | 140 | 184 |
| 41 | 141 | 142 | 185 |
| 42 | 143 | 144 | 186 |
| 43 | 145 | 146 | 187 |
| 44 | 147 | 148 | 188 |
| 45 | 149 | 150 | 189 |
| 46 | 151 | 152 | 190 |
| 47 | 153 | 154 | 191 |
| 48 | 155 | 156 | 192 |
| 49 | 157 | 158 | 193 |
| 50 | 159 | 160 | 194 |
| 51 | 161 | 162 | 195 |
| 52 | 163 | 164 | 196 |
| 53 | 165 | 166 | 197 |
| 54 | 167 | 168 | 198 |
| 55 | 169 | 170 | 199 |
| 56 | 171 | 172 | 200 |
| 57 | 173 | 174 | 201 |
| 58 | 175 | 176 | 202 |
| 59 | 177 | 178 | 203 |
| 60 | 179 | 180 | 204 |
| 61 | 181 | 182 | 205 |

Among methods mentioned above, method No. 1, 3 to 6, 9, 17 to 24, 26 to 35, 39 to 61 are preferable.

Among them, the method No. 39 to 61 are particularly preferable.

The details of the method for detection of M. avium of the present invention by the method of (A-3) will be explained by taking, for example, a case (the method No. 5 of the above (A-3-1); see Table 3) as an example where, after the PCR is carried out using 12Fw_1 (SEQ ID NO:14) as a forward primer and 12Rv_1 as a reverse primer, and followed by electrophoresis, a fraction of the primer extension product having the objective base pair size is detected by the method for confirmation, as follows.

First, by a known method, purified DNA sample is obtained from a sample (test sample) to be detected for the presence of M. avium.

On the side, using a DNA synthesizer, 12Fw_1 (an oligonucleotide consisting of a sequence shown in SEQ ID NO:14) and 12Rv_1 (an oligonucleotide consisting of a nucleotide sequence shown in SEQ ID NO:15) are synthesized by the phosphoramidite method.

A 10 mM Tris-HCl buffer solution (pH 8.9) containing each 0.1 to 2 μM, preferably each 1 μM of the primer 12Fw_1 and the primer 12Rv_1, 1.0 to 4.0 mM $MgCl_2$, KCl, BSA, sodium cholate, 0.005 to 0.2% polyoxyethyleneoctylphenyl ether, each about 0.1 to 0.6 mM of dATP, dCTP, dGTP and dTTP, and 10 to 80 unit/ml of Taq DNA polymerase is prepared, and used as reaction solution for PCR.

The purified DNA is added to the reaction solution for PCR, and using this solution as a sample for PCR, 20 to 40 cycles of the PCR is carried out by the DNA Thermal Cycler. The obtained reaction solution after PCR is subjected to 1.5% agarose gel electrophoresis. Subsequently, after staining the gel with ethidium bromide, the fluorescence generated by UV ray irradiation is detected. Also, the molecular weight marker is electrophoresed in the same time in parallel with the reaction solution, and a length of the detected DNA fragment is calculated by comparing the relative mobility. In the PCR using the 12Fw_1 (having a sequence shown in SEQ ID NO:14) as a forward primer and the 12Rv_1 (having a sequence shown in SEQ ID NO:15) as a reverse primer, it is anticipated that the DNA fragment with 150 base pair (having a nucleotide sequence shown in SEQ ID NO:28) in the nucleotide sequence of *M. avium* could be replicated (see Table 3). Consequently, when a fluorescent band with the size of 150 base pair is confirmed, it may be determined that the sample is positive for *M. avium.*

In addition, in the nucleic acid amplification step of the present invention, a detection method through the use of RNA transcription product can be applied. For example, NASBA (nucleic acid sequence based amplification) method (JP-B-2650159), 3SR (self-sustained sequence replication) method (JP-B-H07-114718), TAS (transcription based amplification system) method (JP-A-H02-500565: WO 88/10315), TMA (transcription mediated amplification) method (JP-A-H11-46778) and the like are included. Among them, the constant temperature nucleic acid amplification methods utilizing a concerted mode of action of reverse transcriptase and RNA polymerase (reaction is carried out under such condition that allows the reverse transcriptase and the RNA polymerase act as concertedly) is a suitable method when the determination system is intended to be automated.

(A-4) The method in which the nucleic acid amplification reaction is carried out using a labeled primer and the signal derived from the obtained primer extension product is measured The method of (A-4) includes a method in which, using a labeled primer prepared by labeling the primer of the present invention by the above-described method, and using nucleic acid in a sample as a template, the nucleic acid amplification reaction such as PCR is carried out; and the detection/measurement of signal derived from the obtained primer extension product is carried out; and when the signal is detected, it may be determined that the sample is positive for *M. avium.*

The forward primer and the reverse primer to be used in this method include the ones which are used in the above-described PCR method, and the specific examples of preferable primers and preferable combination are also as described above.

In the above-described method, after the nucleic acid amplification reaction is carried out, free labeled primer is removed; and the signal derived from the primer extension product is measured; and when the signal is detected, it may be determined that the sample is positive for *M. avium.*

Method for removing free labeled primer includes a method in which, after the primer extension product in reaction mixture obtained by the nucleic acid amplification reaction is precipitated by conventional procedure of precipitating nucleic acid (ethanol precipitation method, a precipitation method using isopropanol and the like), the supernatant solution which contains non-precipitated free labeled primer is removed, and the like.

In addition, a method in which a reaction mixture obtained by nucleic acid amplification reaction is treated by a gel chromatography under appropriate condition, and thereby the primer extension product is separated from the free labeled primer, a method of separation by electrophoresis and the like are also included.

(B) A method in which the oligonucleotide of the present invention is labeled with a labeling substance, and the labeled oligonucleotide is used as a labeled probe Further, the method for detection of *M. avium* of the present invention includes a method in which, the oligonucleotide of the present invention is labeled with a labeling substance and used as a labeled probe, and aforementioned labeled probe is made to hybridize with the nucleic acid in the sample, and after removing the free labeled probe, the signal derived from the hybridized complex is detected.

Specifically, for example, the following methods are included.

(B-1) A detection method in which, using an oligonucleotide of the present invention which has been bound to a solid carrier as a trapping probe, the hybridization with nucleic acid in the sample is carried out, and thereby the nucleic acid derived from *M. avium* is immobilized on the solid phase (see, for example, the description in JP-A-S62-265999). In this case, the oligonucleotide of the present invention or the solid phase carrier may be labeled with a labeling substance.

(B-2) A method of so called "sandwich assay" in which, using an unlabeled trapping probe of (B-1) and the labeled probe which is the labeled probe of the present invention, the hybridization with nucleic acid in the sample is carried out to form a complex of trapping probe and nucleic acid derived from *M. avium* and labeled probe on the solid carrier, and then the signal derived from the labeled probe is measured (see, for example, the description in JP-A-S58-40099).

(B-3) A method in which, using a biotin-labeled probe of the present invention, the hybridization with nucleic acid in the sample is carried out, and after that, the nucleic acid derived from *M. avium* in the sample is trapped by avidin-bound carrier.

It should be noted that, as to the reagents to be used for the method for detection of *M. avium* of the present invention, any reagent usually used in this field which neither inhibit the stability of the coexisting reagents nor inhibit the nucleic acid amplification reaction such as PCR and hybridization reaction, for example, buffering agent, stabilizer, preservatives and the like can be used. And, concentration of the reagent may be selected as appropriate from the range of concentration usually used in this field.

Specific example of buffer solution includes all kinds of buffer solutions usually used for performing PCR and hybridization reaction, for example, Tris buffer, phosphate buffer, Veronal buffer, borate buffer, Good's buffer and the like; and the pH of the buffer solution is not particularly limited, but generally a range between pH 5-9 is preferable.

In addition, if necessary, nucleic acid synthetase (DNA polymerase, RNA polymerase, reverse transcriptase and the like), enzyme-specific substrate (dNTP, rNTP and the like), and additionally, double strand intercalator (ethidium bromide, SYBR™ Green and the like), and alternatively, substance for signal detection such as FAM and TAMRA may be used.

The reagent kit for detection of *M. avium* involved in the present invention includes "a reagent kit for detection of *M. avium* comprising an oligonucleotide as a primer (the primer of the present invention) and/or a probe (the probe of the present invention) which comprises a part or an entire of the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, or a part or an entire of the sequence complementary to the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, and which is capable of hybridizing with the nucleotide sequence for a *M. avium* gene".

Specific examples of the primer of the present invention and the probe of the present invention which constitute the above-described kit are as described hereinbefore in the explanation for the "the primer of the present invention" and "the probe of the present invention".

The primer of the present invention may be the one which is labeled with a labeling substance. Specific example of the labeling substance is as described above.

The kit comprised of the primer of the present invention also encompasses a composition comprising a pair of the forward primer and the reverse primer. Examples of the composition are shown collectively in the following Table 5.

For example, in Table 5 below, the kit No. 1 is "a kit comprising (a) an oligonucleotide primer which comprises a part or an entire of a nucleotide sequence shown in SEQ ID NO:6, or a part of an entire of the sequence complementary to a nucleotide sequence shown in SEQ ID NO:6, and which is capable of hybridizing with the nucleotide sequence for a *M. avium* gene, and (b) an oligonucleotide primer which comprises a part or an entire of a nucleotide sequence shown in SEQ ID NO:7, or a part of an entire of the sequence complementary to a nucleotide sequence shown in SEQ ID NO:7, and which is capable of hybridizing with the nucleotide sequence for a *M. avium* gene, as the constituent reagents".

TABLE 5

| No. | (a) | (b) |
|---|---|---|
| 1 | SEQ ID NO: 6 | SEQ ID NO: 7 |
| 2 | 8 | 9 |
| 3 | 10 | 11 |
| 4 | 12 | 13 |
| 5 | 14 | 15 |
| 6 | 16 | 17 |
| 7 | 18 | 19 |
| 8 | 20 | 21 |
| 9 | 22 | 23 |
| 10 | 43 | 44 |
| 11 | 45 | 46 |
| 12 | 47 | 48 |
| 13 | 49 | 50 |
| 14 | 51 | 52 |
| 15 | 53 | 54 |
| 16 | 55 | 56 |
| 17 | 57 | 58 |
| 18 | 59 | 60 |
| 19 | 61 | 62 |
| 20 | 63 | 64 |
| 21 | 65 | 66 |
| 22 | 67 | 68 |
| 23 | 69 | 70 |
| 24 | 71 | 72 |
| 25 | 73 | 74 |
| 26 | 75 | 76 |
| 27 | 77 | 78 |
| 28 | 79 | 80 |
| 29 | 81 | 82 |
| 30 | 83 | 84 |
| 31 | 85 | 86 |
| 32 | SEQ ID NO: 87 | SEQ ID NO: 88 |
| 33 | 89 | 90 |
| 34 | 91 | 92 |
| 35 | 93 | 94 |
| 36 | 95 | 96 |
| 37 | 97 | 98 |
| 38 | 99 | 100 |
| 39 | 137 | 138 |
| 40 | 139 | 140 |
| 41 | 141 | 142 |
| 42 | 143 | 144 |

TABLE 5-continued

| No. | (a) | (b) |
|---|---|---|
| 43 | 145 | 146 |
| 44 | 147 | 148 |
| 45 | 149 | 150 |
| 46 | 151 | 152 |
| 47 | 153 | 154 |
| 48 | 155 | 156 |
| 49 | 157 | 158 |
| 50 | 159 | 160 |
| 51 | 161 | 162 |
| 52 | 163 | 164 |
| 53 | 165 | 166 |
| 54 | 167 | 168 |
| 55 | 169 | 170 |
| 56 | 171 | 172 |
| 57 | 173 | 174 |
| 58 | 175 | 176 |
| 59 | 177 | 178 |
| 60 | 179 | 180 |
| 61 | 181 | 182 |

Further preferable primer and its combination are as described in the above exposition of the nucleic acid amplification method.

In addition, the above-described kits may comprise the oligonucleotide of the present invention which has been labeled with a labeling substance as a labeled probe.

Further, "a reagent kit for detection of *M. avium* comprising an oligonucleotide (the oligonucleotide of the present invention) as a probe which comprises a part or an entire of the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, or a part or an entire of the sequence complementary to the nucleotide sequence selected from SEQ ID NO:1, SEQ ID NO:2, SEQ ID NO:3, SEQ ID NO:4, SEQ ID NO:5, SEQ ID NO:37, SEQ ID NO:38, SEQ ID NO:39, SEQ ID NO:40, SEQ ID NO:41, SEQ ID NO:42, SEQ ID NO:130, SEQ ID NO:131, SEQ ID NO:132, SEQ ID NO:133, SEQ ID NO:134, SEQ ID NO:135 and SEQ ID NO:136, and which is capable of hybridizing with the nucleotide sequence for a *M. avium* gene", is included. Aforementioned probe may be a one which is labeled with a labeling substance.

Preferable embodiment and specific examples of constituent reagents composing these kits are as described above.

It should be noted that, the reagent kit for detection of *M. avium* of the present invention may comprise, for example, buffering agent, stabilizer, preservatives and the like which neither inhibit the stability of the coexisting reagents and the like nor inhibit the nucleic acid amplification reaction such as PCR and the hybridization reaction. In addition, the concentrations of the reagents may be selected as appropriate from the range of concentration usually used in this field.

Specific example of buffer solution includes all kinds of buffer solutions usually used for performing the PCR and the hybridization reaction, for example, Tris buffer, phosphate buffer, Veronal buffer, borate buffer, Good's buffer and the like, and the pH is not particularly limited, but generally a range between pH 5 to 9 is preferable.

In addition, if necessary, the nucleic acid synthetase (DNA polymerase, RNA polymerase, reverse transcriptase and the like), the substrate corresponding to the enzyme (dNTP, rNTP and the like), and additionally, the double strand intercalator (ethidium bromide, SYBR™ Green, ethidium bromide and the like), and alternatively, the substance for signal detection such as FAM and TAMRA, may be included in the kit.

Hereinafter, the present invention will be further explained in detail by referring to the following Examples, but the scope of the present invention should not be limited thereto.

It should be noted that, all bacteria used in Examples are clinical isolates, and their bacterial species has already been differentiated after culturing by colony morphology and conventional various types of biochemical tests on the cultured bacterium.

EXAMPLE

Example 1

Selection of Clone Derived from *M. Avium* Genome 1

(1) Preparation of DNA Sample Derived from *M. Avium*

Highly purified genomic DNA derived from *Mycobacterium avium* TMC16741 strain was obtained from Mycos Research LLC (USA).

Using 1 to 10 ng of obtained genomic DNA sample derived from *M. avium* as a material (template), and using Genomiphi V2 DNA Amplification Kit (produced by GE Healthcare Bio-Science AB), whole genome amplification reaction was carried out, and obtained 100 μg or more of amplification product. This amplification product was used as a "purified genomic DNA derived from *M. avium*" for the following experiments. It should be noted that, purity of the obtained genomic DNA derived from *M. avium* was confirmed to be good in absorbance measurement level.

In addition, this purified genomic DNA derived from *M. avium* was adjusted to give final concentration of 400 ng/μl (in 10 mM Tris-HCl buffer, pH 8.9), and used as "DNA sample derived from *M. avium*".

(2) Preparation of Whole Genome Shotgun Library

Using a 24 μg of the DNA sample derived from *M. avium* obtained in (1) above as a material, the Whole Genome Shotgun Library was prepared by the following method (a modified method from Whole Genome Shotgun method described in Science, 2001 Feb. 16; 291 (5507): 1304-1351, Venter et al.).

First, the DNA sample derived from *M. avium* was fragmented by treatment using a nebulizer (manufactured by Invitrogen Corp.) in the presence of 20% final concentration of glycerol under the pressure of 5 kPa to 9 kPa for about 10 minutes. By this treatment, a fraction (DNA fragment) with the objective size of 500 to 1,000 bp was recovered efficiently. The fraction obtained was purified using an extraction column manufactured by QIAGEN GmbH.

Subsequently, using the DNA Blunting Kit manufactured by Takara Bio Inc. and through the use of 5'→3' polymerase activity and 3'→5' exonuclease activity of T4 DNA Polymerase, terminal of the obtained DNA was blunted. This blunt-ended DNA was subjected to ligation reaction with blunt-ended pBSII $sk^+$ vector (Stratagene Corp.), and a recombinant DNA of pBSII $sk^+$ vector ($amp^r$), in which the DNA fragment was inserted thereto, was prepared.

Using *E. coli* JM109 Competent Cells manufactured by Takara Bio Inc., transformation of the *E. coli* JM109 Competent Cells was carried out using the above obtained recombinant DNA according to a protocol of the product. The transformant obtained was cultured in a plate on LB-agarose medium containing 100 μg/ml ampicillin, 0.2 mM IPTG and 40 μg/ml X-Gal. White colonies were picked up, and thus a library of the transformant in which "the recombinant DNA incorporated with the objective DNA fragment" has been inserted (Whole Genome Shotgun clone Library derived from *M. avium* genome) was obtained.

(3) Preparation of Microarray

Using the library of the transformant obtained in (2) above (Whole Genome Shotgun clone Library derived from *M. avium* genome), the PCR was carried out by the following method, and a probe material to be fixed on a slide glass was prepared.

Firstly, a 10 mM Tris-HCl buffer solution (pH 8.9) containing 1 μM each of primer M13 Primer M1 (Takara Bio Inc.) and primer M13 Primer RV (Takara Bio Inc.), 1.5 mM $MgCl_2$, 80 mM KCl, 500 μg/ml BSA, 0.1% sodium cholate, 0.1% Triton X-100 (product name of polyoxyethylene octylphenyl ether, Rohm and Haas Co.), 0.2 mM each of dATP, dCTP, dGTP and dTTP, and 40 unit/ml of Taq DNA polymerase (Nippon Gene Co.) was prepared and used as a reaction solution for PCR.

The DNA was purified from each transformant (Whole Genome Shotgun clone of genomic DNA derived from *M. avium*) obtained in (2) above according to the conventional procedure. This purified DNA (which would act as a template) was added to 20 μl of the reaction solution for PCR and suspended, and the suspension prepared was used as a sample for PCR. Using this sample for PCR, 30 cycles of PCR was carried out under the following reaction conditions using the DNA Thermal Cycler (DNA Engine PTC200, MJ Research Inc.).

Reaction conditions of the PCR:

Heat denaturation: 94° C. for 0.5 minutes;

Annealing: 55° C. for 1 minute;

Polymerization reaction: 75° C. for 0.5 minutes.

The PCR amplification product obtained was purified, and then mixed with immobilization buffer (final concentration: 3×SSC).

The final concentration of the PCR amplification product to be spotted was adjusted to give 300 ng/μl, and using a typing instrument (GTMAS Stamp II; Nippon Laser & Electronics) which was set at 55% in humidity in the instrument, the PCR product obtained above was spotted (the spot diameter: 150 to 250 μm) on a slide glass (CMT GAPS-II; Corning Inc.). The spotting-completed slide glass was transferred to a UV cross-linker (UV Stratalinker 1800; Stratagene Corp.), and UV light of 150 $mJ/cm^2$ was irradiated to fix the PCR amplification product (the objective DNA) on the slide glass, and thus the microarray (a microarray made from the Whole Genome Shotgun clone Library of genomic DNA derived from *M. avium,* 1,100 clones in total) was prepared.

(4) Fluorescent Dye Labeling of the Target Genomic DNA i) Fluorescent Dye Labeling of the Target Genomic DNA Fluorescent dye labeling of the target genomic DNA was carried out using BioPrime DNA labeling system (Invitrogen Corp.).

Firstly, after a 2 μg of purified genomic DNA derived from *M. avium* obtained in above (1) was mixed with 20 μl of random primer solution contained in the product of the labeling system kit, the mixture was subjected to heat denaturation treatment (95° C. for 5 minutes), and thereby, the sample solution was obtained. On the side, the genomic DNA was extracted and purified from *M. intracellulare* (ATCC 13950) by conventional procedure (genomic DNA for control); and the same treatment was carried out for the samples; and thus sample solutions were obtained.

Subsequently, to each sample solution obtained, 2 µl of 0.1 M DTT, 2 µl of the mixed solution of dATP/dCTP/dGTP (each 5 mM), 0.8 µl of 2.5 mM dTTP, 1.6 µl of 5 mM Ha-dUTP and 1 µl of Klenow enzyme (40 U/µl) were added and adjusted to give the total volume 50 µl with sterile deionized water, and then the extension reaction was carried out at 37° C. for 3 hours. An ultrafiltration column Microcon YM-30 (Millipore Co.) was set to the attached 1.5 ml tube and the above obtained reaction product was placed on the column and centrifuged at 14,000 rpm for 4 minutes. The concentrated solution was recovered in a microtube and dried thoroughly using a centrifugal vacuum drier (CentriVap concentrator; Labconco Co.).

The dried reaction product obtained above was added with 10 µl of 50 mM NaHCO$_3$ and mixed, then left for standing at ambient temperature for 2-3 minutes (hereinafter referred to as "solution of reaction product").

Separately, 1 mg of Cy5 (Amersham Biosciences K.K.) or Cy3 (Amersham Biosciences K.K.) was dissolved in 105 µl of DMSO (Cy-dye Solution Cy3, Cy-dye Solution Cy5). A 10 µl of the Cy-dye Solution Cy5 was added to the above-described solution of reaction product which was obtained with the use of genomic DNA fragment derived from *M. avium*, and incubated (under light shielding) at 40° C. for 60 minutes. Also, a 10 µl of the Cy-dye Solution Cy3 was added to the above-described solution of reaction product which was obtained with the use of genomic DNA for control (derived from *M. intracellulare*), and incubated (under light shielding) at 40° C. for 60 minutes.

Further, to the above-described each reaction product of post incubation, a 10 µl of 4 M NH$_2$OH (prepared just before use) was added and mixed, and was incubated (under light shielding) for 15 minutes to obtain the respective labeled product, namely, the labeled product of the Cy5-labeled genomic DNA derived from *M. avium*, and the labeled product of the Cy3-labeled genomic DNA derived from *M. intracellulare* were obtained.

An ultrafiltration column, Microcon YM-30 (Millipore Corp.), was set to the attached 1.5 ml tube, and then each of the above obtained labeled products of genomic DNA was placed on the column and centrifuged at 14,000 rpm for 4 minutes. The each concentrated solution was recovered in a microtube and dried thoroughly using a centrifugal vacuum drier (CentriVap concentrator; LABCONOCO Corp.).

ii) Fragmentation Process of the Labeled Products

To the labeled product of genomic DNA in dry state obtained in i) of (4) above, a 40 µl of a solution having a composition of the final concentrations of 0.04 M Tris-acetate (pH 8.1), 0.1 M potassium acetate, and 0.03 M magnesium acetate tetrahydrate was added and mixed in suspension. After that, the suspensions were heat-treated at 94° C. for 15 minutes, and the fragmentation products of each labeled genomic DNA with 100 to 300 nucleotides were obtained.

It should be noted that, from the result of investigation on the labeling efficiency (nucleotide/dye) using BcaBEST DNA Polymerase (Takara Bio Inc.) and rBst DNA Polymerase (EPICENTRE Biotechnologies), it was confirmed that, in the Cy3 labeling experiment, for about 28 nucleotides of the labeled product (DNA fragment) obtained using control genomic DNA derived from *M. intracellulare* as a material, one molecule of the dye has been incorporated; and in the Cy5 labeling experiment, for about 36 nucleotides of the labeled product (DNA fragment) obtained using genomic DNA derived from *M. avium* as a material, one molecule of the dye has been incorporated.

The obtained solutions of Cy3-labeled product and Cy5-labeled product were each placed onto an ultrafiltration column of Microcon YM-10 (Millipore Corp.), and centrifuged at 14,000 rpm for 4 minutes. After that, the concentrated solution was recovered in the same microtube, and then dried thoroughly using a centrifugal vacuum drier (CentriVap concentrator; LABCONCO Corp.). Subsequently, to this microtube, the following reagents were added and dissolved the labeled products in a dry form by mixing in suspension. Through the above-described procedure, a mixed solution of Cy3Cy5-labeled products comprising the fragmentation product of the Cy5-labeled product of the genomic DNA derived from *M. avium* and the fragmentation product of the Cy3-labeled product of the control genomic DNA derived from *M. intracellulare*, was obtained.

ArrayHyb Hybridization buffer (SIGMA-Aldrich Co.); 40 µl
Salmon sperm DNA (10 mg/ml); 0.5 µl
Formamide; 5 µl
Total 40 to 50 µl The obtained mixed solution of Cy3Cy5-labeled products were incubated at 95° C. for 5 minutes, and kept at 70° C. until use for hybridization.

(5) Microarray Hybridization

On the microarray of the Whole Genome Shotgun clone Library of genomic DNA derived from *M. avium* obtained in the above step (3), entire of the mixed solution of Cy3Cy5-labeled products obtained in the above described ii) of (4) was placed, and covered with a cover glass by keeping no air bubble remained inside. This microarray was set on a Hybri-cassette and placed on Kim Towel mat wetted with distilled water in a Tupperware and closed tightly, and was kept under light shielding at 65° C. for not less than 8 hours to allow hybridization. After hybridization, the microarray was soaked in a solution of 2×SSC containing 0.1% SDS together with cover glass at room temperature, and shook the microarray gently in the solution to remove the cover glass. Subsequently, after sequential washing with 1×SSC solution containing 0.03% SDS (at 60° C.) for 10 minutes, 0.2×SSC solution (at 42° C.) for 10 minutes and 0.05×SSC solution (at room temperature) for 10 minutes, the microarray was transferred quickly to a new dry rack, and dried immediately by centrifugation at 800 rpm for 5 minutes.

(6) Measurement of Fluorescence Intensity: from Signal Detection to Quantification Using a fluorescence readout scanner GenePix 4000B (Axon Instruments Inc.), the fluorescence intensity on the microarray obtained in the above (5) which received the microarray-hybridization treatment was measured. On this occasion, in order to analyze the results of competitive hybridization with Cy3-labeled product and Cy5-labeled product, detection of fluorescence was performed through 2 channels, namely through 2ch (Cy3, Cy5).

The quantification of fluorescence signal (fluorescence detection data) was performed using DNASIS™-Array (DNA chip expression image analysis software; Hitachi Software Engineering Co.), and according to the operational procedure of the software, automatic spot recognition, background calculation, and normalization of the fluorescence intensity ratio were carried out. In addition, by establishing a threshold limit line of reliability, and by avoiding the value lower than this line, a reliable normalized fluorescence intensity (ratio) was obtained.

Further, on the basis of the fluorescence intensity ratio of Cy3/Cy5 (Ratio) detected on the microarray, scatter chart (scatter plot) analysis was carried out according to the conventional procedure.

That is, when the fluorescence intensity ratio of Cy5 to Cy3 for a certain spot on the microarray is high, it indicates that the DNA fragment (PCR product) of the spot has been hybridized more strongly with the Cy5-labeled product, namely with the genomic DNA derived from *M. avium*. On the other hand, when the fluorescence intensity ratio of Cy5 to Cy3 for a certain spot on the microarray is low, it indicates that the DNA fragment of the spot has low specificity for the genomic DNA derived from *M. avium*, but cross reaction with the control genomic DNA derived from *M. intracellulare* took place (hybridized with the control genomic DNA derived from *M. intracellulare*).

By this method, the fluorescence intensity ratio for every spots of the microarray was calculated. And the spots having high fluorescence intensity and having high fluorescence intensity ratios of Cy5 to Cy3 were selected.

In the result, 24 clones which have hybridized more strongly with *M. avium* were selected as candidate clones.

(7) Determination of Nucleotide Sequence of the Candidate Clones

Next, for the selected 24 candidate clones selected in the above (6), their nucleotide sequences were determined by the method described below.

Namely, using Big Dye Terminator kit (Applied Biosystems Inc.), sequence analysis was carried out by the following procedure according to the protocol of the product.

Candidate DNA (candidate clone); 2 µl (100 ng)
M13 Primer M1; 1 µl (5 pmol)
Premix; 8 µl To the above mixture, sterile deionized water was added to give a total volume of 20 µl and then 30 cycles of the PCR under the following reaction conditions was carried out using the DNA Thermal Cycler (DNA Engine PTC200, MJ Research Inc.). 96° C. for 2 min→(96° C. for 10 sec→50° C. for 5 sec→60° C. for 4 min)×25→4° C.

The obtained PCR products were purified using a gel filtration column (QIAGEN GmbH), and then, using a sequencer (BaseStation, MJ Research Inc.), and according to the operation manual attached to the instrument, sequence (nucleotide sequence) mapping for all of nucleotide sequence of the candidate clones was completed.

The data obtained were searched over the database (NCBI BLAST and CHEMICAL ABSTRACT), and as the result, it was found that the nucleotide sequence of all 24 candidate clones were supposed to be unregistered new sequence on the data base.

Example 2

Specificity Evaluation of the Candidate Clone 13 for *M. Avium*

(1) Synthesis of the Primer of the Present Invention

Firstly, among the candidate 24 clones determined in the above-described Example 1, based on the result of sequence (nucleotide sequence) analysis of the candidate clone 13, from the candidate sequence 13, primer sequence for use in the PCR, namely, "5'-AAGGCTCATGGCTACCAAGTC-3'" (SEQ ID NO:14; hereinafter referred to as 12Fw_1), and "5'-TGGCCGAGTTCGTGATTCT-3'" (SEQ ID NO:15; hereinafter referred to as 12Rv_1) were designed using a primer design tool on the web, Primer 3 (Whitehead Institute for Biomedical Research).

It should be noted that, nucleotide sequence of the candidate clone 13 obtained from the result of sequence analysis is the one shown in SEQ ID NO:4. In addition, its clone ID number was numbered as R11_2d (named by the present inventor).

Next, the designed oligonucleotide was synthesized by the phosphoramidite method using ABI 392 DNA synthesizer. The synthetic procedure was carried out according to the operation manual provided by ABI, and the deprotection of various types of oligonucleotides was performed by heating aqueous ammonia solution of the oligonucleotide at 55° C. for overnight.

Subsequently, the synthesized oligonucleotide was purified by anion-exchange column chromatography using Pharmacia FPLC. This synthetic oligonucleotide was used as a primer.

(2) Preparation of DNA Sample

DNA sample from each bacterium shown below was each prepared by the method described below.

a: *Escherichia coli* (*E. coli*) (ATCC11775)
b: *Mycobacterium tuberculosis* (Human tubercle *bacillus*) (TMC102[H37Rv])
c: *Mycobacterium kansasii* (ATCC12478)
d: *Mycobacterium marinum* (ATCC927)
e: *Mycobacterium simiae* (ATCC25275)
f: *Mycobacterium scrofulaceum* (ATCC19981)
g: *Mycobacterium gordonae* (ATCC14470)
h: *Mycobacterium szulgai* (ATCC35799)
i: *M. avium* (TNC 16741)
j: *Mycobacterium intracellulare* (ATCC13950)
k: *Mycobacterium gastri* (ATCC15754)
l: *Mycobacterium xenopi* (ATCC19250)
m: *Mycobacterium nonchromogenicum* (ATCC19530)
n: *Mycobacterium terrae* (ATCC15755)
o: *Mycobacterium triviale* (ATCC23292)
p: *Mycobacterium fortuitum* (ATCC6841)
q: *Mycobacterium chelonei* (ATCC35752)
r: *Mycobacterium abscessus* (ATCC19977)
s: *Mycobacterium peregrinum* (ATCC14467)

Firstly, as to *Mycobacterium tuberculosis* and *M. avium*, each purified genomic DNA was obtained from Mycos Research, LLC, and used it as the purified DNA.

For the other bacteria, respective microbial strains were obtained from American Type Culture Collection (ATCC), and the DNA was extracted and purified by the following method. All bacteria used were clinical isolates, and their bacterial species have already been identified from colony morphology and by various conventional biochemical examinations and so on after cultivation.

That is, as to the bacteria of *Mycobacterium* genus, at first, the colonies grown on the Ogawa's medium were collected and suspended in purified water, and then autoclaved (at 120° C. under 2 atmospheric pressure for 20 minutes). Subsequently, the microbial cells were subjected to disruption treatment (physical disruption using 2 mm diameter of glass beads), followed by centrifugation to obtain the supernatant solution. From the obtained supernatant solution, the extraction and purification of DNA was carried out using ion-exchange resin type DNA extraction and purification kit, Genomic-tip (QIAGEN GmbH).

In addition, as to *E. coli*, according to the conventional procedure of DNA extraction from *E. coli*, the extraction and purification of the DNA was carried out.

Each of the purified DNA obtained was adjusted to give final concentration of 1 ng/µl (in 10 mM Tris-HCl buffer, pH 8.9), and used as DNA sample.

(3) Real-Time PCR

Using the 12Fw_1 as a forward primer and the 12Rv_1 as a reverse primer which were designed and synthesized in the above-described (1), the PCR was carried out as follows.

1) Preparation of Reaction Solution for PCR

A 10 mM Tris-HCl buffer solution (pH 8.9) containing 300 nM each of the primer 12Fw_1 and the primer 12Rv_1 obtained in the above-described (1), 30 times dilution of the undiluted solution (final concentration was 30000 times dilution of the undiluted solution) of SYBR™ Green 1 (product name of Molecular Probes Inc.), 1.5 mM MgCl$_2$, 80 mM KCl, 500 µg/ml BSA, 0.1% sodium cholate, 0.1% Triton X-100, 0.2 mM each of dATP, dCTP, dGTP and dTTP, and 40 unit/ml of Taq DNA polymerase (produced by Nippon Gene Co.) was prepared, and used as a reaction solution for PCR.

ii) Real-Time PCR

Using the DNA sample derived from Mycobacterium genus or derived from E. coli prepared in the above-described (2) as a template DNA of amplification target in the PCR, the real-time PCR by the intercalation method was carried out as follows, and quantitative monitoring of fluorescence was carried out simultaneously.

Firstly, to 20 µl of the reaction solution for PCR prepared in the above-described i) of (3), 1 µl (1 ng) of the DNA sample prepared in the above-described (2) was added and used as a sample for PCR.

This sample for PCR was placed in each well of a 96-well reaction plate (MicroAmp Optical 96-well Reaction Plate; produced by Applied Biosystems Japan Ltd.), and the real-time PCR was carried out using a specialized thermal cycler/detector for the TaqMan™ PCR (ABI 7500; produced by Applied Biosystems Japan Ltd.). That is, after keeping the temperature at 95° C. for 10 minutes, a reaction cycle composed of heating at 95° C. for 15 seconds and 60° C. for 1 minute was repeated for 40 cycles, and the fluorescence intensity derived from SYBR™ Green I which has intercalated in a correlation with the quantity of the primer extension products was measured.

It should be noted that, in the above-described real-time PCR using the forward primer 12Fw_1 and the reverse primer 12Rv_1, if there exist a nucleotide sequence of the candidate clone 13 in the DNA sample used as a template, it is anticipated that the DNA fragment (150 bp) with a sequence shown in SEQ ID NO:28 in the nucleotide sequence of the candidate clone 13 present in the genomic DNA of M. avium could be replicated, and fluorescence could be detected.

(4) Melting Curve Analysis

As to each amplification product for individual DNA sample, the melting curve was depicted by plotting the melting temperature of the primer extension product (double-stranded DNA) as horizontal axis and the first derivation (variation) of fluorescence intensity as vertical axis, and then detection of peak was examined.

(5) Result

Figure 1:
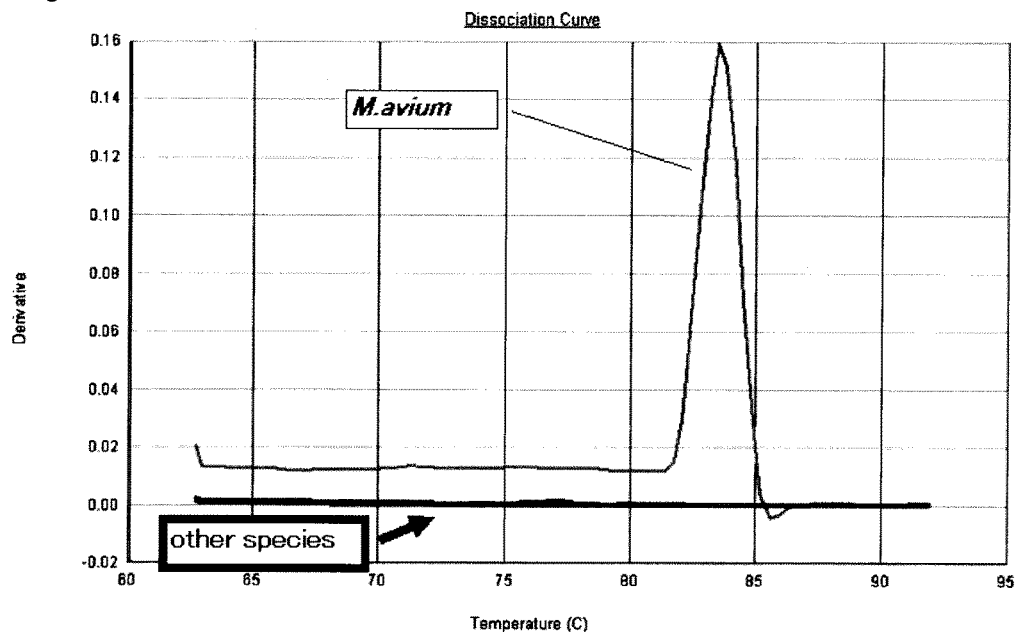
FIG. 1 shows the result of melting curve analysis obtained based on the results of real-time PCR by intercalator method obtained in Example 2 using primer 12Fw_1 and primer 12Rv_1 and using a DNA sample derived from *Mycobacterium* genus and a DNA sample derived from *Escherichia coli* as a template.

The results of the melting curve analysis obtained for each DNA sample were shown collectively in FIG. 1.

As is clear from the results shown in FIG. 1, as the result of the melting curve analysis of the nucleic acid which had been amplified using the primer 12Fw_1 and the 12Rv_1 of the present invention in the presence of SYBR Green I, only the case when the DNA sample derived from M. avium was used as a template, the fluorescence generated as the result of nucleic acid amplification was confirmed (FIG. 1: M. avium), and thus it could be determined as positive.

On the other hand, as is clear from FIG. 1, when the real-time PCR was carried out in the same way using the DNA derived from Mycobacterium genus except for M. avium and the DNA derived from bacteria of other genus like E. coli as a template, and using the same combination of primers, relevant fluorescence was not confirmed (FIG. 1: other species), and all cases were determined as negative.

Further, as is clear from FIG. 1, from the fact that a single clear peak was obtained as the result of the melting curve analysis when DNA sample derived from M. avium was used as a template, it can be understood that the detection method carried out is a detection method having quite high specificity for M. avium.

From the fact stated above, it turns out that, by the use of the oligonucleotide of the present invention as a primer for the PCR, M. avium can be detected specifically. In addition, since the detection by nucleic acid amplification such as PCR is expected to have high sensitivity, isolation of bacterium is not necessary, but the clinical specimen can be used directly for detection. Therefore, the detection of M. avium can be finished within a day at the longest, while it took several weeks for bacterial cultivation in the conventional detection method where detection is performed after bacterial cultivation.

Example 3

Evaluation of M. Avium Specificity of the Other Candidate Clone 1

(1) Synthesis of the Primer of the Present Invention

Among 24 candidate clones determined in Example 1, based on the result of sequence (nucleotide sequence) analysis of the candidate clone 08, the primer sequence for use in the PCR, namely, "5'-cattgtgcgctgcttatgac-3'" (SEQ ID NO:6; hereinafter referred to as 003Fw_1) and "5'-gaagtgaatcggccttgct-3'" (SEQ ID NO:7; hereinafter referred to as 003Rv_1) were designed from the candidate sequence 08 using a primer design tool on the web, Primer 3 (Whitehead Institute for Biomedical Research).

It should be noted that, the nucleotide sequence of the candidate clone 08 obtained from the result of sequence analysis is the nucleotide sequence shown in SEQ ID NO:1. In addition, the clone ID number was given as R07_12q.

Next, the designed oligonucleotide was synthesized and purified using the same equipment and by the same method as used in (1) of Example 2. This synthesized oligonucleotide was used as a primer of the present invention.

By the same method, the following primers were designed based on the nucleotide sequence of the other candidate clones.

(i) Based on the candidate sequence 09 (SEQ ID NO:2, clone ID number R07_7a), "5'-tgcaggtcgtgtagtcctc-3'" (SEQ ID NO:10; hereinafter referred to as "007Fw_1") and "5'-aaggtcgagttgcgcttg-3'" (SEQ ID NO:11; hereinafter referred to as "007Rv_1") were designed.

(ii) Based on the candidate sequence 12 (SEQ ID NO:3, clone ID number R11_12b), "5'-accagttgatgttgccttcc-3'" (SEQ ID NO:12; hereinafter referred to as "11Fw_1") and "5'-tctcgatcttcaccgtcagtt-3'" (SEQ ID NO:13; hereinafter referred to as "11Rv_1") were designed.

(iii) Based on the candidate sequence 13 (SEQ ID NO:4, clone ID number R11_2d), "5'-acctcaacccaggctacaga-3'" (SEQ ID NO:16: hereinafter referred to as "12Fw_4") and "5'-gaataagggaaagtgcatacga-3'" (SEQ ID NO:17; hereinafter referred to as "12Rv_4") were designed.

(iv) Based on the candidate sequence 22 (SEQ ID NO:5, clone ID number R16_6h), "5'-agggcgaacaaaacgatctac-3'" (SEQ ID NO:22; hereinafter referred to as "04Fw_1") and "5'-cccaaaacaacttctgcctct-3'" (SEQ ID NO:23; hereinafter referred to as "04Rv_1") were designed.

After that, designed each oligonucleotide was synthesized and purified by the same method as performed in (1) of Example 2. This synthesized oligonucleotide was used as a primer of the present invention.

(2) Preparation of DNA Sample

Using the same bacteria as used in (2) of Example 2, and by the same method as performed in (2) of Example 2, DNA sample was prepared.

(3) Real-Time PCR

The real-time PCR was carried out by the same method as performed in (3) of Example 2 except for using the primer which was designed and synthesized in the above-described (1) and using in combination as listed in the following Table 6.

TABLE 6

| | Forward Primer | | Reverse Primer | |
|---|---|---|---|---|
| No. | Name | SEQ ID NO: | Name | SEQ ID NO: |
| 1 | 003Fw_1 | 6 | 003Rv_1 | 7 |
| 2 | 007Fw_1 | 10 | 007Rv_1 | 11 |
| 3 | 11Fw_1 | 12 | 11Rv_1 | 13 |
| 4 | 12Fw_4 | 16 | 12Rv_4 | 17 |
| 5 | 04Fw_1 | 22 | 04Rv_1 | 23 |

(4) Melting Curve Analysis

By the same method as used in (4) of Example 2, melting curve of each amplification product for individual DNA sample was depicted by plotting the melting temperature of the primer extension product (double-stranded DNA) as horizontal axis and the first derivation (variation) of fluorescence intensity as vertical axis, and then detection of peak was examined.

(5) Result

As is the case with Example 2, as the result of the melting curve analysis of the nucleic acid which had been amplified using the primer of the present invention in the presence of SYBR Green 1, in any combination of the primers described in Table 6 is used, only the case when the real-time PCR was carried out using DNA sample derived from *M. avium* as a template, the fluorescence generated as the result of nucleic acid amplification was confirmed, and thus it could be determined as positive.

On the other hand, when the real-time PCR was carried out in the same way using the DNA derived from *Mycobacterium* genus except for *M. avium* and the DNA derived from bacteria of other genus like *E. coli* as a template, and using any combination of the same primers listed in Table 2, relevant fluorescence was not confirmed, and all cases were determined as negative.

Further, from the fact that a single clear peak was obtained as the result of the melting curve analysis when DNA sample derived from *M. avium* was used as a template, it turned out that the detection method carried out was a method having quite high specificity for *M. avium*.

From the results obtained above, it turned out that, by the use of the oligonucleotide of the present invention as a primer for the PCR, *M. avium* could be detected specifically. In addition, since the detection by nucleic acid amplification such as PCR is expected to have high sensitivity, isolation of bacterium is not necessary, but the clinical specimen can be used directly for detection. Therefore, the detection of *M. avium* can be finished within a day at the longest, while it took several weeks for bacterial cultivation in the conventional detection method where detection is performed after bacterial cultivation.

Example 4

Evaluation of *M. Avium* Specificity of the Other Candidate Clone 2

(1) Synthesis of the Primer of the Present Invention

Among 24 candidate clones determined in Example 1, based on the result of sequence (nucleotide sequence) analysis of the candidate clone 10, and from the candidate sequence 10, the primer sequence for use in the PCR, namely, "5'-caccggccaatccctaac-3'" (SEQ ID NO:67; hereinafter referred to as RE10Fw_02) and "5'-agcgcgatgcgtagt-tcc-3'" (SEQ ID NO:68; hereinafter referred to as RE10Rv_02) were designed using a primer design tool on the web, Primer 3 (Whitehead Institute for Biomedical Research).

It should be noted that, the nucleotide sequence of the candidate clone 10 obtained from the result of sequence analysis is the nucleotide sequence shown in SEQ ID NO:39.

Next, the designed oligonucleotides were synthesized and purified using the same equipment and by the same method as used in (1) of Example 2. These synthesized oligonucleotides were used as a primer of the present invention.

By the same method, the following primers were designed based on the nucleotide sequence of the other candidate clones.

Name of each candidate sequence (number), SEQ ID NO of nucleotide sequence of the candidate sequence, name of primer designed based on the candidate sequence (named by the present inventor, hereinafter the same as above) and SEQ ID NO of the nucleotide sequence thereof, combination of forward primer and reverse primer used in the upcoming PCR were shown collectively in Table 7. In addition, the clone ID number of each candidate sequence was shown in parentheses under the name of the candidate sequence.

TABLE 7

| Candidate sequence | | Designed primer | | | | |
|---|---|---|---|---|---|---|
| | | Combination | Forward primer | | Reverse Primer | |
| Name | SEQ ID NO: | number | Name | SEQ ID NO: | Name | SEQ ID NO: |
| Candidate sequence 01 (R03_10b) | 37 | 1 | RE01Fw_01 | 43 | RE01Rv_01 | 44 |
| | | 2 | RE01Fw_02 | 45 | RE01Rv_02 | 46 |
| | | 3 | RE01Fw_03 | 47 | RE01Rv_03 | 48 |
| | | 4 | RE01Fw_04 | 49 | RE01Rv_04 | 50 |

TABLE 7-continued

| Candidate sequence | | Combination number | Designed primer | | | |
|---|---|---|---|---|---|---|
| | | | Forward primer | | Reverse Primer | |
| Name | SEQ ID NO: | | Name | SEQ ID NO: | Name | SEQ ID NO: |
| | | 5 | RE01Fw_05 | 51 | RE01Rv_05 | 52 |
| | | 6 | RE01Fw_06 | 53 | RE01Rv_06 | 54 |
| Candidate sequence 04 (R05_11e) | 38 | 7 | RE04Fw_01 | 55 | RE04Rv_01 | 56 |
| | | 8 | RE04Fw_02 | 57 | RE04Rv_02 | 58 |
| | | 9 | RE04Fw_03 | 59 | RE04Rv_03 | 60 |
| | | 10 | RE04Fw_04 | 61 | RE04Rv_04 | 62 |
| | | 11 | RE04Fw_05 | 63 | RE04Rv_05 | 64 |
| | | 12 | RE04Fw_06 | 65 | RE04Rv_06 | 66 |
| Candidate sequence 10 (R08_10a) | 39 | 13 | RE10Fw_02 | 67 | RE10Rv_02 | 68 |
| | | 14 | RE10Fw_03 | 69 | RE10Rv_03 | 70 |
| | | 15 | RE10Fw_04 | 71 | RE10Rv_04 | 72 |
| | | 16 | RE10Fw_05 | 73 | RE10Rv_05 | 74 |
| Candidate sequence 11 (R08_11f) | 40 | 17 | RE11Fw_01 | 75 | RE11Rv_01 | 76 |
| | | 18 | RE11Fw_02 | 77 | RE11Rv_02 | 78 |
| | | 19 | RE11Fw_03 | 79 | RE11Rv_03 | 80 |
| | | 20 | RE11Fw_04 | 81 | RE11Rv_04 | 82 |
| Candidate sequence 23 (R16_8f) | 41 | 21 | RE23Fw_01 | 83 | RE23Rv_01 | 84 |
| | | 22 | RE23Fw_02 | 85 | RE23Rv_02 | 86 |
| | | 23 | RE23Fw_03 | 87 | RE23Rv_03 | 88 |
| | | 24 | RE23Fw_04 | 89 | RE23Rv_04 | 90 |
| | | 25 | RE23Fw_05 | 91 | RE23Rv_05 | 92 |
| Candidate sequence 24 (R01_2a) | 42 | 26 | RE24Fw_01 | 93 | RE24Rv_01 | 94 |
| | | 27 | RE24Fw_02 | 95 | RE24Rv_02 | 96 |
| | | 28 | RE24Fw_03 | 97 | RE24Rv_03 | 98 |
| | | 29 | RE24Fw_04 | 99 | RE24Rv_04 | 100 |

Next, the designed oligonucleotides were synthesized and purified by the same method as performed in (1) of Example 2. These synthesized oligonucleotides were used as a primer of the present invention.

(2) Preparation of DNA Sample

Using the same bacteria as used in (2) of Example 2 and by the same method, DNA samples were prepared.

(3) Real-Time PCR

The real-time PCR was carried out by the same method as performed in (3) of Example 2 except for using the primer prepared in the above-described (I) and using in combination as described in the above Table 7.

(4) Melting Curve Analysis

By the same method as described in (4) of Example 2, melting curve for each amplification product for individual DNA sample was depicted by plotting the melting temperature of the primer extension product (double-stranded DNA) as horizontal axis and the first derivation (variation) of fluorescence intensity as vertical axis, and then detection of peak was examined.

(5) Result

As is the case with Example 2, as the result of the melting curve analysis of the nucleic acid which had been amplified using the primer of the present invention in the presence of SYBR Green I, in any combination of the primers described in Table 7 is used, only the case when the real-time PCR was carried out using DNA sample derived from *M. avium* as a template, the fluorescence generated as the result of nucleic acid amplification was confirmed, and thus it could be determined as positive.

In particular, the real-time PCR by combined use of primers listed in the following Table 8 provided high specificity for *M. avium*.

TABLE 8

| | Forward Primer | | Reverse Primer | |
|---|---|---|---|---|
| No. | Name | SEQ ID NO: | Name | SEQ ID NO: |
| 1 | RE04Fw_02 | 57 | RE04Rv_02 | 58 |
| 2 | RE04Fw_03 | 59 | RE04Rv_03 | 60 |
| 3 | RE04Fw_04 | 61 | RE04Rv_04 | 62 |
| 4 | RE04Fw_05 | 63 | RE04Rv_05 | 64 |
| 5 | RE04Fw_06 | 65 | RE04Rv_06 | 66 |
| 6 | RE10Fw_02 | 67 | RE10Rv_02 | 68 |
| 7 | RE10Fw_03 | 69 | RE10Rv_03 | 70 |
| 8 | RE10Fw_04 | 71 | RE10Rv_04 | 72 |
| 9 | RE11Fw_01 | 75 | RE11Rv_01 | 76 |
| 10 | RE11Fw_02 | 77 | RE11Rv_02 | 78 |
| 11 | RE11Fw_03 | 79 | RE11Rv_03 | 80 |
| 12 | RE11Fw_04 | 81 | RE11Rv_04 | 82 |
| 13 | RE23Fw_01 | 83 | RE23Rv_01 | 84 |
| 14 | RE23Fw_02 | 85 | RE23Rv_02 | 86 |
| 15 | RE23Fw_03 | 87 | RE23Rv_03 | 88 |
| 16 | RE23Fw_04 | 89 | RE23Rv_04 | 90 |
| 17 | RE23Fw_05 | 91 | RE23Rv_05 | 92 |
| 18 | RE24Fw_01 | 93 | RE24Rv_01 | 94 |

It should be noted that, full-genome sequence of *M. avium* 104 (Kathleen L. Horan, et al., J. Clin. Microbiol., vol. 44, No. 3, pp. 783-789, 2006) has been published in DNA Data Bank of Japan (DDBJ) on the Web on Dec. 12, 2006 by National Institute of Genetics, Research Organization of Information and Systems, Inter-University Research Institute Corporation.

And so, when the nucleotide sequences of primer used in Example 4 and extension product obtained in Example 4 were compared with the full-genome sequence of *Mycobacterium avium* 104, it was found that there exists a site matching with the full-genome sequence of *M. avium* 104 particularly in the extension product of primer pairs shown in the following Table 9. From this finding, it was suggested that if the candidate sequence involved in the present invention is used as a target, detection of broad spectrum of *M. avium* species can be achieved.

TABLE 9

| | Forward Primer | | Reverse Primer | |
|---|---|---|---|---|
| No. | Name | SEQ ID NO: | Name | SEQ ID NO: |
| 1 | RE01Fw_01 | 43 | RE01Rv_01 | 44 |
| 2 | RE01Fw_02 | 45 | RE01Rv_02 | 46 |
| 3 | RE01Fw_03 | 47 | RE01Rv_03 | 48 |
| 4 | RE01Fw_04 | 49 | RE01Rv_04 | 50 |
| 5 | RE01Fw_05 | 51 | RE01Rv_05 | 52 |
| 6 | RE01Fw_06 | 53 | RE01Rv_06 | 54 |
| 7 | RE04Fw_02 | 57 | RE04Rv_02 | 58 |
| 8 | RE04Fw_03 | 59 | RE04Rv_03 | 60 |
| 9 | RE04Fw_04 | 61 | RE04Rv_04 | 62 |
| 10 | RE04Fw_05 | 63 | RE04Rv_05 | 64 |
| 11 | RE04Fw_06 | 65 | RE04Rv_06 | 66 |
| 12 | RE10Fw_02 | 67 | RE10Rv_02 | 68 |
| 13 | RE10Fw_03 | 69 | RE10Rv_03 | 70 |
| 14 | RE10Fw_04 | 71 | RE10Rv_04 | 72 |
| 15 | RE10Fw_05 | 73 | RE10Rv_05 | 74 |
| 16 | RE11Fw_01 | 75 | RE11Rv_01 | 76 |
| 17 | RE11Fw_02 | 77 | RE11Rv_02 | 78 |
| 18 | RE11Fw_03 | 79 | RE11Rv_03 | 80 |
| 19 | RE11Fw_04 | 81 | RE11Rv_04 | 82 |
| 20 | RE23Fw_01 | 83 | RE23Rv_01 | 84 |
| 21 | RE24Fw_03 | 97 | RE24Rv_03 | 98 |
| 22 | RE24Fw_04 | 99 | RE24Rv_04 | 100 |

From the results obtained above, it turned out that, by the use of the oligonucleotide of the present invention as a primer for the PCR, M. avium could be detected specifically. In addition, since the detection by nucleic acid amplification such as PCR is expected to have high sensitivity, isolation of bacterium is not necessary, but the clinical specimen can be used directly for detection. Therefore, the detection of M. avium can be finished within a day at the longest, while it took several weeks for bacterial cultivation in the conventional detection method where detection is performed after bacterial cultivation.

Example 5

Test for Minimum Detection Sensitivity 1

Using the real-time detection method, verification of detection sensitivity was carried out for a case where the candidate sequence 13 was targeted.
(1) Synthesis of the Primer of the Present Invention Using the same instrument and by the similar procedure as used in (1) of Example 2, oligonucleotides of 12Fw_1 and 12Rv_1 were synthesized. And these oligonucleotides were used as a primer.
(2) Preparation of DNA Sample Highly purified genomic DNA derived from M. avium was obtained from Mycos Research LLC (USA). The DNA was dissolved in 10 mM Tris-HCl buffer, and quantity of the DNA in the sample was determined by measuring absorbance thereof. The quantity of the DNA (copy number of the genome) in the sample was determined by comparing the obtained quantity of DNA with the measurement value obtained in the same way by measuring absorbance of the known concentration of genomic DNA of M. avium.

Subsequently, the DNA sample was diluted using 10 mM Tris-HCl buffer, pH 8.9 to a dilution series of $10^5$, $10^4$, $10^3$, $10^2$, 10, 5 and 2.5 copy/μl, and used as a DNA sample for PCR.
(3) Real-Time PCR
i) Preparation of Reaction Solution for PCR A 10 mM Tris-HCl buffer solution (pH 8.9) containing 300 nM each of the primer 12Fw_1 and the primer 12Rv_1 obtained in the above-described (1), 30 times dilution of the undiluted solution (final concentration was 30000 times dilution of the undiluted solution) of SYBR™ Green I (product name of Molecular Probes Inc.), 1.5 mM $MgCl_2$, 80 mM KCl, 500 ng/ml BSA, 0.1% sodium cholate, 0.1% Triton X-100, 0.2 mM each of dATP, dCTP, dGTP and dTTP, and 40 unit/rill of Taq DNA polymerase (produced by Nippon Gene Co.) was prepared, and used as a reaction solution for PCR.
ii) Real-Time PCR Using the DNA sample for PCR derived from M. avium prepared in the above-described (2) as a template DNA to be amplification target in the PCR, the real-time PCR by the intercalation method was carried out as follows, and quantitative monitoring of fluorescence was carried out simultaneously.

Firstly, to 20 μl of the reaction solution for PCR prepared in the above described i) of (3), 1 nl (1 ng) of the DNA sample for PCR prepared in the above described (2) was added and used as a sample for PCR.

This sample for PCR was placed in each well of a 96-well reaction plate (MicroAmp Optical 96-well Reaction Plate; produced by Applied Biosystems Japan Ltd.), and the real-time PCR was carried out using a specialized thermal cycler/detector for the TaqMan™ PCR (ABI 7500: produced by Applied Biosystems Japan Ltd.). That is, after keeping the temperature at 95° C. for 10 minutes, a reaction cycle composed of heating at 95° C. for 15 seconds and 60° C. for 1 minute was repeated for 40 cycles, and the fluorescence intensity derived from SYBR™ Green I which has intercalated in a correlation with the quantity of the primer extension products was measured.

It should be noted that, fluorescence intensity was measured by using a function of digitalizing relative fluorescent intensity ratio equipped to the thermal cycler used for the measurement, for each of the 96 well reaction plates used for the measurement.
(4) Result From experimental data obtained, a standard curve was made up according to conventional procedure commonly performed in the real-time PCR method.

Figure 2:
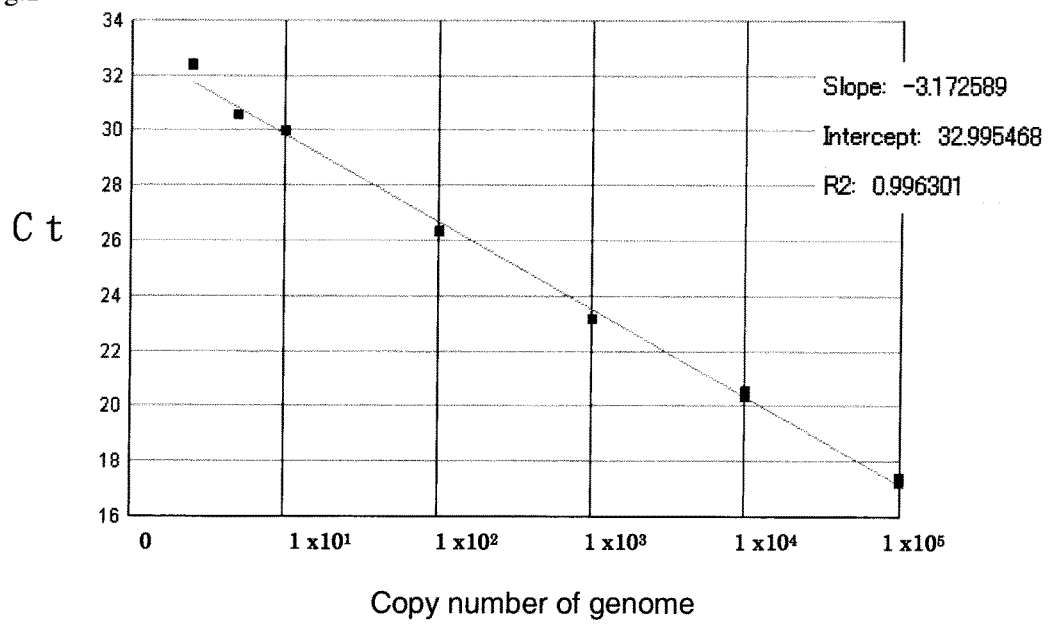
FIG. 2 shows the results of detection obtained by the real-time PCR in Example 5, which is a standard curve drawn by plotting Ct value (Y-axis) for the copy number of genome (X-axis, logarithmic scale) of each DNA sample for PCR.

That is, as to each concentration of the DNA samples for PCR, the fluorescence intensity derived from SYBR™ Green I (Rn, y-axis) was plotted for each cycle number of PCR (x-axis) to make up an amplification curve. After that, an Rn part where the fluorescence intensity amplified exponentially was selected, and a Threshold line (Th) was drawn. The crossing point of the Th with the fluorescence intensity derived from each DNA sample for PCR was defined as Threshold cycle (Ct). After that, the Ct value (y-axis) was plotted for the copy number of the genome of each used DNA sample for PCR (x-axis), and the approximated curve obtained for each Ct was used as a standard curve. The standard curve obtained is shown in FIG. 2.

$$y = -3.173x + 33.00$$

$$R^2 = 0.996$$

In consequence, from the fact that the fluorescence was detected by the real-time PCR, it turned out that M. avium can be detected by performing the real-time PCR using the oligonucleotide involved in the present invention as a primer.

In addition, it also turns out that, as the standard curve has become available, quantitative determination of M. avium is possible by the real-time PCR using the primer and the probe of the present invention. Further, it turns out from FIG. 2 that the real-time PCR method using the primer and the probe of the present invention can detect *M. avium* even under the condition where only 2.5 copies of the genomic DNA of *M. avium* are present as initial quantity.

Further, in the case where the real-time PCR method is applied, quantitative determination of the initial quantity of template DNA can be performed accurately, because the fluorescence intensity is monitored in real time, and therefore, the method is effective for the determination of *M. avium*.

Example 6

Using the real-time PCR detection method, and in a case where a new candidate sequence 13 (nucleotide sequence of candidate clone 13, consisting of nucleotide sequence shown in SEQ ID NO:4) is targeted, detection of *M. avium* was carried out.

(1) Synthesis of the Primer of the Present Invention for Detection of *M. Avium*

Using the same instrument and by the similar procedure as used in (1) of Example 2, oligonucleotides of 12Fw_1 (SEQ ID NO:14) and 12Rv_1 (SEQ ID NO:15) were synthesized and purified.

(2) Preparation of DNA Sample for PCR

The DNA sample prepared from bacterial cell of *M. avium* in (2) of Example 2 was used. Firstly, as to the aforementioned DNA sample, the quantity of the DNA in the sample was determined by measuring absorbance thereof. The quantity of DNA (copy number of the genome) in the sample was determined by comparing the obtained quantity of DNA with the measurement value obtained in the same way by measuring absorbance of the known concentration of genomic DNA of *M. avium*. The genomic DNA of $10^8$ copy/μl was obtained.

Subsequently, the DNA sample was diluted using 10 mM Tris-HCl buffer, pH 8.9 to a dilution series of $10^5$, $10^4$, $10^3$, $10^2$, 10, and 0 copy/μl, and used as a DNA samples for PCR.

(3) Real-Time PCR i) Preparation of Reaction Solution for PCR

A 10 mM Tris-HCl buffer solution (pH 8.9) containing 300 nM each of the primer 12Fw_1 and the primer 12Rv_1 obtained in the above-described (1), 30 times dilution of the undiluted solution (×0.3 concentrate; final concentration was 30000 times dilution of the undiluted solution) of SYBR™ Green I (product name of Molecular Probes Inc.), 1.5 mM MgCl$_2$, 80 mM KCl, 500 μg/ml BSA, 0.1% sodium cholate, 0.1% Triton X-100, 0.2 mM each of dATP, dCTP, dGTP and dTTP, and 40 unit/ml of Taq DNA polymerase (produced by Nippon Gene Co.) was prepared, and used as a reaction solution for PCR.

ii) Real-Time PCR

To 20 μl of the reaction solution for PCR prepared in the above described i) of (3), 1 μl (1 ng) of the DNA sample for PCR prepared in the above described (2) was added and used as a sample for PCR.

This sample for PCR was placed in each well of a 96-well reaction plate (MicroAmp Optical 96-well Reaction Plate; produced by Applied Biosystems Japan Ltd.), and the real-time PCR was carried out using a specialized thermal cycler/detector for the TaqMan™ PCR (ABI 7500; produced by Applied Biosystems Japan Ltd.). That is, after keeping the temperature at 95° C. for 10 minutes, a reaction cycle composed of heating at 95° C. for 15 seconds and 60° C. for 1 minute was repeated for 40 cycles, and the fluorescence intensity derived from SYBR™ Green I which has intercalated in a correlation with the quantity of the primer extension products was measured.

It should be noted that, fluorescence intensity was measured by using a function of the thermal cycler used for the measurement to digitalize relative fluorescent intensity ratio, for each of the 96 well reaction plates used for the measurement.

From the experimental data obtained, according to the conventional procedure commonly performed in the real-time PCR method, the fluorescence intensity derived from the reporter dye (Rn, y-axis) was plotted for each cycle number of PCR (x-axis) to make up an amplification curve for each DNA sample for PCR by the same method as (4) of Example 5.

The results were shown by solid line in FIG. 3.

In FIG. 3, each (1) to (6) show the following cases.

(1) A case where initial concentration of DNA in the DNA sample for PCR was set $10^5$ copies and the real-time PCR was carried out at a target of new candidate sequence 13.

(2) A case where initial concentration of DNA in the DNA sample for PCR was set $10^4$ copies and the real-time PCR was carried out at a target of new candidate sequence 13.

(3) A case where initial concentration of DNA in the DNA sample for PCR was set $10^3$ copies and the real-time PCR was carried out at a target of new candidate sequence 13.

(4) A case where initial concentration of DNA in the DNA sample for PCR was set $10^2$ copies and the real-time PCR was carried out at a target of new candidate sequence 13.

(5) A case where initial concentration of DNA in the DNA sample for PCR was set 10 copies and the real-time PCR was carried out at a target of new candidate sequence 13.

(6) A case where initial concentration of DNA in the DNA sample for PCR was set 0 copies and the real-time PCR was carried out at a target of new candidate sequence 13.

Comparative Example 1

Using known primer sequence, detection of *M. avium* was carried out at a target of gene region for 19 kDa protein of *M. avium*.

(1) Preparation of Known Primer for Detection of *M. Avium*

Based on the known primer MAV19K_F1 (sequence "5'-cggctgttcgagtggcaacaagtc-3'", SEQ ID NO:35) for detection of *M. avium* disclosed in JP-A-H11-69999 (Patent Literature 1, EP0887425), primer sequence "5'-ctgttcgagtg-gcaacaagtc-3" (hereinafter referred to as MAV19K_F1s; SEQ ID NO:33) was designed, and based on the MAV19K_R1 (sequence "5'-ccgtcgatgatgaccttggtccc-3'", SEQ ID NO:36), "5'-gtcgatgatgaccttggtcc-3'" (hereinafter referred to as MAV19K_R1s; SEQ ID NO:34) was designed.

Here, the reason why the MAV19K_F1 and the MAV19K_R1 which were the known primer for detection of *M. avium* disclosed in JP-A-H11-69999 were not used directly for the following PCR was as described below.

That is, the primer for use in the real-time PCR, the one having excessive length of nucleotide sequence is undesirable. However, at the time when the JP-A-H11-69999 was applied, the technology of the real-time PCR had not been established, and the primer MAV19K_F1 and the MAV19K_R1 disclosed in the JP-A-H11-69999 looked a little bit longer for use in the real-time PCR, and in addition, from their nucleotide sequence, it was anticipated that if these primers were used directly for the real-time PCR, annealing between primers might take place and form dimeric primers, and consequently, the possibility of raising a problem such as lowered PCR amplification efficiency would be high.

And so, to obtain a primer having convenient length for use in the real-time PCR, the present inventor has designed MAV19K_F1s which has a sequence deleted by 3 nucleotides "cgg" from 5' terminal of the primer MAV19K_F1 disclosed in JP-A-H11-69999, and MAV19K_R1s which has a sequence deleted by 2 nucleotides "cc" from 5' terminal of the MAV19K_R1.

Using the same instrument and by the similar procedure as used in (1) of Example 2, oligonucleotides of MAV19K_F1s (SEQ ID NO:33) and MAV19K_R1s (SEQ ID NO:34) were synthesized and purified.

(2) Preparation of DNA Sample for PCR

The same DNA sample as prepared in Example 6 was used.

(3) Real-Time PCR

The real-time PCR was carried out by the same method as used in (3) of Example 6 except for using MAV19K_F1s as a forward primer and MAV19K_R1s as a reverse primer.

From the experimental data obtained, according to the conventional procedure commonly performed in the real-time PCR method, the fluorescence intensity derived from the reporter dye (Rn, y-axis) was plotted for each cycle number of PCR (x-axis) to make up an amplification curve for each DNA sample for PCR by the same method as (4) of Example 5.

The results were shown by dotted line in FIG. 3.

In FIG. 3, each (7) to (12) show the following cases.

(7) A case where initial concentration of DNA in the DNA sample for PCR was set $10^5$ copies and the real-time PCR was carried out at a target of gene region for 19 kDa protein of M. avium.

(8) A case where initial concentration of DNA in the DNA sample for PCR was set $10^4$ copies and the real-time PCR was carried out at a target of gene region for 19 kDa protein of M. avium.

(9) A case where initial concentration of DNA in the DNA sample for PCR was set $10^3$ copies and the real-time PCR was carried out at a target of gene region for 19 kDa protein of M. avium.

(10) A case where initial concentration of DNA in the DNA sample for PCR was set $10^2$ copies and the real-time PCR was carried out at a target of gene region for 19 kDa protein of M. avium.

(11) A case where initial concentration of DNA in the DNA sample for PCR was set 10 copies and the real-time PCR was carried out at a target of gene region for 19 kDa protein of M. avium.

(12) A case where initial concentration of DNA in the DNA sample for PCR was set 0 copies and the real-time PCR was carried out at a target of gene region for 19 kDa protein of M. avium.

(4) Results

From the results obtained above, the detection method for M. avium by the real-time PCR was compared for a case where using the primer 12Fw_1 and the primer 12Rv_1 of the present invention and detection of M. avium was carried out at a target of new candidate sequence 13 (Example 6), and a case where using known primer disclosed in JP-A-H11-69999 and detection of M. avium was carried out at a target of a known sequence owned by M. avium (Comparative Example 1).

As is clear from the result of FIG. 3, it turns out that in any case of DNA samples (dilution series of $10^5$, $10^4$, $10^3$, $10^2$, 10, and 0 copy/μl), initial rise of amplification curve obtained in Example 6 is faster by about 4 cycles as compared with that obtained in Comparative Example 1. From this fact, it can be considered that the method of Example 6 is a detection method having about 10-20 times higher amplification efficiency as compared with the method of Comparative Example 1.

From the results obtained hereinbefore, it is clear that the detection method which uses the primer of the present invention and targets at a new candidate sequence 13 is obviously superior detection method in nucleic acid amplification efficiency as compared with the method which uses known primer described in JP-A-H11-69999 and targets at a known sequence.

Example 7

Selection of Clone Derived from M. Avium Genome 2

(1) Preparation of DNA Sample Derived from M. Avium

Firstly, Mycobacterium avium IID 585 which is a type strain of M. avium (subdivided from Japanese Society for Bacteriology: come from Pathogenic Microbes Repository Unit, International Research Center for Infectious Diseases, Institute of Medical Science, The University of Tokyo, National University Corporation) was suspended in purified water and autoclaved (at 120° C. under 2 atmospheric pressure for 20 minutes). Subsequently, the microbial cells were subjected to disruption treatment (physical disruption using 2 mm diameter of glass beads), followed by centrifugation to obtain the supernatant solution. From the obtained supernatant solution, the extraction and purification of DNA was carried out using ion-exchange resin type DNA extraction and purification kit, Genomic-tip (QIAGEN GmbH), and obtained purified genomic DNA derived from M. avium (Mycobacterium avium IID 585).

The purified genomic DNA derived from M. avium obtained was adjusted to give final concentration of 400 ng/μl (in 10 mM Tris-HCl buffer, pH 8.9), and used as "DNA sample derived from M. avium".

(2) Preparation of Whole Genome Shotgun Library and Microarray

Using a 24 μg of the DNA sample derived from M. avium obtained in (1) above as a material, the Whole Genome Shotgun Library and microarray (a microarray of the Whole Genome Shotgun Library of the genome derived from M. avium, total 1000 clones) were prepared using the same reagents and by the same method as used in the above-described (2) to (3) of Example 1.

(3) Fluorescent Dye Labeling of the Target Genomic DNA i) Fluorescent Dye Labeling of the Target Genomic DNA Fluorescent dye labeling of the target genomic DNA was carried out using BioPrime DNA labeling system (Invitrogen Corp.)

Firstly, after a 2 μg of purified genomic DNA derived from M. avium obtained in above (1) was mixed with 20 μl of random primer solution contained in the product of the labeling system kit, the mixture was subjected to heat denaturation treatment (95° C. for 5 minutes), and thereby, the sample solution was obtained. On the side, the genomic DNA was extracted and purified from M. intracellulare (ATCC 13950) by conventional procedure (genomic DNA for control); and the same treatment was carried out for the samples; and thus sample solutions were obtained.

Subsequently, to each sample solution obtained, 2 μl of 0.1 M DTT, 2 μl of the mixed solution of dATP/dCTP/dGTP (each 5 mM), 0.8 μl of 2.5 mM dTTP, 1.6 μl of 5 mM Ha-dUTP and 1 μl of Klenow enzyme (40 U/μl) were added and adjusted to give the total volume 50 μl with sterile deionized water, and then the extension reaction was carried out at 37° C. for 3 hours. An ultrafiltration column Microcon YM-30 (Millipore Co.) was set to the attached 1.5 ml tube and the above obtained reaction product was placed on the column and centrifuged at 14,000 rpm for 4 minutes. The concentrated solution was recovered in a microtube and dried thoroughly using a centrifugal vacuum drier (CentriVap concentrator; LABCONCO Co.).

The dried reaction product obtained above was added with 10 μA of 50 mM NaHCO$_3$ and mixed, then left for standing at ambient temperature for 2 to 3 minutes (hereinafter referred to as "solution of reaction product").

Separately, 1 mg of Alexa647 (Invitrogen Corp.) or Alexa555 (Invitrogen Corp.) was dissolved in 105 μl of DMSO (dye Solution Alexa647, dye Solution Alexa555). A 10 μl of the dye Solution Alexa647 was added to the above-described solution of reaction product which was obtained with the use of genomic DNA derived from M. avium, and incubated (under light shielding) at 40° C. for 60 minutes. Also, a 10 μl of the dye Solution Alexa555 was added to the above-described solution of reaction product which was obtained with the use of genomic DNA for control (derived from M. intracellulare), and incubated (under light shielding) at 40° C. for 60 minutes.

Further, to the above-described each reaction product of post incubation, a 10 μl of 4 M NH$_2$OH (prepared just before use) was added and mixed, and was incubated (under light shielding) for 15 minutes to obtain the respective labeled product, namely, the labeled product of the Alexa647-labeled genomic DNA derived from M. avium, and the labeled product of the Alexa555-labeled genomic DNA derived from M. intracellulare were obtained.

An ultrafiltration column, Microcon YM-30 (Millipore Corp.), was set to the attached 1.5 ml tube, and then each of the above obtained labeled products of genomic DNA was placed on the column and centrifuged at 14,000 rpm for 4 minutes. The each concentrated solution was recovered in a microtube and dried thoroughly using a centrifugal vacuum drier (CentriVap concentrator; LABCONCO Corp.).

ii) Fragmentation Process of the Labeled Products

To the labeled product of genomic DNA in dry state obtained in i) of (3) above, a 40 μl of a solution having a composition of the final concentrations of 0.04 M Tris-acetate (pH 8.1), 0.1 M potassium acetate, and 0.03 M magnesium acetate tetrahydrate was added and mixed in suspension. After that, the suspensions were heat-treated at 94° C. for 15 minutes, and the fragmentation products of each labeled genomic DNA with 100 to 300 nucleotides were obtained.

It should be noted that, from the result of investigation on the labeling efficiency (nucleotide/dye) using indirect labeling method, it was confirmed that, with respect to Alexa647, 1 molecule of the dye has been incorporated for about 100-200 nucleotides. In addition, with respect to Alexa555, it was confirmed that 1 molecule of the dye has been incorporated for about 150 nucleotides.

The obtained solutions of Alexa647-labeled product and Alexa555-labeled product were each placed onto an ultrafiltration column of Microcon YM-10 (Millipore Corp.), and centrifuged at 14,000 rpm for 4 minutes. After that, the concentrated solution was recovered in the same microtube, and then dried thoroughly using a centrifugal vacuum drier (CentriVap concentrator; LABCONCO Corp.). Subsequently, to this microtube, the following reagents were added and dissolved the labeled products in a dry form by mixing in suspension. Through the above-described procedure, a mixed solution of Alexa555Alexa647-labeled products comprising the fragmentation product of the Alexa647-labeled product of the genomic DNA derived from M. avium and the fragmentation product of the Alexa555-labeled product of the control genomic DNA derived from M. intracellulare, was obtained.

ArrayHyb Hybridization buffer (SIGMA-Aldrich Co.); 40 μl

Salmon sperm DNA (10 mg/ml); 0.5 μl
Formamide; 5 μl
Total 40 to 50 μl

The obtained mixed solution of Alexa555Alexa647-labeled products were incubated at 95° C. for 5 minutes, and kept at 70° C. until use for hybridization.

(4) Microarray Hybridization

By the same method as described above in (5) of Example 1, except for using a mixed solution of Alexa555Alexa647-labeled products obtained in the above step (3), competitive hybridization of Alexa555-labeled product and Alexa647-labeled product for the microarray of Whole Genome Shotgun clone Library of genomic DNA derived from M. avium obtained in the above-described (2) was carried out.

(5) Measurement of Fluorescence Intensity: from Signal Detection to Quantification Using a fluorescence readout scanner GenePix 4000B (Axon Instruments Inc.), the fluorescence intensity on the microarray obtained in the above (4) which received the microarray-hybridization treatment was measured. On this occasion, in order to analyze the results of competitive hybridization with Alexa555-labeled product and Alexa647-labeled product, detection of fluorescence was performed through 2 channels, namely through 2ch (Alexa555, Alexa647).

In addition, Using the same instrument as used in the above (6) of Example 1, the quantification of fluorescence signal (fluorescence detection data) was carried out.

Further, on the basis of the fluorescence intensity ratio (Ratio) of Alexa555/Alexa647 detected on the microarray, scatter chart (scatter plot) analysis was carried out according to the conventional procedure.

In this case, that is, when the fluorescence intensity ratio of Alexa647 to Alexa555 for a certain spot on the microarray is high, it indicates that the DNA fragment (PCR product) of the spot has been hybridized more strongly with the Alexa647-labeled product, namely with the genomic DNA derived from M. aviume. On the other hand, when the fluorescence intensity ratio of Alexa647 to Alexa555 for a certain spot on the microarray is low, it indicates that the DNA fragment of the spot has low specificity for the genomic DNA derived from M. avium, but cross reaction with the control genomic DNA derived from M. intracellulare has taken place (hybridized with the control genomic DNA derived from M. intracellulare).

By this method, the fluorescence intensity ratio for every spots on the microarray was calculated. And the spots having high fluorescence intensity and having high fluorescence intensity ratio of Alexa647 to Alexa555 were selected.

(6) Secondary Detection Using the Other M. Avium Strain

Using various strains of M. avium species (subdivided from Japanese Society for Bacteriology) described in Table 10 below, "DNA sample derived from M. avium" was prepared from each strain by the same method as described in (1) above.

TABLE 10

| Species | Strain | Origin |
| --- | --- | --- |
| M. avium | TMC16741 | Mycos Research, LLC |
| M. avium | IID 585 (type) | Institute of Medical Science, The University of Tokyo |
| M. avium | RIMD 1312004 | Research Institute for Micrbial Diseases, Osaka University |
| M. avium | GTC M3234 | Gifu University School of Medicine |
| M. avium | GTC M1989-6 | Gifu University School of Medicine |
| M. avium | GTC 01937 | The Chemo-Sero Therapeutic Research Institute |
| M. avium | GTC M3276 | Gifu University School of Medicine |
| M. avium | GTC M91-126 | Gifu University School of Medicine |
| M. avium | GTC M91-130 | Gifu University School of Medicine |
| M. avium | GTC M1988-37 | Gifu University School of Medicine |

Next, labeled products of genomic DNA derived from each M. avium strain which was labeled with Alexa647 by the same method as performed in the above i)-ii) of (3), was obtained, and subsequently fragmentation products thereof were obtained.

In addition, labeled product of genomic DNA derived from M. intracellulare which was labeled with Alexa555 by the same method as performed in the above i)-ii) of (3), was obtained, and subsequently fragmentation product thereof was obtained.

Subsequently, by the same method as performed in the above i)-ii) of (3), a mixed solution of Alexa555Alexa647-labeled product comprising a fragmentation product of Alexa647-labeled product of genomic DNA derived from each M. avium strain and a fragmentation product of Alexa555-labeled product of control genomic DNA derived from M. intracellulare was obtained.

Using obtained each mixed solution of Alexa555Alexa647-labeled product, competitive hybridization of Alexa555-labeled product and Alexa647-labeled product for the microarray of Whole Genome Shotgun clone of genome derived from M. avium obtained in the above-described (2) of Example 7, and measurement of fluorescence intensity were carried out by the same way as described in the above (4) to (5).

Further, by the same method as described in (5) above, and based on the fluorescence intensity ratio (Ratio) of Alexa555/Alexa647 detected on the microarray, scatter chart (scatter plot) analysis was carried out according to the conventional procedure.

On the basis of obtained results of the analysis, and by the same method as described in (5) above, the fluorescence intensity ratio for every spots on the microarray was calculated. And the spots having high fluorescence intensity and having high fluorescence intensity ratio of Alexa647 to Alexa555 were selected.

(7) Selection of Candidate Clone

On the basis of the above-described results, as a guide to select candidates as consensus sequence, the spots which hybridized with these M. avium strains in the detection of above-described (6), and which did not hybridize with M. intracellulare in the detection of above-described (5) were selected from the Whole Genome Shotgun clone of genomic DNA derived from M. avium on the microarray. As the result, 7 spots (candidate clones) were selected.

(8) Determination of Nucleotide Sequence of Candidate Clones

Next, for 7 candidate clones selected in the above-described (7), sequence analysis was carried out by the same method as described in (7) of Example 1, and the nucleotide sequence of each clone was determined.

Name of candidate clone, clone ID number, and SEQ ID NO of the nucleotide sequence were shown collectively in the following Table 11.

TABLE 11

| Candidate sequence | | |
| --- | --- | --- |
| Name | Clone ID number | SEQ ID NO: |
| Candidate sequence A | m05_3b | 130 |
| Candidate sequence B | m11_6b | 131 |
| Candidate sequence C | m01_11e | 132 |
| Candidate sequence D | m01_12c | 133 |
| Candidate sequence E | m05_2d | 134 |
| Candidate sequence F | m07_3b | 135 |
| Candidate sequence G | m08_3e | 136 |

Example 8

Evaluation of Interspecific Conservation of Candidate Sequence D Among M. avium Strains 1

(1) Synthesis of the Primer of the Present Invention

Among candidate clones determined in (8) of Example 7, based on the result of sequence (nucleotide sequence) analysis of candidate clone D, the primer sequence for use in the PCR, namely, "5'-AGTGGGCAACAATCCAAGAG-3" (SEQ ID NO:159; hereinafter referred to as "Mac_12 Fw01") and "5'-CCCGACACAACGAGGTTT-3" (SEQ ID NO:160; hereinafter referred to as "Mac_12 Rv01") were designed from the candidate sequence D using a primer design tool on the web, Primer 3 (Whitehead Institute for Biomedical Research).

Next, the designed oligonucleotide was synthesized by the phosphoramidite method using ABI 392 DNA synthesizer. The synthetic procedure was carried out according to the operation manual provided by ABI, and the deprotection of various types of oligonucleotides was performed by heating aqueous ammonia solution of the oligonucleotide at 55° C. for overnight.

Subsequently, the synthesized oligonucleotide was purified by anion-exchange column chromatography using Pharmacia FPLC. This synthetic oligonucleotide was used as a primer.

(2) Preparation of DNA Sample Derived from M. Avium Strain

M. avium strains described in Table 10 above were treated according to the method for preparation from Mycobacterium genus described in (2) of Example 2, and extraction and purification of DNA was carried out. Each of the purified DNA obtained was adjusted to give final concentration of 1 ng/μl (in 10 mM Tris-HCl buffer, pH 8.9), and used as DNA sample derived from each M. avium strain.

(3) Real-Time PCR

Using the Mac_12 Fw01 as a forward primer and the Mac_12 Rv01 as a reverse primer which were designed and synthesized in the above-described (1), the PCR was carried out as follows.

i) Preparation of Reaction Solution for PCR

A 10 mM Tris-HCl buffer solution (pH 8.9) containing 300 nM each of the primer Mac_12 Fw01 and the primer Mac_12 Rv01 obtained in the above-described (1), 30 times dilution of the undiluted solution (final concentration of 30000 times dilution of the undiluted solution) of SYBR™ Green I (product name of Molecular Probes Inc.), 1.5 mM $MgCl_2$, 80 mM KCl, 500 μg/ml BSA, 0.1% sodium cholate, 0.1% Triton X-100, 0.2 mM each of dATP, dCTP, dGTP and dTTP, and 40 unit/ml of Taq DNA polymerase (produced by Nippon Gene Co.) was prepared, and used as a reaction solution for PCR.

ii) Real-Time PCR

Using the DNA sample derived from each *M. avium* strain prepared in the above-described (2) as a template DNA of amplification target in the PCR, the real-time PCR by the intercalation method was carried out as follows, and quantitative monitoring of fluorescence was carried out simultaneously.

Firstly, to 20 µl of the reaction solution for PCR prepared in the above-described i) of (3), 1 µl (1 ng) of the DNA sample prepared in the above-described (2) was added and used as a sample for PCR.

Aforementioned sample for PCR was placed in each well of a 96-well reaction plate (MicroAmp Optical 96-well Reaction Plate; produced by Applied Biosystems Japan Ltd.), and the real-time PCR was carried out using a specialized thermal cycler/detector for the TaqMan™ PCR (ABI 7500; produced by Applied Biosystems Japan Ltd.). That is, after keeping the temperature at 95° C. for 10 minutes, a reaction cycle composed of heating at 95° C. for 15 seconds and 60° C. for 1 minute was repeated for 40 cycles, and the fluorescence intensity derived from SYBR™ Green I which has intercalated in a correlation with the quantity of the primer extension products was measured.

It should be noted that, in the above-described real-time PCR using the forward primer Mac_12 Fw01 and the reverse primer Mac_12 Rv01, if there exist a nucleotide sequence of the candidate clone D in the genomic DNA of each *M. avium* strain used as a template, it is anticipated that the DNA fragment (193 nucleotides) with a sequence shown in SEQ ID NO:194 in the nucleotide sequence of the candidate clone D could be replicated, and fluorescence could be detected.

(4) Melting Curve Analysis

As to each amplification product for individual DNA sample, the melting curve was depicted by plotting the melting temperature of the primer extension product (double-stranded DNA) as horizontal axis and the first derivation (variation) of fluorescence intensity as vertical axis, and then detection of peak was examined.

(5) Result

Figure 4:
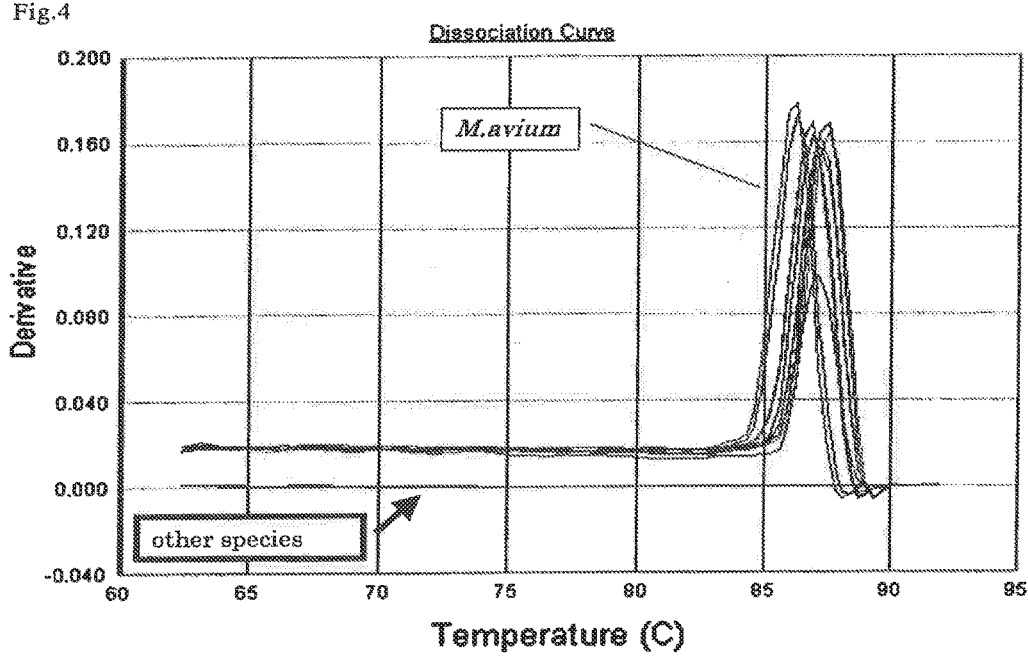
FIG. 4 shows the results of melting curve analyses obtained on the basis of the results of the real-time PCR by intercalator method obtained in Example 8 using primer Mac_12Fw01 and primer Mac_12Rv01 and using DNA samples from various strains of *M. avium*, DNA sample from *M. chimae* and DNA sample from *M. velatum* as a template.

The results of the melting curve analysis obtained for each DNA sample were shown collectively in FIG. 4.

As is clear from the results shown in FIG. 4, as the result of the melting curve analysis of the nucleic acid which had been amplified in the presence of SYBR Green I by performing the real-time PCR using the primer Mac_12 Fw01 and the primer Mac_12 Rv01 of the present invention, and using DNA samples obtained from 10 species of *M. avium* strain as a template, in either case, the fluorescent signal generated as the result of nucleic acid amplification was confirmed (FIG. 4: *M. avium*). In addition, obtained peaks of signal were all single peak. Further, the positions of the peaks were almost overlapped.

Otherwise, using DNA sample obtained from *Mycobacterium* genus other than *M. avium* (*M. chimaera* and *M. velatum*) as a template, and using the same primer, PCR was carried out by the same method as described in (1)-(4) above. In this case, the fluorescence signal generated as the result of nucleic acid amplification was not confirmed (FIG. 4: other species).

From the fact mentioned above, it turns out that, when the PCR is carried out using the primer Mac_12 Fw01 and the primer Mac_12 Rv01 of the present invention, and if any one of the above-descried 10 species of *M. avium* strain is present, it is possible to be detected, and furthermore specific detection of *M. avium* can be performed. And, from this fact, it was suggested that the candidate sequence D used as a target have a high probability of a consensus sequence of *M. avium*.

Example 9

Evaluation of Interspecific Conservation of Nucleotide Sequence of the Other Candidate Clone Among *M. Avium* Strains Based on the result of sequence (nucleotide sequence) analysis of the candidate clone A-G determined in (8) of Example 7, and from each candidate sequence A-G, each primer sequence for use in the PCR amplification detection was designed using a primer design tool on the web, Primer 3 (Whitehead Institute for Biomedical Research).

Name of the candidate sequence and SEQ ID NO of the nucleotide sequence of the candidate sequence, name of primer designed based on the candidate sequence (named by the present inventor) and SEQ ID NO of the nucleotide sequence thereof, and further, combination of forward primer and reverse primer to be used in the upcoming PCR were shown collectively in Table 12.

TABLE 12

| Candidate seqeunce | | Designed primer | | | |
|---|---|---|---|---|---|
| | | Combination | Forward Primer | | Reverse Primer | |
| Name | SEQ ID NO: | No. | Name | SEQ ID NO: | Name | SEQ ID NO: |
| Candidate Sequence A | 130 | 1 | Mac_06Fw01 | 137 | Mac_06Rv01 | 138 |
| | | 2 | Mac_06Fw02 | 139 | Mac_06Rv02 | 140 |
| | | 3 | Mac_06Fw03 | 141 | Mac_06Rv03 | 142 |
| | | 4 | Mac_06Fw04 | 143 | Mac_06Rv04 | 144 |
| Candidate Sequence B | 131 | 5 | Mac_10Fw01 | 145 | Mac_10Rv01 | 146 |
| | | 6 | Mac_10Fw02 | 147 | Mac_10Rv02 | 148 |
| Candidate Sequence C | 132 | 7 | Mac_11Fw01 | 149 | Mac_11Rv01 | 150 |
| | | 8 | Mac_11Fw02 | 151 | Mac_11Rv02 | 152 |
| | | 9 | Mac_11Fw03 | 153 | Mac_11Rv03 | 154 |
| | | 10 | Mac_11Fw04 | 155 | Mac_11Rv04 | 156 |
| | | 11 | Mac_11Fw05 | 157 | Mac_11Rv05 | 158 |
| Candidate Sequence D | 133 | 12 | Mac_12Fw01 | 159 | Mac_12Rv01 | 160 |
| | | 13 | Mac_12Fw02 | 161 | Mac_12Rv02 | 162 |
| | | 14 | Mac_12Fw03 | 163 | Mac_12Rv03 | 134 |

TABLE 12-continued

| | | | Designed primer | | | |
|---|---|---|---|---|---|---|
| Candidate seqeunce | | Combination | Forward Primer | | Reverse Primer | |
| Name | SEQ ID NO: | No. | Name | SEQ ID NO: | Name | SEQ ID NO: |
| Candidate Sequence E | 134 | 15 | Mac__13Fw01 | 165 | Mac__13Rv01 | 166 |
| | | 16 | Mac__13Fw02 | 167 | Mac__13Rv02 | 168 |
| | | 17 | Mac__13Fw03 | 169 | Mac__13Rv03 | 170 |
| Candidate Sequence F | 135 | 18 | Mac__15Fw01 | 171 | Mac__15Rv01 | 172 |
| | | 19 | Mac__15Fw02 | 173 | Mac__15Rv02 | 174 |
| Candidate Sequence G | 136 | 20 | Mac__16Fw02 | 175 | Mac__16Rv02 | 176 |
| | | 21 | Mac__16Fw03 | 177 | Mac__16Rv03 | 178 |
| | | 22 | Mac__16Fw05 | 179 | Mac__16Rv05 | 180 |
| | | 23 | Mac__16Fw07 | 181 | Mac__16Rv07 | 182 |

After that, the designed oligonucleotides were synthesized and purified by the same method as performed in (1) of Example 8. Using these synthesized oligonucleotides as a primer of the present invention, and by a combination of the forward primer and the reverse primer as described in Table 12, preparation of DNA sample, the real-time PCR, and the melting curve analysis were carried out by the same method as performed in (2) to (4) of Example 8.

As a result, in any case where the real-time PCR was carried out using any of the combination of primer, the same melting curve as shown in FIG. 4 of Example 8 was obtained. That is, using the combination of primer described in Table 12, and using each DNA sample obtained from 10 species of M. avium strain as a template, the real-time PCR was carried out. The melting curve analysis of the nucleic acid amplified in the presence of SYBR Green I. In consequence, in either case, the fluorescence signal generated as the result of nucleic acid amplification was confirmed. The peaks of signal obtained were all single peak. Furthermore, the positions of the peaks were almost overlapped.

In addition, by the same method as described in Example 8, using DNA sample obtained from Mycobacterium genus other than M. avium (M. chimaera and M. velatum) as a template, and using the same primer, PCR was carried out. In this case, the fluorescence signal generated as the result of nucleic acid amplification was not confirmed.

From the fact mentioned above, it turns out that, when the PCR is carried out using the primer of the present invention described in Table 12, and if any one of the above-descried 10 species of M. avium strain is present, it can be detected, and furthermore specific detection of M. avium can be performed.

That is, it turns out that, if the primer of the present invention is used, plural number of M. avium with various serotypes can be detected by single measurement in distinction from other Mycobacterium genus.

And, from this fact, it was suggested that either of the candidate sequence A to D used as a target have a high probability of a consensus sequence of M. avium.

Example 10

Evaluation of Specificity of Candidate Clone D for M. Avium (1) Synthesis of Primer Using the same instrument and by the similar procedure as used in (1) of Example 8, oligonucleotides of Mac_12Fw01 and Mac_12Rv01 were synthesized and purified.

(2) Preparation of DNA Sample

Using the same bacteria as used in Example 2 as mentioned below, and by the same method as performed in (2) of Example 2, DNA samples were prepared.
a: *Escherichia coli* (*E. coli*) (ATCC11775)
b: *Mycobacterium tuberculosis* (Human tubercle *bacillus*) (TMC102[H37Rv])
c: *Mycobacterium kansasii* (ATCC12478)
d: *Mycobacterium marinum* (ATCC927)
e: *Mycobacterium simiae* (ATCC25275)
f: *Mycobacterium scrofulaceum* (ATCC19981)
g: *Mycobacterium gordonae* (ATCC14470)
h: *Mycobacterium szulgai* (ATCC35799)
i: *M. avium* (IIID585)
j: *M. intracellulare* (ATCC13950)
k: *Mycobacterium gastri* (ATCC15754)
l: *Mycobacterium xenopi* (ATCC19250)
m: *Mycobacterium nonchrotnogenicum* (ATCC19530)
n: *Mycobacterium terrae* (ATCC15755)
o: *Mycobacterium triviale* (ATCC23292)
p: *Mycobacterium fortuitum* (ATCC6841)
q: *Mycobacterium chelonei* (ATCC35752)
r: *Mycobacterium abscessus* (ATCC19977)
s: *Mycobacterium peregrinum* (ATCC14467)

(3) Real-Time PCR

The real-time PCR was carried out by the same method as described in (3) of Example 2 except for using the primer Mac_12Fw01 and Mac_12Rv01 which was designed and synthesized in the above-described (1).

(4) Melting Curve Analysis

By the same method as used in (4) of Example 2, melting curve of each amplification product for individual DNA sample was depicted by plotting the melting temperature of the primer extension product (double-stranded DNA) as horizontal axis and the first derivation (variation) of fluorescence intensity as vertical axis, and then detection of peak was examined.

(5) Result

Figure 5:
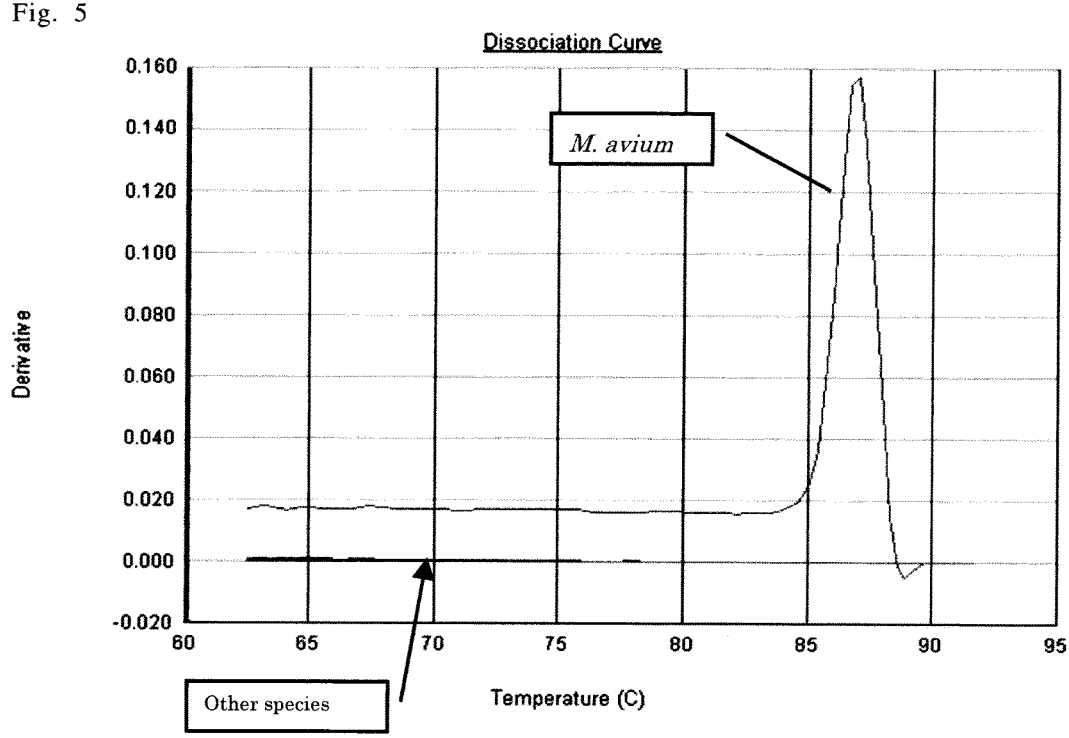
FIG. 5 shows the result of melting curve analysis obtained on the basis of the results of the real-time PCR by intercalator method obtained in Example 10 using primer Mac_12Fw01 and primer Mac_12Rv01 and using DNA sample from *Mycobacterium* genus and DNA sample from *Escherichia coli* as a template.

The results of the melting curve analysis obtained for each DNA sample were shown collectively in FIG. 5.

As is clear from the results shown in FIG. 5, as the result of the melting curve analysis of the nucleic acid which had been amplified by the real-time PCR using the primer Mac_12 Fw01 and the primer Mac_12 Rv01 of the present invention in the presence of SYBR Green I, only the case when the DNA sample derived from M. avium was used as a template, the fluorescence signal generated as the result of nucleic acid amplification was confirmed (FIG. 5: *M. avium*), and thus it could be determined as positive.

On the other hand, as is clear from FIG. 5, when the real-time PCR was carried out in the same way using the DNA derived from *Mycobacterium* genus except for *M. avium* and the DNA derived from bacteria of other genus like *E. coli* as a template, and using the same combination of primers, relevant fluorescence signal was not confirmed (FIG. 5: other species), and all cases were determined as negative.

Further, as is clear from FIG. 5, from the fact that a single clear peak was obtained as the result of the melting curve analysis when DNA sample derived from *M. avium* was used as a template, it turns out that the detection method carried out is a method having quite high specificity for *M. avium*.

From the fact stated above, it can be understood that, by the use of the oligonucleotide of the present invention as a primer for the PCR, *M. avium* can be detected specifically. In addition, because the detection by nucleic acid amplification such as PCR is expected to have high sensitivity, isolation of bacterium is not necessary, but the clinical specimen can be used directly for detection. Therefore, the detection of *M. avium* can be finished within a day at the longest, while it took several weeks for bacterial cultivation in the conventional detection method where detection was performed after bacterial cultivation.

Example 11

Evaluation of *M. Avium* Specificity of the Other Candidate Clone 2

(1) Synthesis of the Primer of the Present Invention

Using the same instrument and by the similar procedure as used in (1) of Example 8, oligonucleotides other than Mac_12 Fw01 and the Mac_12 Rv01 described in the above Table 12 were synthesized and purified.

These synthetic oligonucleotides were used as a primer.
(2) Preparation of DNA Sample Using the same bacteria as used in Example 10, and by the same method as described in (2) of Example 2, DNA samples were prepared.
(3) Real-Time PCR The real-time PCR was carried out by the same method as performed in (3) of Example 2 except for using the primer synthesized and purified in the above-described (1) and using in combination as described in the above-described Table 12.
(4) Melting Curve Analysis By the same method as described in (4) of Example 2, melting curve for each amplification product for individual DNA sample was depicted by plotting the melting temperature of the primer extension product (double-stranded DNA) as horizontal axis and the first derivation (variation) of fluorescence intensity as vertical axis, and then detection of peak was examined.
(5) Result As is the case with the result of Example 10, as the result of the melting curve analysis of the nucleic acid which had been amplified using the primer of the present invention in the presence of SYBR Green I, in any combination of the primers described in Table 12 is used, only the case when the real-time PCR was carried out using DNA sample derived from *M. avium* as a template, the fluorescence generated as the result of nucleic acid amplification was confirmed, and thus it could be determined as positive.

On the other hand, when the real-time PCR was carried out in the same way using the DNA derived from *Mycobacterium* genus except for *M. avium* and the DNA derived from bacteria of other genus like *E. coli* as a template, and using any and every same combination of primers described in Table 12, relevant fluorescence signal was not confirmed, and all cases were determined as negative.

Further, from the fact that a single clear peak was obtained as the result of the melting curve analysis when DNA sample derived from *M. avium* was used as a template, it turns out that the detection method carried out is a method having quite high specificity for *M. avium*.

From the fact stated above, it turns out that, by the use of the oligonucleotide of the present invention as a primer for the PCR, *M. avium* can be detected specifically. In addition, because the detection by nucleic acid amplification such as PCR is expected to have high sensitivity, isolation of bacterium is not necessary, but the clinical specimen can be used directly for detection. Therefore, the detection of *M. avium* can be finished within a day at the longest, while it took several weeks for bacterial cultivation in the conventional detection method where detection was performed after bacterial cultivation.

Example 12

Test for Minimum Detection Sensitivity 2

Using the real-time detection method, verification of detection sensitivity was carried out for a case where the candidate sequence D was targeted.
(1) Synthesis of the Primer for Detection of *M. Avium* of the Present Invention Using the same instrument and by the similar procedure as described in (1) of Example 2, oligonucleotides of Mac_12 Fw01 and the Mac_12 Rv01 were synthesized and purified. And these oligonucleotides were used as a primer.
(2) Preparation of DNA Sample DNA sample prepared from *M. avium* (*Mycobacterium avium* IID 585) in (1) of Example 7 was used.

Quantity of DNA in the sample was determined by measuring absorbance of aforementioned DNA sample. The quantity of the DNA (copy number of the genome) in the sample was determined by comparing the obtained quantity of DNA with the measurement value obtained in the same way by measuring absorbance of the known concentration of genomic DNA of *M. avium* as a sample. The genomic DNA of $10^8$ copy/μl was obtained.

Subsequently, the DNA sample was diluted using 10 mM Tris-HCl buffer, pH 8.9 to a dilution series of $10^5$, $10^4$, $10^3$, $10^2$, 10 and 5 copy/μl, and used as a DNA samples for PCR.
(3) Real-Time PCR
i) Preparation of Reaction Solution for PCR A 10 mM Tris-HCl buffer solution (pH 8.9) containing 300 nM each of the primer Mac_12 Fw01 and the primer Mac_12 Rv01 obtained in the above-described (1), 30 times dilution of the undiluted solution (final concentration was 30000 times dilution of the undiluted solution) of SYBR™ Green I (product name of Molecular Probes Inc.), 1.5 mM $MgCl_2$, 80 mM KCl, 500 μg/ml BSA, 0.1% sodium cholate, 0.1% Triton X-100, 0.2 mM each of dATP, dCTP, dGTP and dTTP, and 40 unit/ml of Taq DNA polymerase (produced by Nippon Gene Co.) was prepared, and used as a reaction solution for PCR.

ii) Real-Time PCR

To a 20 μl of the reaction solution for PCR prepared in the above described i) of (3), 1 μl (1 ng) of the DNA sample for PCR prepared in the above described (2) was added and used as a sample for PCR.

This sample for PCR was placed in each well of a 96-well reaction plate (MicroAmp Optical 96-well Reaction Plate; produced by Applied Biosystems Japan Ltd.), and the real-time PCR was carried out using a specialized thermal cycler/detector for the TaqMan™ PCR (ABI 7500; produced by Applied Biosystems Japan Ltd.). That is, after keeping the temperature at 95° C. for 10 minutes, a reaction cycle composed of heating at 95° C. for 15 seconds and 60° C. for 1 minute was repeated for 40 cycles, and the fluorescence intensity derived from SYBR™ Green I which has intercalated in a correlation with the quantity of the primer extension products was measured.

It should be noted that, fluorescence intensity was measured using a function of digitalizing relative fluorescent intensity ratio equipped to the thermal cycler used for the measurement, for each of the 96 well reaction plates used for the measurement.

(4) Result

Figure 6:
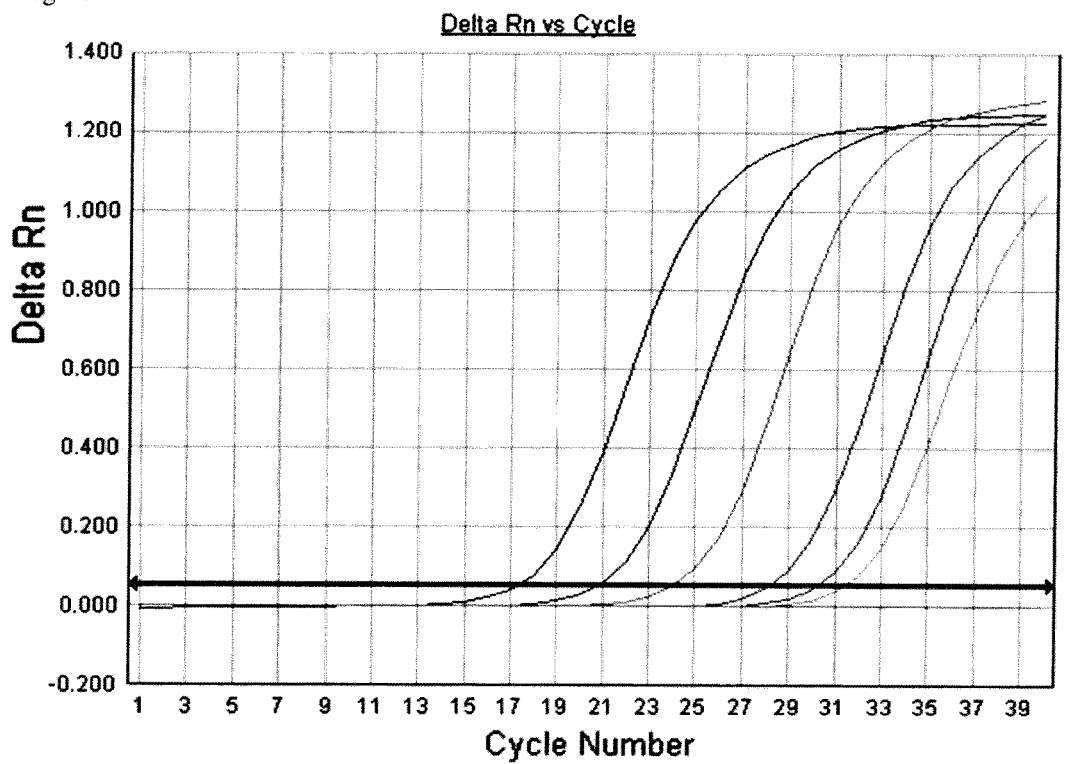
FIG. 6 shows an amplification curve obtained on the basis of the results of the real-time PCR by intercalator method obtained in Example 12 using primer Mac_12Fw01 and primer Mac_12Rv01 and using genomic DNA sample from *M. avium* as a template.

From the experimental data obtained, for each DNA sample for PCR, according to routine procedure commonly performed in the real-time PCR method, by the same method as described in (4) of Example 5, an amplification curve was made up by plotting the fluorescence intensity derived from reporter dye (Rn, y-axis) for each cycle number of PCR (x-axis). The amplification curve obtained was shown in FIG. 6.

Subsequently, from the obtained amplification curve, the standard curve was made up by the following method.

Figure 7:
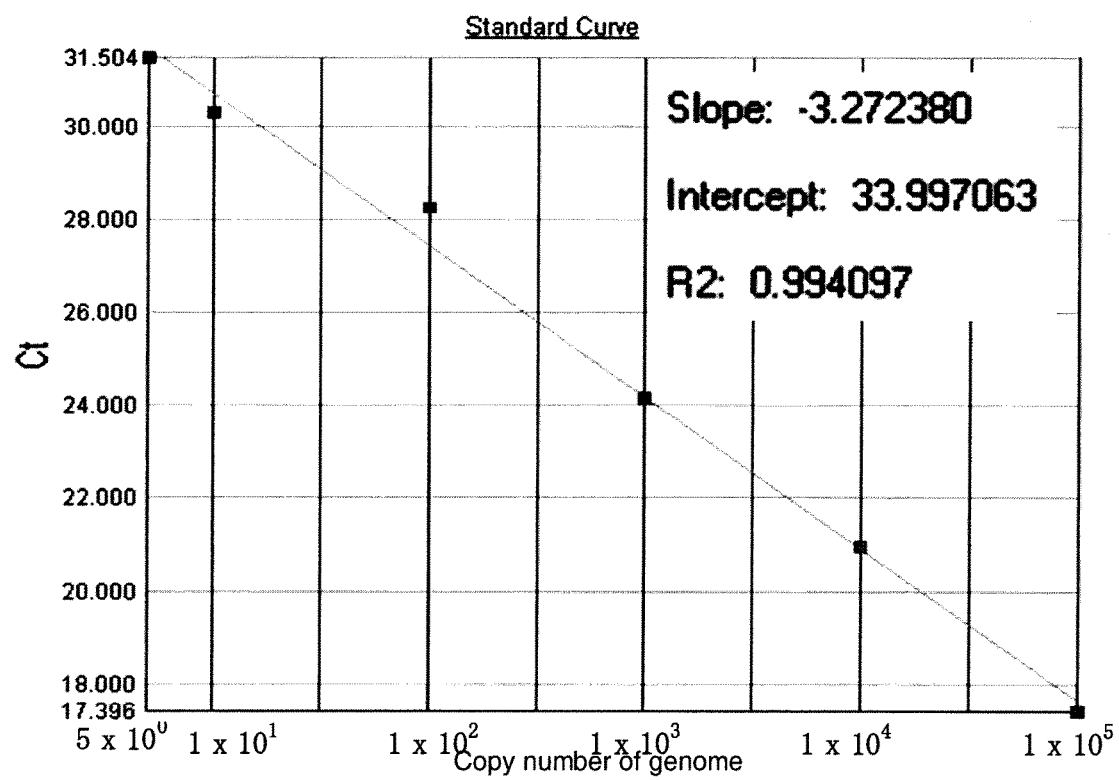
FIG. 7 shows the results of detection obtained by the real-time PCR in Example 12, which is a standard curve drawn by plotting Ct value (Y-axis) for the copy number of genome (X-axis, logarithmic scale) of each DNA sample for PCR.

That is, an Rn part of the amplification curve obtained (FIG. 6) where the fluorescence intensity amplified exponentially was selected, and a Threshold line (Th) was drawn. The crossing point of the Th with the fluorescence intensity derived from each DNA sample for PCR was defined as Threshold cycle (Ct). After that, the Ct value (y-axis) was plotted for the copy number of the genome of each used DNA sample for PCR (x-axis), and the approximated curve obtained for each Ct was used as a standard curve. The standard curve obtained is shown in FIG. 7.

$$y=-3.272x+34.00$$

$$R^2=0.994$$

In consequence, from the fact that the fluorescence was detected by the real-time PCR, it turned out that $M.$ $avium$ can be detected by performing the real-time PCR using the oligonucleotide involved in the present invention as a primer.

In addition, it also turns out that, as the standard curve has become available, quantitative determination of $M.$ $avium$ is possible by the real-time PCR using the primer and the probe of the present invention. Further, it turns out from FIG. 7 that the real-time PCR method using the primer and the probe of the present invention can detect $M.$ $avium$ even under the condition where only 5 copies of the genomic DNA of $M.$ $avium$ are present as initial quantity.

In addition, the PCR by the present method showed 102% of amplification efficiency according to calculations, and was confirmed to have high reactivity.

Further, when the same experiment was carried out using the other combination of primers described in the above Table 12, almost the same results were obtained. From the facts described above, it has become clear that, by conducting the real-time PCR using candidate sequences A-G as a target, detection and quantification of $M.$ $avium$ can be performed.

INDUSTRIAL APPLICABILITY

According to the method for detection of $M.$ $avium$ by using the primer and/or probe of the present invention, the detection of $M.$ $avium$ can be performed more rapidly and with high precision compared with a conventional bacterial species identification method performed by culture examination on a specific medium. Further, the method for detection of $M.$ $avium$ of the present invention can exclude any false-positive result for the diagnosis and can also detect and diagnose $M.$ $avium$ with high precision compared with a diagnosis method performed by PCR using a conventional primer and/or probe.

Still further, the method for detection of $M.$ $avium$ of the present invention can quantify the $M.$ $avium$ cell.

---

The invention claimed is:

1. A primer pair for detecting *Mycobacterium avium* consisting of a first primer and a second primer
   wherein the first primer is not more than about 50 nucleotides in length and comprises an oligonucleotide that comprises the nucleotide sequence of SEQ ID NO: 179;
   wherein at least one of the first primer or the second primer is labeled with a labeling substance, which is bound via a covalent bond or a linker; and
   wherein the first primer and the second primer are together capable of amplifying a genomic DNA fragment of *Mycobacterium avium* genome.

2. The primer pair according to claim 1, wherein the labeling substance is selected from a radioisotope, an enzyme, a fluorescent substance, a luminescent substance, and biotin.

3. The primer pair according to claim 1, wherein the second primer of said primer pair is not more than about 50 nucleotides in length and comprises the nucleotide sequence of SEQ ID NO: 180.

4. The primer pair according to claim 3, wherein the first primer and the second primer are each no more than about 25 nucleotides in length.

5. The primer pair according to claim 3, wherein the oligonucleotide of the first primer consists of the nucleotide sequence of SEQ ID NO: 179 and an oligonucleotide of the second primer consists of the nucleotide sequence of SEQ ID NO: 180.

6. A reagent kit comprising:
   (i) a primer set for detecting *Mycobacterium avium* consisting of
   (a) a first primer consisting of a primer that is not more than about 50 nucleotides in length and comprises an oligonucleotide that comprises the nucleotide sequence of SEQ ID NO: 179, is labeled with a labeling substance, which is bound via a covalent bond or a linker, and is capable of hybridizing with a genomic DNA fragment of *Mycobacterium avium* genome; and
   (b) optionally, an additional primer, wherein the additional primer is not more than about 50 nucleotides in length and comprises a contiguous portion of at least 15 nucleotides of the complementary sequence of SEQ ID NO:136, and is capable of hybridizing with the genomic DNA fragment of *Mycobacterium avium* genome;
   (ii) (1) a nucleic acid synthetase and/or (2) a substrate for a nucleic acid synthetase and/or (3) a double strand intercalator and/or (4) a signal detection substance; and
   (iii) wherein all primers for detecting *Mycobacterium avium* in the reagent kit are capable of specifically hybridizing to the *Mycobacterium avium* genome under highly stringent conditions.

7. The reagent kit according to claim 6, further comprising:
   a probe, wherein the probe comprises (a) an oligonucleotide that comprises a nucleotide sequence selected from:
   SEQ ID NO: 136, or the full nucleotide sequence complementary thereto; wherein the probe is no longer than about 1100 nucleotides; or
   SEQ ID NO: 179 or 180, or the full nucleotide sequence complementary thereto; wherein the probe is no longer than about 50 nucleotides; or
   SEQ ID NO: 204, or the full nucleotide sequence complementary thereto; or
   20-50 consecutive nucleotides of SEQ ID NO: 204, or the full nucleotide sequence complementary thereto; and
   optionally (b) a labeling substance, which is bound to the oligonucleotide via a covalent bond or a linker; and wherein the probe is capable of hybridizing with a genomic DNA fragment of *Mycobacterium avium* genome.

8. A reagent kit comprising:
   (i) a primer pair for detecting *Mycobacterium avium* consisting of a first primer and a second primer, wherein (a) the first primer is not more than about 50 nucleotides in length and comprises an oligonucleotide that comprises the nucleotide sequence of SEQ ID NO: 179; (b) at least one of the first primer or the second primer is labeled with a labeling substance, which is bound via a covalent bond or a linker; and (c) the first primer and the second primer are capable of hybridizing with a genomic DNA fragment of *Mycobacterium avium* genome; and
   (ii) (1) a nucleic acid synthetase and/or (2) a substrate for a nucleic acid synthetase and/or (3) a double strand intercalator and/or (4) a signal detection substance; and
   (iii) wherein all primers for detecting *Mycobacterium avium* in the reagent kit are capable of specifically hybridizing to the *Mycobacterium avium* genome under highly stringent conditions.

9. The reagent kit according to claim 8, further comprising:
   a probe, wherein the probe comprises (a) an oligonucleotide that comprises a nucleotide sequence selected from:

SEQ ID NO: 136, or the full nucleotide sequence complementary thereto; wherein the probe is no longer than about 1100 nucleotides; or SEQ ID NO: 179 or 180, or the full nucleotide sequence complementary thereto; wherein the probe is no longer than about 50 nucleotides; or SEQ ID NO: 204, or the full nucleotide sequence complementary thereto; or 20-50 consecutive nucleotides of SEQ ID NO: 204, or the full nucleotide sequence complementary thereto; and optionally (b) a labeling substance, which is bound to the oligonucleotide via a covalent bond or a linker; and wherein the probe is capable of hybridizing with a genomic DNA fragment of *Mycobacterium avium* genome.

10. The reagent kit according to claim 8, wherein the second primer of said primer pair comprises SEQ ID NO: 180.

11. The reagent kit according to claim 8, wherein the labeling substance is selected from a radioisotope, an enzyme, a fluorescent substance, a luminescent substance, and biotin.

12. The reagent kit according to claim 8, wherein the second primer of said primer pair is not more than about 50 nucleotides in length and comprises the nucleotide sequence of SEQ ID NO: 180.

13. The reagent kit according to claim 12, wherein the first primer and the second primer are each no more than about 25 nucleotides in length.

14. A reagent kit comprising:
(i) a probe consisting of
(a) an oligonucleotide that comprises a nucleotide sequence selected from:
SEQ ID NO: 136, or the full length sequence complementary thereto; wherein the probe is no longer than about 1100 nucleotides; or
SEQ ID NO: 179 or 180, or the full nucleotide sequence complementary thereto; wherein the probe is no longer than about 50 nucleotides; or
SEQ ID NO: 204, or the full nucleotide sequence complementary thereto; or
20-50 consecutive nucleotides of SEQ ID NO: 204, or the full nucleotide sequence complementary thereto; and
(b) a labeling substance bound to the oligonucleotide via a covalent bond or a linker; wherein the labeling substance comprises a reporter fluorescent dye and a quencher dye; and wherein the probe is capable of hybridizing with a genomic DNA fragment of *Mycobacterium avium* genome; and
(ii) a primer composition for detecting *Mycobacterium avium* consisting essentially of a first primer or a primer pair;
wherein (a) the first primer is not more than about 50 nucleotides in length and comprises an oligonucleotide that comprises the nucleotide sequence of SEQ ID NO: 179; and optionally (b) a labeling substance which is bound to the oligonucleotide via a covalent bond or a linker; wherein the first primer is capable of hybridizing with a genomic DNA fragment of *Mycobacterium avium* genome; and
wherein the primer pair consists of the first primer and a second primer, and the first primer and the second primer are capable of amplifying a genomic DNA fragment of *Mycobacterium avium* genome; and
(iii) (1) a nucleic acid synthetase and/or (2) a substrate for a nucleic acid synthetase and/or (3) a double strand intercalator and/or (4) a signal detection substance.

15. The reagent kit according to claim 14, wherein the reporter fluorescent dye is covalently bound to the 5'-terminal of the oligonucleotide and the quencher dye is covalently bound to the 3'-terminal of the oligonucleotide.

* * * * *

SEQUENCE LISTING

```
<160> NUMBER OF SEQ ID NOS: 205

<210> SEQ ID NO 1
<211> LENGTH: 981
<212> TYPE: DNA
<213> ORGANISM: Mycobacterium avium

<400> SEQUENCE: 1
cggttacgtt tgaccggggc atgcccgtca acagcacgtt cggccttggc cacctgctca      60
tcgatccccc gcagcgtgcg ccgggcccgg tcatggcggt actggtagtg gatgatccgg     120
tccgggatgc cgcgggtttt ctcgccgctg gttgatggcc agggctgggt gagcaccagg     180
ccgtcgggga tcgcctcatc ggagtgcttg tcgcgccact cgcgcaccac atcaggtaaa     240
aacggaatcc tcgcgccgag aatgtaggac agccctgccg cgtgcagggc gacctggttg     300
gcttccgaga tcatcccggc atcagcgacg accgtgacgt cggtgagttg gtgagcggcc     360
ttgaacgcgt tgatcaccgg cagcatggtc gcggtctctg ccttattgcc ctcaaaggcc     420
gccaccgtca acgggaaccc gccagcatcg gtcaacaacc ccagggtgat ctgcgggtcc     480
```

```
aaccgtcttt ccttggagaa tccgggctcc cggaacccat caccagcatc ggtctcgaag    540
tgcagcgtcg acacgtcata gagcaccaga ctggccggac ccaattgcgc gtgggcagcg    600
catgcggtcg aaagcgcttg ccggaaagcg ggtttggcga acaccggcag acggcggttc    660
agcgtcggat acgacaccgg gacgacccca gtctcctcga cgacccgaag tgaatcggcc    720
ttgctggtcg gttcgatgat ccgggccaac accaactgac gaaacgcctc atccccatcg    780
gcgacgttgg cgaacccgac cttgtcataa gcagcgcaca atgcttccca cagcagcgcc    840
gacttcgagg acgtgatcgg caacggctcg gccgccgaac gttcggccaa gccaaggtcg    900
agttgcgctt ggccggcggc cagtcgctgc gccgcggcag ccttcaaagc ggccaccccg    960
gcctcgtcat gcgccgaacc c                                              981

<210> SEQ ID NO 2
<211> LENGTH: 326
<212> TYPE: DNA
<213> ORGANISM: Mycobacterium avium

<400> SEQUENCE: 2
tgtgcaggtc gtgtagtcct cgcggcgcgg gtcacgccgg atcgagcatc tgggttcggc     60
gcatgacgag gccggggtgg ccgctttgaa ggctgccgcg gcgcagcgac tggccgccgg    120
ccaagcgcaa ctcgaccttg gcttggccga acgttcggcg gccgagccgt tgccgatcac    180
gtcctcgaag tcggcgctgc tgtgggaagc attgtgcgct gcttatgaac aaggtcgggt    240
tcgccaacgt cgccgatggg gatgaggcgt ttcgtcagtt ggtgttggcc cggatcatcg    300
aaccgaccag caaggccgat tcactt                                         326

<210> SEQ ID NO 3
<211> LENGTH: 503
<212> TYPE: DNA
<213> ORGANISM: Mycobacterium avium

<400> SEQUENCE: 3
cttgggttac cgtgagcttg tcgtccatct gcgcgacatc acggagtcgc cggtaggcga     60
agtcgccgct gaacgcctgg ctgaaaccgt tccccaacag aagcgagatt tttccagcgc    120
cgttcttcgc atcagccaga gcttcggaaa atgttgagat cacgacggac atgtgagcac    180
tctacggagc ggtccgggaa gaattcccag cctcacgggg ccgaacatcc ggtgcgggaa    240
ctcaggtctc ctcgaaccca gattgatcga acttcaacgt cttcgcattc tccgacacgg    300
tccggacctt gccctcgtcg aaacctgttg cgtcggtggc ttcgatctcg atcttcaccg    360
tcagttcgat gccctggtcc cgtaggttgg cgatgacttc gtcggcgatg ttcttgaagt    420
ccagcgcgat cttgtccgag ctgagcgtct tcaccccgta gaagcgggtc ttggctgggg    480
ggaaggcaac atcaactggt ggc                                            503

<210> SEQ ID NO 4
<211> LENGTH: 587
<212> TYPE: DNA
<213> ORGANISM: Mycobacterium avium

<400> SEQUENCE: 4
tccgctatct aaaggctcat ggctaccaag tcgtcgacgg ctataccta gttccaccca      60 agatcggagg ttagcgcggg tgaaagcgct ccttgaattt atcgttcaat actgcggctt    120
cctctacctc aacccaggct acagaatcac gaactcggcc acccgaggct tggccgacat    180
```
cgacgcatcg attacgttca ccggcgcgga gatcgtgtgg cagatcatta atgatcgcgg 240
gctcatctac tttgctgcgg cgccgtcaca aggtgtgtct gacgattcgt atgcactttc 300
ccttattcgt caatatttgg aaggcggcga ggatgtcggt gctggccccg cgatcgacga 360
ggcgagctgg ttgagcgcaa acttgagccg ggtcgagcgg ctatttaccg atgaatcgaa 420
cgctgcgcgc gtctgcgacg aacttgccga tctacgacgc tccaattcat tcaaaaaatg 480
gggatggccc aaaccggagg aaaccgacta gcggcaaatc ctagaccagg agagtccgcg 540
gccgataatg cagacccgac ttttatcagg ctagtgcgca cgtagga 587

<210> SEQ ID NO 5
<211> LENGTH: 622
<212> TYPE: DNA
<213> ORGANISM: Mycobacterium avium

<400> SEQUENCE: 5
ccggcggcgt gaaccagacg gccctaggat cagctggcgt caggaggtcg aacgcggccg 60
aagccgctcg ccgagtgccc ggtgaaccag gggtgtggat ctttctgttc ggcgacatgg 120
cggtattcgg agtgttcttc gccaccttca tgtatcagcg ttcgttggca ccgaagctgt 180
tcgacgactc gcgtcacacc aggagcatcg gcatcgggct aaacaacacg ctggtcctgc 240
tgaccagctc attgttcgtg gtgaccgcga tgcgggcgat tcgctcgtcg caacgcggcc 300
cagcgcaact cgcaggtgcg ctgatctgcg gcctcgcgtt cgtcggactc aaggccgtcg 360
agtacgccgc caaggtgtcc cagggccacg tccccaccca aaacaacttc tgcctctact 420
acttcatcct caccgggctg cacctgttcc atgtgctgat cggggtcgcg gtgctcatcc 480
tgctgttctt tcagggtcga cgcaccgaac tgagccccac ccgaacgggc ctcgtcgaag 540
gtggcgcatg tttccggcac ctcgtcgacc tatgtagatc gttttgttcg cccttctcta 600
cctggtgagc tgagtgatgc cc 622

<210> SEQ ID NO 6
<211> LENGTH: 20
<212> TYPE: DNA
<213> ORGANISM: Artificial sequence
<220> FEATURE:
<223> OTHER INFORMATION: oligonucleotide primer

<400> SEQUENCE: 6
cattgtgcgc tgcttatgac 20

<210> SEQ ID NO 7
<211> LENGTH: 19
<212> TYPE: DNA
<213> ORGANISM: Artificial sequence
<220> FEATURE:
<223> OTHER INFORMATION: oligonucleotide primer

<400> SEQUENCE: 7
gaagtgaatc ggccttgct 19

<210> SEQ ID NO 8
<211> LENGTH: 18
<212> TYPE: DNA
<213> ORGANISM: Artificial sequence
<220> FEATURE:
<223> OTHER INFORMATION: oligonucleotide primer

<400> SEQUENCE: 8
catgcccgtc aacagcac 18

<210> SEQ ID NO 9
<211> LENGTH: 18
<212> TYPE: DNA
<213> ORGANISM: Artificial sequence
<220> FEATURE:
<223> OTHER INFORMATION: oligonucleotide primer

<400> SEQUENCE: 9
aaccagcggc gagaaaac                                                     18

<210> SEQ ID NO 10
<211> LENGTH: 19
<212> TYPE: DNA
<213> ORGANISM: Artificial sequence
<220> FEATURE:
<223> OTHER INFORMATION: oligonucleotide primer

<400> SEQUENCE: 10
tgcaggtcgt gtagtcctc                                                    19

<210> SEQ ID NO 11
<211> LENGTH: 18
<212> TYPE: DNA
<213> ORGANISM: Artificial sequence
<220> FEATURE:
<223> OTHER INFORMATION: oligonucleotide primer

<400> SEQUENCE: 11
aaggtcgagt tgcgcttg                                                     18

<210> SEQ ID NO 12
<211> LENGTH: 20
<212> TYPE: DNA
<213> ORGANISM: Artificial sequence
<220> FEATURE:
<223> OTHER INFORMATION: oligonucleotide primer

<400> SEQUENCE: 12
accagttgat gttgccttcc                                                   20

<210> SEQ ID NO 13
<211> LENGTH: 21
<212> TYPE: DNA
<213> ORGANISM: Artificial sequence
<220> FEATURE:
<223> OTHER INFORMATION: oligonucleotide primer

<400> SEQUENCE: 13
tctcgatctt caccgtcagt t                                                 21

<210> SEQ ID NO 14
<211> LENGTH: 21
<212> TYPE: DNA
<213> ORGANISM: Artificial sequence
<220> FEATURE:
<223> OTHER INFORMATION: oligonucleotide primer

<400> SEQUENCE: 14
aaggctcatg gctaccaagt c                                                 21

<210> SEQ ID NO 15
<211> LENGTH: 19
<212> TYPE: DNA
<213> ORGANISM: Artificial sequence
<220> FEATURE:

<223> OTHER INFORMATION: oligonucleotide primer

<400> SEQUENCE: 15
tggccgagtt cgtgattct                                                         19

<210> SEQ ID NO 16
<211> LENGTH: 20
<212> TYPE: DNA
<213> ORGANISM: Artificial sequence
<220> FEATURE:
<223> OTHER INFORMATION: oligonucleotide primer

<400> SEQUENCE: 16
acctcaaccc aggctacaga                                                        20

<210> SEQ ID NO 17
<211> LENGTH: 22
<212> TYPE: DNA
<213> ORGANISM: Artificial sequence
<220> FEATURE:
<223> OTHER INFORMATION: oligonucleotide primer

<400> SEQUENCE: 17
gaataaggga aagtgcatac ga                                                     22

<210> SEQ ID NO 18
<211> LENGTH: 18
<212> TYPE: DNA
<213> ORGANISM: Artificial sequence
<220> FEATURE:
<223> OTHER INFORMATION: oligonucleotide primer

<400> SEQUENCE: 18
cgatctacga cgctccaa                                                          18

<210> SEQ ID NO 19
<211> LENGTH: 21
<212> TYPE: DNA
<213> ORGANISM: Artificial sequence
<220> FEATURE:
<223> OTHER INFORMATION: oligonucleotide primer

<400> SEQUENCE: 19
gcgcactagc ctgataaaag t                                                      21

<210> SEQ ID NO 20
<211> LENGTH: 20
<212> TYPE: DNA
<213> ORGANISM: Artificial sequence
<220> FEATURE:
<223> OTHER INFORMATION: oligonucleotide primer

<400> SEQUENCE: 20
gcactttccc ttattcgtca                                                        20

<210> SEQ ID NO 21
<211> LENGTH: 21
<212> TYPE: DNA
<213> ORGANISM: Artificial sequence
<220> FEATURE:
<223> OTHER INFORMATION: oligonucleotide primer

<400> SEQUENCE: 21
gaatgaattg gagcgtcgta g                                                      21

```
<210> SEQ ID NO 22
<211> LENGTH: 21
<212> TYPE: DNA
<213> ORGANISM: Artificial sequence
<220> FEATURE:
<223> OTHER INFORMATION: oligonucleotide primer

<400> SEQUENCE: 22
agggcgaaca aaacgatcta c                                              21

<210> SEQ ID NO 23
<211> LENGTH: 21
<212> TYPE: DNA
<213> ORGANISM: Artificial sequence
<220> FEATURE:
<223> OTHER INFORMATION: oligonucleotide primer

<400> SEQUENCE: 23
cccaaaacaa cttctgcctc t                                              21

<210> SEQ ID NO 24
<211> LENGTH: 119
<212> TYPE: DNA
<213> ORGANISM: Artificial sequence
<220> FEATURE:
<223> OTHER INFORMATION: oligonucleotide probe

<400> SEQUENCE: 24
cattgtgcgc tgcttatgac aaggtcgggt tcgccaacgt cgccgatggg gatgaggcgt    60
tttcgttcag ttggtgttgg cccggatcat cgaaccgacc agcaaggccg attcacttc    119

<210> SEQ ID NO 25
<211> LENGTH: 134
<212> TYPE: DNA
<213> ORGANISM: Artificial sequence
<220> FEATURE:
<223> OTHER INFORMATION: oligonucleotide probe

<400> SEQUENCE: 25
catgcccgtc aacagcacgt tcggccttgg ccacctgctc atcgatcccc cgcagcgtgc    60
gccgggcccg gtcatggcgg tactggtagt ggatgatccg gtccgggatg ccgcgggttt   120
tctcgccgct ggtt                                                    134

<210> SEQ ID NO 26
<211> LENGTH: 137
<212> TYPE: DNA
<213> ORGANISM: Artificial sequence
<220> FEATURE:
<223> OTHER INFORMATION: oligonucleotide probe

<400> SEQUENCE: 26
tgcaggtcgt gtagtcctcg cggcgcgggt cacgccggat cgagcatctg ggttcggcgc    60
atgacgaggc cggggtggcc gctttgaagg ctgccgcggc gcagcgactg gccgccggcc   120
aagcgcaact cgaccTT                                                  137

<210> SEQ ID NO 27
<211> LENGTH: 155
<212> TYPE: DNA
<213> ORGANISM: Artificial sequence
<220> FEATURE:
<223> OTHER INFORMATION: oligonucleotide probe

<400> SEQUENCE: 27
```
accagttgat gttgccttcc ccccagccaa gacccgcttc tacggggtga agacgctcag    60
ctcggacaag atcgcgctgg acttcaagaa catcgccgac gaagtcatcg ccaacctacg   120
ggaccagggc atcgaactga cggtgaagat cgaga                              155

<210> SEQ ID NO 28
<211> LENGTH: 150
<212> TYPE: DNA
<213> ORGANISM: Artificial sequence
<220> FEATURE:
<223> OTHER INFORMATION: oligonucleotide probe

<400> SEQUENCE: 28
aaggctcatg gctaccaagt cgtcgacggc tatacccctag ttccacccaa gatcggaggt    60
tagcgcgggt gaaagcgctc cttgaattta tcgttcaata ctgcggcttc ctctacctca   120
acccaggcta cagaatcacg aactcggcca                                    150

<210> SEQ ID NO 29
<211> LENGTH: 184
<212> TYPE: DNA
<213> ORGANISM: Artificial sequence
<220> FEATURE:
<223> OTHER INFORMATION: oligonucleotide probe

<400> SEQUENCE: 29
acctcaaccc aggctacaga atcacgaact cggccaccecg aggcttggcc gacatcgacg    60
catcgattac gttcaccggc gcggcgatcg tgtggcagat cattaatgaa tcgcgggctc   120
atctactttg ctgcggcgcc gtcacaaggt gtgtctgacg attcgtatgc actttcccttt   180 attc                                                                184

<210> SEQ ID NO 30
<211> LENGTH: 132
<212> TYPE: DNA
<213> ORGANISM: Artificial sequence
<220> FEATURE:
<223> OTHER INFORMATION: oligonucleotide probe

<400> SEQUENCE: 30
cgatctacga cgctccaatt cattcaaaaa atggggatgg cccaaaccgg aggaaaccga    60
ctagcggcaa atcctagacc aggagagtcc gcggccgata atgcagaccc gacttttatc   120
aggctagtgc gc                                                      132

<210> SEQ ID NO 31
<211> LENGTH: 182
<212> TYPE: DNA
<213> ORGANISM: Artificial sequence
<220> FEATURE:
<223> OTHER INFORMATION: oligonucleotide probe

<400> SEQUENCE: 31
gcactttccc ttattcgtca atatttggaa ggcggcgagg atgtcggtgc tggccccgcg    60
gatcggacga ggcgagctgg ttgagcgcaa acttgagccg ggtcgagcgg ctatttaccg   120
atgaatcgaa cgctgcgcgc gtctgcgacg aacttgccga tctacgacgc tccaattcat   180
tc                                                                 182

<210> SEQ ID NO 32
<211> LENGTH: 199
<212> TYPE: DNA
<213> ORGANISM: Artificial sequence
<220> FEATURE:
<223> OTHER INFORMATION: oligonucleotide probe

<400> SEQUENCE: 32

```
agggcgaaca aaacgatcta caataggtcg acgaggtgcc ggaaacatgc gccaccttcg      60
acgaggcccg ttcgggtggg gctcagttcg gtgcgtcgac cctgaaagaa cagcaggatg     120
agcaccgcga ccccgatcag cacatggaac aggtgcagcc cggtgaggat gaagtagtag     180
aggcagaagt tgttttggg                                                  199
```

<210> SEQ ID NO 33
<211> LENGTH: 21
<212> TYPE: DNA
<213> ORGANISM: Artificial sequence
<220> FEATURE:
<223> OTHER INFORMATION: oligonucleotide primer

<400> SEQUENCE: 33

```
ctgttcgagt ggcaacaagt c                                                21
```

<210> SEQ ID NO 34
<211> LENGTH: 20
<212> TYPE: DNA
<213> ORGANISM: Artificial sequence
<220> FEATURE:
<223> OTHER INFORMATION: oligonucleotide primer

<400> SEQUENCE: 34

```
gtcgatgatg accttggtcc                                                  20
```

<210> SEQ ID NO 35
<211> LENGTH: 24
<212> TYPE: DNA
<213> ORGANISM: Artificial sequence
<220> FEATURE:
<223> OTHER INFORMATION: oligonucleotide primer

<400> SEQUENCE: 35

```
cggctgttcg agtggcaaca agtc                                             24
```

<210> SEQ ID NO 36
<211> LENGTH: 23
<212> TYPE: DNA
<213> ORGANISM: Artificial sequence
<220> FEATURE:
<223> OTHER INFORMATION: oligonucleotide primer

<400> SEQUENCE: 36

```
ccgtcgatga tgaccttggt ccc                                              23
```

<210> SEQ ID NO 37
<211> LENGTH: 1020
<212> TYPE: DNA
<213> ORGANISM: Mycobacterium avium

<400> SEQUENCE: 37

```
ccacgcccga cggccaggct gatcccgatc accagcagcg gcagcagcgc ggtgaacacc      60
gaccggtaca cgatcagcag gatcagcgcg atcagcccgg cggtggcgat cgagatgaac     120
accaggtcgt gctcggctga ggcgatctga tcggcgaacg tggccggtgg ccctgtcaca     180
taggccgtgg tggacgtgtt ggcgaatgcc gtgtcggtga atcgcgcac ggcttgcacg      240
gattcggccg cggtgggatc accgagcgtg ccggccaccc cgaccggcag ataccaggcc     300
```

```
ttgccgtcac cgctgaccgc ctgggttctg gtgaccgggt cggccagcag atcctggacc    360
agcaggacat ggtcgtgatc ggcgcgcaac cgccctacca gatcctgata gcgcagctga    420
ttatcggggg tcagaccggc cgggtcttgc atcgcgacga acagcatcgt cttggacccc    480
tgctcaccga acgcctcact catgcggtcc acggtctgaa acgagggcac atcacgcggg    540
atcagatcga ccgattgttg gcgcaccacc gtctccaact gcgggaacag cagcgccagc    600
accaccgcgg ccgcgatcca tccaccgatc actaatgcct tgtggcccac cgtgaacgcc    660
gcgagccgac ccagccgggc gctgtattcc gaagatccgg acagatcgac gccgcgccgg    720
ccacgggaag gcccagcatc tccggttcga tcgcccatcc ccacgcctcc caagaaacga    780
aactatcggt atcgctacga tactaatagt cccacacgag gatcggaagg gccgcgccga    840
cctttcgggc catggttggg gctgggcgcg gtgggggtga attaacttgc ggtgtcctca    900
gattcgtcgt cgggcaggtc gtggcgcacc acccgcaccc gcccgcgggg caggcatgcc    960
atgtagccgt ggcgtttgcc gtagagctcc caggaggtcg cggcctcctg gggggcgaca   1020
```

<210> SEQ ID NO 38
<211> LENGTH: 959
<212> TYPE: DNA
<213> ORGANISM: Mycobacterium avium

<400> SEQUENCE: 38

```
accatggcca gaaaggccag ggccacggtg ccggccgagg ccaggatgac tcggccgatg     60
ctggcggtgg ccgcgatgac cgcctgctcg gcgggcacct gggcgcggcg ttgttcgtgg    120
tagcggctga tcagaaacac ggtgtagtcg gtgccggcgt gtggggcgag cagctcgact    180
gaggtgcggc agcgggcgat gacggcttca ccgatccctt cctccacgcc gcgcaggatc    240
atggtggcgg tgtcggggtc gccgacgagg aatcgcaccg ccacgccgcg ggcggcggcg    300
tcgagcaggg tgtcgaggaa tccgtcgagg gtgtcgaaca ggaacgtggc ggccagcacg    360
aggatgtcga tgctggtggt ggcgtcggcg aaatgctgct gccacgcgct gatcggtagc    420
tgggtgcggc tggcatacag ggtcgcggtg aacgggccac ttggtgacat ggtcgccaat    480
gcgctcgcca tagtaggcga gtactgattg ggccacagat cgtgcggcgt gcagcccagc    540
agcgtggctg cgcgccgcgc gttgtcctcg cggatgttgt agttggtgtt ggacagccag    600
cggcgcaccg tcttgacatc cacgctcatc gcggtggcaa agcgctgcgg ggacagtccc    660
ttggcctgca gccgctgcat gaggcgattg ttggggatcg cggccgcctt gccgtcgtga    720
tcgtccatcg tctcagcgca catctttccg tgtcgtctcc gtgtatcgcc agcgcgtggc    780
gtctagtttg ccatgcgcgt ggtgccaccc cgcggcggtg atgcccacgt gatgtccacg    840
ggtatgtccc ggtggtgtcc ggaatgtcgc cggcgatgtc ggcaatgccg ctagatgtcc    900
ctggctacgt cggtggtgtc cacgtgaact gagttcagcg ccgcaagggc gcatacggt     959
```

<210> SEQ ID NO 39
<211> LENGTH: 896
<212> TYPE: DNA
<213> ORGANISM: Mycobacterium avium

<400> SEQUENCE: 39

```
cgtgggcatc accgccgcgg cattcggtgc agttgctggc gttggatgac actggcggcg     60
aagtgctcaa tgtgacggtg gccggtgacc cgaacgtcgg ggtcacccaa ccggtctcgg    120
tgaccagcct ggtggccatc ccgtgggcgc aaggcgatcg cagtggtgtg gccttccgcg    180
ctgatgccat caccggcgcc acagccggcg ccccggcggg tgagccgggg tcgcgcaccc    240
```

```
agaaatagca cccgctgccg aggcgcgaca ccagcacgtg ccgcgcctcg gcccgggtcc    300
gccgtcgacc actggctcgt ccacgcacac acggagaaca caccgtcatg gcatcaaaca    360
ataagaacac caacaacact caatcggaca atgacgactg gttcggcgat ctggtcatat    420
cactgttgac cgccgcggga tatctgctgt ggtgggccgt gctgttccca gcgatcagtg    480
tcccgatcat cgccagcctc actctcggca tcacccacgg accccgcgcc gggatcgtcg    540
gtgccatcgc gttcggcgcc ggatatatgg ggtgggcttg gctagaccca ggctcgtttt    600
gctcgtgggt gaccgaacct gtacggcgcc gctggttgac ctggtcgcgc tacacccgca    660
cctggggaat cgacgtgcac cctgcacggc ctgaccgcca aacttggtga gcgcaccctg    720
actccgaccc tgcgcaccgt cacgatcggt agaaccaccg atgtgttggc ggtgcggatc    780
gtcaccggcc aatccctaac taactggcac caacaatccg aggcgctggc cgcggcctgg    840
cgcgccgacc ggatcaccat caccgccacc acacccgggg aactacgcat cgcgct        896
```

<210> SEQ ID NO 40
<211> LENGTH: 744
<212> TYPE: DNA
<213> ORGANISM: Mycobacterium avium

<400> SEQUENCE: 40

```
acgatccgca ccgccaacac atcggtggtt ctaccgatcg tgacggtgcg cagggtcgga     60
gtcagggtgc gctcaccaag tttggcggtc aggccgtgca gggtgcacgt cgattcccag    120
gtgcgggtgt agcgcgacca ggtcaaccag cggcgccgta caggttcggt cacccacgag    180
caaaacgagc ctgggtctag ccaagcccac cccatatatc cggcgccgaa cgcgatggca    240
ccgacgatcc cggcgcgggg tccgtgggtg atgccgagag tgaggctggc gatgatcggg    300
acactgatcg ctgggaacag cacggcccac cacagcagat atcccgcggc ggtcaacagt    360
gatatgacca gatcgccgaa ccagtcgtca ttgtccgatt gagtgttgtt ggtgttctta    420
ttgtttgatg ccatgacggt gtgttctccg tgtgtgcgtg gacgagccag tggtcgacgg    480
cggacccggg ccgaggcgcg gcacgtgctg gtgtcgcgcc tcggcagcgg gtgctatttc    540
tgggtgcgcg accccggctc acccgccggg gcgccggctg tggcgccggt gatggcatca    600
gcgcggaagg ccacaccact gcgatcgcct tgcgcccacg ggatggccac caggctggtc    660
accgagaccg gttgggtgac ccccgacgttc gggtcaccgg ccaccgtcac attgagcact    720
tcgccgccag tgtcatccaa cgcc                                            744
```

<210> SEQ ID NO 41
<211> LENGTH: 790
<212> TYPE: DNA
<213> ORGANISM: Mycobacterium avium

<400> SEQUENCE: 41

```
cgacaaccac ctcgttgtcg ttggcgcacc cgcatcgtga actaccgtga gcaagggcgt     60
accttcccga accagcgcgc caacgccggc tcttgatcag acctatgaca ttcagatcat    120
cctcgggaag gtgcgcccac tttcacgcca cctcgccaag gctcatccac aggttctgat    180
cattgctctt gtgctgtcgg ctatgtgccg tgactttgat cgagttgcca gacctcggat    240
cttggagcat ctcatcctca cggatctccg acagcggcac ccgctctact gcatgttccg    300
aaactcatgc ctctcggatc gtcgtggcag gtcggctgcg tcgacccttt ccggggatcg    360
tcccggcgat caccgaaccc aggcgcgatc gcaggtgctc tgagccatga gtagccgacc    420
```

| | |
|---|---|
| ggccctctgg tagcagcggt acgctcgtca aatccctcga actaggaaag gtggagggat | 480 |
| gccaatgccg agaccccgg gcgcttccgc ggcggcccga atcgcgttcg gttaaatgtg | 540 |
| gcgatccacg agcagcttct cgccgccgtc gacggccggc gcgggataga agccaccgac | 600 |
| tgtctgtgcg acgcttgcgt ggccctcctc gaggttgacg cggcggcgat ttcgctcgtc | 660 |
| ttcgacggcg cgagcagcgg cacactggga tccagcagcc tggcggcgcg cctgtacgac | 720 |
| gaattgcagt tcacgctcgg cgagggaccg tgcctggact ctgtcacgcg gcggattcct | 780 |
| atagtattgg | 790 |

<210> SEQ ID NO 42
<211> LENGTH: 569
<212> TYPE: DNA
<213> ORGANISM: Mycobacterium avium

<400> SEQUENCE: 42

| | |
|---|---|
| gcgaacgtca agaacgcgaa ccagagtgct cgacgctttc cgagcactgg cacgagaaca | 60 |
| gtgatgcgat atgcgaccac tctctgcgcg ccgcgtcacg cggaacgggg ttgaaaggtg | 120 |
| gatcaggacg caaacgcgtt aaagaagtcc aatgtggatc cgcgactacg gttctgcgct | 180 |
| tcgttctttg gagacggcct taaccccttat caaccgcgta cgcaaggcca gacggcgatt | 240 |
| ctccttgtct ttcaaaaacg ccagcatgcg cctgcaagtc tcccaccctg caacccagaa | 300 |
| gtacattggc agccgttttc tgaactcttt atcagtcccc tgcctcatgc tgaagccggt | 360 |
| catgtcgttg tattcggaaa tcacgacgtc catgtagcgg gtaatcagcg ccgggttgga | 420 |
| gaagcagcga atattgaagt cccagtccgc ccagactcgg tagcgcaggt tgtaagggcc | 480 |
| gatgccgtcg aaaagctcac ggcggtaaaa gatcgattgg tggcacaaat tcgtctcaaa | 540 |
| taggaggcgg tcgaggtcga aggtccgg | 569 |

<210> SEQ ID NO 43
<211> LENGTH: 19
<212> TYPE: DNA
<213> ORGANISM: Artificial sequence
<220> FEATURE:
<223> OTHER INFORMATION: oligonucleotide primer

<400> SEQUENCE: 43

| | |
|---|---|
| gcctcccaag aaacgaaac | 19 |

<210> SEQ ID NO 44
<211> LENGTH: 20
<212> TYPE: DNA
<213> ORGANISM: Artificial sequence
<220> FEATURE:
<223> OTHER INFORMATION: oligonucleotide primer

<400> SEQUENCE: 44

| | |
|---|---|
| acgacgaatc tgaggacacc | 20 |

<210> SEQ ID NO 45
<211> LENGTH: 18
<212> TYPE: DNA
<213> ORGANISM: Artificial sequence
<220> FEATURE:
<223> OTHER INFORMATION: oligonucleotide primer

<400> SEQUENCE: 45

| | |
|---|---|
| cacacgagga tcggaagg | 18 |

```
<210> SEQ ID NO 46
<211> LENGTH: 18
<212> TYPE: DNA
<213> ORGANISM: Artificial sequence
<220> FEATURE:
<223> OTHER INFORMATION: oligonucleotide primer

<400> SEQUENCE: 46
caaacgccac ggctacat                                                 18

<210> SEQ ID NO 47
<211> LENGTH: 18
<212> TYPE: DNA
<213> ORGANISM: Artificial sequence
<220> FEATURE:
<223> OTHER INFORMATION: oligonucleotide primer

<400> SEQUENCE: 47
gaatgccgtg tcggtgag                                                 18

<210> SEQ ID NO 48
<211> LENGTH: 18
<212> TYPE: DNA
<213> ORGANISM: Artificial sequence
<220> FEATURE:
<223> OTHER INFORMATION: oligonucleotide primer

<400> SEQUENCE: 48
atctggtagg gcggttgc                                                 18

<210> SEQ ID NO 49
<211> LENGTH: 20
<212> TYPE: DNA
<213> ORGANISM: Artificial sequence
<220> FEATURE:
<223> OTHER INFORMATION: oligonucleotide primer

<400> SEQUENCE: 49
acacgatcag caggatcagc                                               20

<210> SEQ ID NO 50
<211> LENGTH: 18
<212> TYPE: DNA
<213> ORGANISM: Artificial sequence
<220> FEATURE:
<223> OTHER INFORMATION: oligonucleotide primer

<400> SEQUENCE: 50
attcgccaac acgtccac                                                 18

<210> SEQ ID NO 51
<211> LENGTH: 18
<212> TYPE: DNA
<213> ORGANISM: Artificial sequence
<220> FEATURE:
<223> OTHER INFORMATION: oligonucleotide primer

<400> SEQUENCE: 51
gcaaccgccc taccagat                                                 18

<210> SEQ ID NO 52
<211> LENGTH: 19
<212> TYPE: DNA
<213> ORGANISM: Artificial sequence
<220> FEATURE:
<223> OTHER INFORMATION: oligonucleotide primer
```

```
<400> SEQUENCE: 52
gtgatgtgcc ctcgtttca                                              19

<210> SEQ ID NO 53
<211> LENGTH: 21
<212> TYPE: DNA
<213> ORGANISM: Artificial sequence
<220> FEATURE:
<223> OTHER INFORMATION: oligonucleotide primer

<400> SEQUENCE: 53
gatccatcca ccgatcacta a                                           21

<210> SEQ ID NO 54
<211> LENGTH: 18
<212> TYPE: DNA
<213> ORGANISM: Artificial sequence
<220> FEATURE:
<223> OTHER INFORMATION: oligonucleotide primer

<400> SEQUENCE: 54
atcgaaccgg agatgctg                                               18

<210> SEQ ID NO 55
<211> LENGTH: 19
<212> TYPE: DNA
<213> ORGANISM: Artificial sequence
<220> FEATURE:
<223> OTHER INFORMATION: oligonucleotide primer

<400> SEQUENCE: 55
cttcaccgat cccttcctc                                              19

<210> SEQ ID NO 56
<211> LENGTH: 19
<212> TYPE: DNA
<213> ORGANISM: Artificial sequence
<220> FEATURE:
<223> OTHER INFORMATION: oligonucleotide primer

<400> SEQUENCE: 56
caccagcatc gacatcctc                                              19

<210> SEQ ID NO 57
<211> LENGTH: 18
<212> TYPE: DNA
<213> ORGANISM: Artificial sequence
<220> FEATURE:
<223> OTHER INFORMATION: oligonucleotide primer

<400> SEQUENCE: 57
ccgaggccag gatgactc                                               18

<210> SEQ ID NO 58
<211> LENGTH: 19
<212> TYPE: DNA
<213> ORGANISM: Artificial sequence
<220> FEATURE:
<223> OTHER INFORMATION: oligonucleotide primer

<400> SEQUENCE: 58
gaggaaggga tcggtgaag                                              19

<210> SEQ ID NO 59
<211> LENGTH: 20
```

```
<212> TYPE: DNA
<213> ORGANISM: Artificial sequence
<220> FEATURE:
<223> OTHER INFORMATION: oligonucleotide primer

<400> SEQUENCE: 59
tcttgacatc cacgctcatc                                              20

<210> SEQ ID NO 60
<211> LENGTH: 19
<212> TYPE: DNA
<213> ORGANISM: Artificial sequence
<220> FEATURE:
<223> OTHER INFORMATION: oligonucleotide primer

<400> SEQUENCE: 60
acggagacga cacggaaag                                               19

<210> SEQ ID NO 61
<211> LENGTH: 20
<212> TYPE: DNA
<213> ORGANISM: Artificial sequence
<220> FEATURE:
<223> OTHER INFORMATION: oligonucleotide primer

<400> SEQUENCE: 61
gcggatgttg tagttggtgt                                              20

<210> SEQ ID NO 62
<211> LENGTH: 20
<212> TYPE: DNA
<213> ORGANISM: Artificial sequence
<220> FEATURE:
<223> OTHER INFORMATION: oligonucleotide primer

<400> SEQUENCE: 62
aagatgtgcg ctgagacgat                                              20

<210> SEQ ID NO 63
<211> LENGTH: 19
<212> TYPE: DNA
<213> ORGANISM: Artificial sequencer
<220> FEATURE:
<223> OTHER INFORMATION: oligonucleotide primer

<400> SEQUENCE: 63
atacagggtc gcggtgaac                                               19

<210> SEQ ID NO 64
<211> LENGTH: 22
<212> TYPE: DNA
<213> ORGANISM: Artificial sequence
<220> FEATURE:
<223> OTHER INFORMATION: oligonucleotide primer

<400> SEQUENCE: 64
tccaacacca actacaacat cc                                           22

<210> SEQ ID NO 65
<211> LENGTH: 20
<212> TYPE: DNA
<213> ORGANISM: Artificial sequence
<220> FEATURE:
<223> OTHER INFORMATION: oligonucleotide primer

<400> SEQUENCE: 65
```
ccgtgtcgtc tccgtgtatc                                              20

<210> SEQ ID NO 66
<211> LENGTH: 20
<212> TYPE: DNA
<213> ORGANISM: Artificial sequence
<220> FEATURE:
<223> OTHER INFORMATION: oligonucleotide primer

<400> SEQUENCE: 66
cgtagccagg gacatctagc                                              20

<210> SEQ ID NO 67
<211> LENGTH: 18
<212> TYPE: DNA
<213> ORGANISM: Artificial sequence
<220> FEATURE:
<223> OTHER INFORMATION: oligonucleotide primer

<400> SEQUENCE: 67
caccggccaa tccctaac                                                18

<210> SEQ ID NO 68
<211> LENGTH: 18
<212> TYPE: DNA
<213> ORGANISM: Artificial sequence
<220> FEATURE:
<223> OTHER INFORMATION: oligonucleotide primer

<400> SEQUENCE: 68
agcgcgatgc gtagttcc                                                18

<210> SEQ ID NO 69
<211> LENGTH: 19
<212> TYPE: DNA
<213> ORGANISM: Artificial sequence
<220> FEATURE:
<223> OTHER INFORMATION: oligonucleotide primer

<400> SEQUENCE: 69
cgaagtgctc aatgtgacg                                               19

<210> SEQ ID NO 70
<211> LENGTH: 19
<212> TYPE: DNA
<213> ORGANISM: Artificial sequence
<220> FEATURE:
<223> OTHER INFORMATION: oligonucleotide primer

<400> SEQUENCE: 70
cagcgggtgc tatttctgg                                               19

<210> SEQ ID NO 71
<211> LENGTH: 18
<212> TYPE: DNA
<213> ORGANISM: Artificial sequence
<220> FEATURE:
<223> OTHER INFORMATION: oligonucleotide primer

<400> SEQUENCE: 71
aggctcgttt tgctcgtg                                                18

<210> SEQ ID NO 72
<211> LENGTH: 21
<212> TYPE: DNA
<213> ORGANISM: Artificial sequence
<220> FEATURE:
<223> OTHER INFORMATION: oligonucleotide primer

<400> SEQUENCE: 72
tgccagttag ttagggattg g    21

<210> SEQ ID NO 73
<211> LENGTH: 20
<212> TYPE: DNA
<213> ORGANISM: Artificial sequence
<220> FEATURE:
<223> OTHER INFORMATION: oligonucleotide primer

<400> SEQUENCE: 73
cactcaatcg gacaatgacg    20

<210> SEQ ID NO 74
<211> LENGTH: 18
<212> TYPE: DNA
<213> ORGANISM: Artificial sequence
<220> FEATURE:
<223> OTHER INFORMATION: oligonucleotide primer

<400> SEQUENCE: 74
gtgggtgatg ccgagagt    18

<210> SEQ ID NO 75
<211> LENGTH: 18
<212> TYPE: DNA
<213> ORGANISM: Artificial sequence
<220> FEATURE:
<223> OTHER INFORMATION: oligonucleotide primer

<400> SEQUENCE: 75
gtgggtgatg ccgagagt    18

<210> SEQ ID NO 76
<211> LENGTH: 19
<212> TYPE: DNA
<213> ORGANISM: Artificial sequence
<220> FEATURE:
<223> OTHER INFORMATION: oligonucleotide primer

<400> SEQUENCE: 76
cggacaatga cgactggtt    19

<210> SEQ ID NO 77
<211> LENGTH: 18
<212> TYPE: DNA
<213> ORGANISM: Artificial sequence
<220> FEATURE:
<223> OTHER INFORMATION: oligonucleotide primer

<400> SEQUENCE: 77
cacgtcgatt cccaggtg    18

<210> SEQ ID NO 78
<211> LENGTH: 19
<212> TYPE: DNA
<213> ORGANISM: Artificial sequence
<220> FEATURE:
<223> OTHER INFORMATION: oligonucleotide primer

<400> SEQUENCE: 78
atcatcgcca gcctcactc    19

<210> SEQ ID NO 79
<211> LENGTH: 18
<212> TYPE: DNA
<213> ORGANISM: Artificial sequence
<220> FEATURE:
<223> OTHER INFORMATION: oligonucleotide primer

<400> SEQUENCE: 79
gccgaaccag tcgtcatt                                                 18

<210> SEQ ID NO 80
<211> LENGTH: 18
<212> TYPE: DNA
<213> ORGANISM: Artificial sequence
<220> FEATURE:
<223> OTHER INFORMATION: oligonucleotide primer

<400> SEQUENCE: 80
cgcacccaga aatagcac                                                 18

<210> SEQ ID NO 81
<211> LENGTH: 18
<212> TYPE: DNA
<213> ORGANISM: Artificial sequence
<220> FEATURE:
<223> OTHER INFORMATION: oligonucleotide primer

<400> SEQUENCE: 81
agcgggtgct atttctgg                                                 18

<210> SEQ ID NO 82
<211> LENGTH: 18
<212> TYPE: DNA
<213> ORGANISM: Artificial sequence
<220> FEATURE:
<223> OTHER INFORMATION: oligonucleotide primer

<400> SEQUENCE: 82
cggcgaagtg ctcaatgt                                                 18

<210> SEQ ID NO 83
<211> LENGTH: 20
<212> TYPE: DNA
<213> ORGANISM: Artificial sequence
<220> FEATURE:
<223> OTHER INFORMATION: oligonucleotide primer

<400> SEQUENCE: 83
atcgtgaact accgtgagca                                               20

<210> SEQ ID NO 84
<211> LENGTH: 20
<212> TYPE: DNA
<213> ORGANISM: Artificial sequence
<220> FEATURE:
<223> OTHER INFORMATION: oligonucleotide primer

<400> SEQUENCE: 84
gaacctgtgg atgagccttg                                               20

<210> SEQ ID NO 85
<211> LENGTH: 20
<212> TYPE: DNA
<213> ORGANISM: Artificial sequence
<220> FEATURE:
<223> OTHER INFORMATION: oligonucleotide primer

```
<400> SEQUENCE: 85
aggctcatcc acaggttctg                                              20

<210> SEQ ID NO 86
<211> LENGTH: 18
<212> TYPE: DNA
<213> ORGANISM: Artificial sequence
<220> FEATURE:
<223> OTHER INFORMATION: oligonucleotide primer

<400> SEQUENCE: 86
acgatccgag aggcatga                                                18

<210> SEQ ID NO 87
<211> LENGTH: 20
<212> TYPE: DNA
<213> ORGANISM: Artificial sequence
<220> FEATURE:
<223> OTHER INFORMATION: oligonucleotide primer

<400> SEQUENCE: 87
ctaggaaagg tggagggatg                                              20

<210> SEQ ID NO 88
<211> LENGTH: 20
<212> TYPE: DNA
<213> ORGANISM: Artificial sequence
<220> FEATURE:
<223> OTHER INFORMATION: oligonucleotide primer

<400> SEQUENCE: 88
acagtcggtg gcttctatcc                                              20

<210> SEQ ID NO 89
<211> LENGTH: 18
<212> TYPE: DNA
<213> ORGANISM: Artificial sequence
<220> FEATURE:
<223> OTHER INFORMATION: oligonucleotide primer

<400> SEQUENCE: 89
gcggtacgct cgtcaaat                                                18

<210> SEQ ID NO 90
<211> LENGTH: 18
<212> TYPE: DNA
<213> ORGANISM: Artificial sequence
<220> FEATURE:
<223> OTHER INFORMATION: oligonucleotide primer

<400> SEQUENCE: 90
ctcgtggatc gccacatt                                                18

<210> SEQ ID NO 91
<211> LENGTH: 20
<212> TYPE: DNA
<213> ORGANISM: Artificial sequence
<220> FEATURE:
<223> OTHER INFORMATION: oligonucleotide primer

<400> SEQUENCE: 91
acccgctcta ctgcatgttc                                              20

<210> SEQ ID NO 92
```

-continued

```
<211> LENGTH: 19
<212> TYPE: DNA
<213> ORGANISM: Artificial sequence
<220> FEATURE:
<223> OTHER INFORMATION: oligonucleotide primer

<400> SEQUENCE: 92
gtcggctact catggctca                                                   19

<210> SEQ ID NO 93
<211> LENGTH: 20
<212> TYPE: DNA
<213> ORGANISM: Artificial sequence
<220> FEATURE:
<223> OTHER INFORMATION: oligonucleotide primer

<400> SEQUENCE: 93
tttatcagtc ccctgcctca                                                  20

<210> SEQ ID NO 94
<211> LENGTH: 20
<212> TYPE: DNA
<213> ORGANISM: Artificial sequence
<220> FEATURE:
<223> OTHER INFORMATION: oligonucleotide primer

<400> SEQUENCE: 94
tattcgctgc ttctccaacc                                                  20

<210> SEQ ID NO 95
<211> LENGTH: 19
<212> TYPE: DNA
<213> ORGANISM: Artificial sequence
<220> FEATURE:
<223> OTHER INFORMATION: oligonucleotide primer

<400> SEQUENCE: 95
gcttcgttct ttggagacg                                                   19

<210> SEQ ID NO 96
<211> LENGTH: 20
<212> TYPE: DNA
<213> ORGANISM: Artificial sequence
<220> FEATURE:
<223> OTHER INFORMATION: oligonucleotide primer

<400> SEQUENCE: 96
tgaggcaggg gactgataaa                                                  20

<210> SEQ ID NO 97
<211> LENGTH: 18
<212> TYPE: DNA
<213> ORGANISM: Artificial sequence
<220> FEATURE:
<223> OTHER INFORMATION: oligonucleotide primer

<400> SEQUENCE: 97
gaacggggtt gaaaggtg                                                    18

<210> SEQ ID NO 98
<211> LENGTH: 18
<212> TYPE: DNA
<213> ORGANISM: Artificial sequence
<220> FEATURE:
<223> OTHER INFORMATION: oligonucleotide primer

<400> SEQUENCE: 98
```

-continued gcagggtggg agacttgc                                              18

<210> SEQ ID NO 99
<211> LENGTH: 20
<212> TYPE: DNA
<213> ORGANISM: Artificial sequence
<220> FEATURE:
<223> OTHER INFORMATION: oligonucleotide primer

<400> SEQUENCE: 99
cgtccatgta gcgggtaatc                                            20

<210> SEQ ID NO 100
<211> LENGTH: 19
<212> TYPE: DNA
<213> ORGANISM: Artificial sequence
<220> FEATURE:
<223> OTHER INFORMATION: oligonucleotide primer

<400> SEQUENCE: 100
ctcgaccgcc tcctatttg                                             19

<210> SEQ ID NO 101
<211> LENGTH: 146
<212> TYPE: DNA
<213> ORGANISM: Artificial sequence
<220> FEATURE:
<223> OTHER INFORMATION: oligonucleotide probe

<400> SEQUENCE: 101
gcctcccaag aaacgaaact atcggtatcg ctacgatact aatagtccca cacgaggatc    60
ggaagggccg cgccgacctt tcgggccatg gttgggctg ggcgcggtgg gggtgaatta   120
acttgcggtg tcctcagatt cgtcgt                                     146

<210> SEQ ID NO 102
<211> LENGTH: 166
<212> TYPE: DNA
<213> ORGANISM: Artificial sequence
<220> FEATURE:
<223> OTHER INFORMATION: oligonucleotide probe

<400> SEQUENCE: 102
cacacgagga tcggaagggc cgcgccgacc tttcgggcca tggttggggc tgggcgcggt    60
gggggtgaat taacttgcgg tgtcctcaga ttcgtcgtcg ggcaggtcgt ggcgcaccac   120
ccgcacccgc ccgcggggca ggcatgccat gtagccgtgg cgtttg                166

<210> SEQ ID NO 103
<211> LENGTH: 200
<212> TYPE: DNA
<213> ORGANISM: Artificial sequence
<220> FEATURE:
<223> OTHER INFORMATION: oligonucleotide probe

<400> SEQUENCE: 103
gaatgccgtg tcggtgagat cgcgcacggc ttgcacggat tcggccgcgg tgggatcacc    60
gagcgtgccg gccaccccga ccggcagata ccaggccttg ccgtcaccgc tgaccgcctg   120
ggttctggtg accgggtcgg ccagcagatc ctggaccagc aggacatggt cgtgatcggc   180
gcgcaaccgc cctaccagat                                            200

<210> SEQ ID NO 104

```
<211> LENGTH: 140
<212> TYPE: DNA
<213> ORGANISM: Artificial sequence
<220> FEATURE:
<223> OTHER INFORMATION: oligonucleotide probe

<400> SEQUENCE: 104
acacgatcag caggatcagc gcgatcagcc cggcggtggc gatcgagatg aacaccaggt    60
cgtgctcggc tgaggcgatc tgatcggcga acgtggccgg tggccctgtc acataggccg   120
tggtggacgt gttggcgaat                                                140

<210> SEQ ID NO 105
<211> LENGTH: 150
<212> TYPE: DNA
<213> ORGANISM: Artificial sequence
<220> FEATURE:
<223> OTHER INFORMATION: oligonucleotide probe

<400> SEQUENCE: 105
gcaaccgccc taccagatcc tgatagcgca gctgattatc ggggtcaga ccggccgggt    60 cttgcatcgc gacgaacagc atcgtcttgg acccctgctc accgaacgcc tcactcatgc   120
ggtccacggt ctgaaacgag ggcacatcac                                     150

<210> SEQ ID NO 106
<211> LENGTH: 137
<212> TYPE: DNA
<213> ORGANISM: Artificial sequence
<220> FEATURE:
<223> OTHER INFORMATION: oligonucleotide probe

<400> SEQUENCE: 106
gatccatcca ccgatcacta atgccttgtg gcccaccgtg aacgccgcga gccgacccag    60
ccgggcgctg tattccgaag atccggacag atcgacgccg cgccggccac gggaaggccc   120
agcatctccg gttcgat                                                   137

<210> SEQ ID NO 107
<211> LENGTH: 173
<212> TYPE: DNA
<213> ORGANISM: Artificial sequence
<220> FEATURE:
<223> OTHER INFORMATION: oligonucleotide probe

<400> SEQUENCE: 107
cttcaccgat cccttcctcc acgccgcgca ggatcatggt ggcggtgtcg ggtcgccga    60 cgaggaatcg caccgccacg ccgcgggcgg cggcgtcgag cagggtgtcg aggaatccgt   120
cgagggtgtc gaacaggaac gtggcggcca gcacgaggat gtcgatgctg gtg          173

<210> SEQ ID NO 108
<211> LENGTH: 190
<212> TYPE: DNA
<213> ORGANISM: Artificial sequence
<220> FEATURE:
<223> OTHER INFORMATION: oligonucleotide probe

<400> SEQUENCE: 108
ccgaggccag gatgactcgg ccgatgctgg cggtggccgc gatgaccgcc tgctcggcgg    60
gcacctgggc gcggcgttgt tcgtggtagc ggctgatcag aaacacggtg tagtcggtgc   120
cggcgtgtgg ggcgagcagc tcgactgagg tgcggcagcg ggcgatgacg gcttcaccga   180
tcccttcctc                                                           190
```

```
<210> SEQ ID NO 109
<211> LENGTH: 152
<212> TYPE: DNA
<213> ORGANISM: Artificial sequence
<220> FEATURE:
<223> OTHER INFORMATION: oligonucleotide probe

<400> SEQUENCE: 109
tcttgacatc cacgctcatc gcggtggcaa agcgctgcgg ggacagtccc ttggcctgca      60
gccgctgcat gaggcgattg ttggggatcg cggccgcctt gccgtcgtga tcgtccatcg     120
tctcagcgca catctttccg tgtcgtctcc gt                                   152

<210> SEQ ID NO 110
<211> LENGTH: 177
<212> TYPE: DNA
<213> ORGANISM: Artificial sequence
<220> FEATURE:
<223> OTHER INFORMATION: oligonucleotide probe

<400> SEQUENCE: 110
gcggatgttg tagttggtgt tggacagcca gcggcgcacc gtcttgacat ccacgctcat      60
cgcggtggca aagcgctgcg gggacagtcc cttggcctgc agccgctgca tgaggcgatt     120
gttggggatc gcggccgcct tgccgtcgtg atcgtccatc gtctcagcgc acatctt        177

<210> SEQ ID NO 111
<211> LENGTH: 159
<212> TYPE: DNA
<213> ORGANISM: Artificial sequence
<220> FEATURE:
<223> OTHER INFORMATION: oligonucleotide probe

<400> SEQUENCE: 111
atacagggtc gcggtgaacg ggccacttgg tgacatggtc gccaatgcgc tcgccatagt      60
aggcgagtac tgattgggcc acagatcgtg cggcgtgcag cccagcagcg tggctgcgcg     120
ccgcgcgttg tcctcgcgga tgttgtagtt ggtgttgga                            159

<210> SEQ ID NO 112
<211> LENGTH: 162
<212> TYPE: DNA
<213> ORGANISM: Artificial sequence
<220> FEATURE:
<223> OTHER INFORMATION: oligonucleotide probe

<400> SEQUENCE: 112
ccgtgtcgtc tccgtgtatc gccagcgcgt ggcgtctagt ttgccatgcg cgtggtgcca      60
ccccgcggcg gtgatgccca cgtgatgtcc acgggtatgt cccggtggtg tccggaatgt     120
cgccggcgat gtcggcaatg ccgctagatg tccctggcta cg                        162

<210> SEQ ID NO 113
<211> LENGTH: 114
<212> TYPE: DNA
<213> ORGANISM: Artificial sequence
<220> FEATURE:
<223> OTHER INFORMATION: oligonucleotide probe

<400> SEQUENCE: 113
caccggccaa tccctaacta actggcacca acaatccgag gcgctggccg cggcctggcg      60
cgccgaccgg atcaccatca ccgccaccac acccggggaa ctacgcatcg cgct           114
```

```
<210> SEQ ID NO 114
<211> LENGTH: 199
<212> TYPE: DNA
<213> ORGANISM: Artificial sequence
<220> FEATURE:
<223> OTHER INFORMATION: oligonucleotide probe

<400> SEQUENCE: 114
cgaagtgctc aatgtgacgg tggccggtga cccgaacgtc ggggtcaccc aaccggtctc      60
ggtgaccagc ctggtggcca tcccgtgggc gcaaggcgat cgcagtggtg tggccttccg     120
cgctgatgcc atcaccggcg ccacagccgg cgccccggcg ggtgagccgg ggtcgcgcac     180
ccagaaatag cacccgctg                                                  199

<210> SEQ ID NO 115
<211> LENGTH: 220
<212> TYPE: DNA
<213> ORGANISM: Artificial sequence
<220> FEATURE:
<223> OTHER INFORMATION: oligonucleotide probe

<400> SEQUENCE: 115
aggctcgttt tgctcgtggg tgaccgaacc tgtacggcgc cgctggttga cctggtcgcg      60
ctacacccgc acctggggaa tcgacgtgca ccctgcacgg cctgaccgcc aaacttggtg     120
agcgcaccct gactccgacc ctgcgcaccg tcacgatcgg tagaaccacc gatgtgttgg     180
cggtgcggat cgtcaccggc caatccctaa ctaactggca                           220

<210> SEQ ID NO 116
<211> LENGTH: 142
<212> TYPE: DNA
<213> ORGANISM: Artificial sequence
<220> FEATURE:
<223> OTHER INFORMATION: oligonucleotide probe

<400> SEQUENCE: 116
cactcaatcg gacaatgacg actggttcgg cgatctggtc atatcactgt tgaccgccgc      60
gggatatctg ctgtggtggg ccgtgctgtt cccagcgatc agtgtcccga tcatcgccag     120
cctcactctc ggcatcaccc ac                                              142

<210> SEQ ID NO 117
<211> LENGTH: 134
<212> TYPE: DNA
<213> ORGANISM: Artificial sequence
<220> FEATURE:
<223> OTHER INFORMATION: oligonucleotide probe

<400> SEQUENCE: 117
gtgggtgatg ccgagagtga ggctggcgat gatcgggaca ctgatcgctg ggaacagcac      60
ggcccaccac agcagatatc ccgcggcggt caacagtgat atgaccagat cgccgaacca     120
gtcgtcattg tccg                                                       134

<210> SEQ ID NO 118
<211> LENGTH: 191
<212> TYPE: DNA
<213> ORGANISM: Artificial sequence
<220> FEATURE:
<223> OTHER INFORMATION: oligonucleotide probe

<400> SEQUENCE: 118
cacgtcgatt cccaggtgcg ggtgtagcgc gaccaggtca accagcggcg ccgtacaggt      60
```

```
tcggtcaccc acgagcaaaa cgagcctggg tctagccaag cccacccat  atatccggcg    120 ccgaacgcga tggcaccgac gatcccggcg cggggtccgt gggtgatgcc gagagtgagg    180
ctggcgatga t                                                         191

<210> SEQ ID NO 119
<211> LENGTH: 174
<212> TYPE: DNA
<213> ORGANISM: Artificial sequence
<220> FEATURE:
<223> OTHER INFORMATION: oligonucleotide probe

<400> SEQUENCE: 119
gccgaaccag tcgtcattgt ccgattgagt gttgttggtg ttcttattgt ttgatgccat    60
gacggtgtgt tctccgtgtg tgcgtggacg agccagtggt cgacggcgga cccgggccga    120
ggcgcggcac gtgctggtgt cgcgcctcgg cagcgggtgc tatttctggg tgcg          174

<210> SEQ ID NO 120
<211> LENGTH: 201
<212> TYPE: DNA
<213> ORGANISM: Artificial sequence
<220> FEATURE:
<223> OTHER INFORMATION: oligonucleotide probe

<400> SEQUENCE: 120
agcgggtgct atttctgggt gcgcgacccc ggctcacccg ccggggcgcc ggctgtggcg    60
ccggtgatgg catcagcgcg gaaggccaca ccactgcgat cgccttgcgc ccacgggatg    120
gccaccaggc tggtcaccga gaccggttgg gtgacccga  cgttcgggtc accggccacc    180
gtcacattga gcacttcgcc g                                              201

<210> SEQ ID NO 121
<211> LENGTH: 143
<212> TYPE: DNA
<213> ORGANISM: Artificial sequence
<220> FEATURE:
<223> OTHER INFORMATION: oligonucleotide probe

<400> SEQUENCE: 121
atcgtgaact accgtgagca agggcgtacc ttcccgaacc agcgcgccaa cgccggctct    60
tgatcagacc tatgacattc agatcatcct cgggaaggtg cgcccacttt cacgccacct    120
cgccaaggct catccacagg ttc                                            143

<210> SEQ ID NO 122
<211> LENGTH: 164
<212> TYPE: DNA
<213> ORGANISM: Artificial sequence
<220> FEATURE:
<223> OTHER INFORMATION: oligonucleotide probe

<400> SEQUENCE: 122
aggctcatcc acaggttctg atcattgctc ttgtgctgtc ggctatgtgc cgtgactttg    60
atcgagttgc cagacctcgg atcttggagc atctcatcct cacggatctc cgacagcggc    120
acccgctcta ctgcatgttc cgaaactcat gcctctcgga tcgt                     164

<210> SEQ ID NO 123
<211> LENGTH: 142
<212> TYPE: DNA
<213> ORGANISM: Artificial sequence
<220> FEATURE:
```

<223> OTHER INFORMATION: oligonucleotide probe

<400> SEQUENCE: 123
ctaggaaagg tggagggatg ccaatgccga accccccggg cgcttccgcg gcggcccgaa    60
tcgcgttcgg ttaaatgtgg cgatccacga gcagcttctc gccgccgtcg acggccggcg    120
cgggatagaa gccaccgact gt    142

<210> SEQ ID NO 124
<211> LENGTH: 117
<212> TYPE: DNA
<213> ORGANISM: Artificial sequence
<220> FEATURE:
<223> OTHER INFORMATION: oligonucleotide probe

<400> SEQUENCE: 124
gcggtacgct cgtcaaatcc ctcgaactag gaaaggtgga gggatgccaa tgccgagacc    60
cccgggcgct ccgcggcgg cccgaatcgc gttcggttaa atgtggcgat ccacgag    117

<210> SEQ ID NO 125
<211> LENGTH: 141
<212> TYPE: DNA
<213> ORGANISM: Artificial sequence
<220> FEATURE:
<223> OTHER INFORMATION: oligonucleotide probe

<400> SEQUENCE: 125
acccgctcta ctgcatgttc cgaaactcat gcctctcgga tcgtcgtggc aggtcggctg    60
cgtcgaccct ttccggggat cgtcccggcg atcaccgaac ccaggcgcga tcgcaggtgc    120
tctgagccat gagtagccga c    141

<210> SEQ ID NO 126
<211> LENGTH: 106
<212> TYPE: DNA
<213> ORGANISM: Artificial sequence
<220> FEATURE:
<223> OTHER INFORMATION: oligonucleotide probe

<400> SEQUENCE: 126
tttatcagtc ccctgcctca tgctgaagcc ggtcatgtcg ttgtattcgg aaatcacgac    60
gtccatgtag cgggtaatca gcgccgggtt ggagaagcag cgaata    106

<210> SEQ ID NO 127
<211> LENGTH: 170
<212> TYPE: DNA
<213> ORGANISM: Artificial sequence
<220> FEATURE:
<223> OTHER INFORMATION: oligonucleotide probe

<400> SEQUENCE: 127
gcttcgttct ttggagacgg ccttaaccct tatcaaccgc gtacgcaagg ccagacggcg    60
attctccttg tctttcaaaa acgccagcat gcgcctgcaa gtctcccacc ctgcaaccca    120
gaagtacatt ggcagccgtt ttctgaactc tttatcagtc ccctgcctca    170

<210> SEQ ID NO 128
<211> LENGTH: 189
<212> TYPE: DNA
<213> ORGANISM: Artificial sequence
<220> FEATURE:
<223> OTHER INFORMATION: oligonucleotide probe

<400> SEQUENCE: 128
gaacggggtt gaaaggtgga tcaggacgca aacgcgttaa agaagtccaa tgtggatccg 60
cgactacggt tctgcgcttc gttctttgga gacggcctta acccttatca accgcgtacg 120
caaggccaga cggcgattct ccttgtcttt caaaaacgcc agcatgcgcc tgcaagtctc 180
ccaccctgc 189

<210> SEQ ID NO 129
<211> LENGTH: 169
<212> TYPE: DNA
<213> ORGANISM: Artificial sequence
<220> FEATURE:
<223> OTHER INFORMATION: oligonucleotide probe

<400> SEQUENCE: 129
cgtccatgta gcgggtaatc agcgccgggt tggagaagca gcgaatattg aagtcccagt 60
ccgcccagac tcggtagcgc aggttgtaag ggccgatgcc gtcgaaaagc tcacggcggt 120
aaaagatcga ttggtggcac aaattcgtct caaataggag gcggtcgag 169

<210> SEQ ID NO 130
<211> LENGTH: 833
<212> TYPE: DNA
<213> ORGANISM: Mycobacterium avium

<400> SEQUENCE: 130
tggcagcatc gccccgccgc gtaggagcag agacttcaca gacgcgcgac gccttgctcg 60
aggccgttgc gcagatgatg ctggaggagg gatatgcgag cgtcacgtat cgcgccttgg 120
ccgcgaaggc tggcgtgacg ccaagcctcg tgcagtacta cttcccctcg ctggatgaca 180
tcttcgtcgc cgccattcgc cgctactccg agcgcaacct gcaatggttg accgaggaac 240
ttcagcggcg agccgacgac ccacttcatg cgctgtggga gagcagctgg cacgagtcga 300
cgagtgcgct gatgacggag ttcatggcac ttggcaatca ccgcaaatcg attcgttccg 360
agatcgccgc cgtgacggat agcatgcgca gagtccaggt cgaggcgctg gtggcgaaat 420
tcgggaacga cgcccggctc ctcgctgatc tttcgttcga tgccgtggtg ctgttgatca 480
acggcgttcc gaagctcctt gggttggagg aaagcgtggg cgtcgatacc gcccacgccg 540
aattgatcgc cgcgtgcgag cgctttctgg acgccgtcga acctcgagcc aagcctcgcc 600
gtcgcagtaa gaaggctccg actcgccgac gctgactcgt cgcggcgggc gcttcacggg 660
aggccttgtg accgcgctgt acgtccgtat agactggacg atcgtatagc aggtgcacgg 720
cgggtggaag gcgagcattg tgagtcgcgt ggcggtagta accggcggtg ggtcgggaat 780
cgggcgggcc atcgtcgaac gactggccca cgacggccat cgcgtcgctg tgt 833

<210> SEQ ID NO 131
<211> LENGTH: 955
<212> TYPE: DNA
<213> ORGANISM: Mycobacterium avium

<400> SEQUENCE: 131
atcaacgtcg ggccgacggt gttgagcgtc accagaggga tgggtgcgct cacccggcgc 60
gcctcctcgg cgaagatgaa ctgctcgatg gccgaaaacc ctcgtccacc atattctttg 120
ggccatccga cacccagcag gttggccgcc gccagggcgc ggacgcattc gcgcaccgcg 180
ggaccgccgt ccatctgctc gctgaccgcg gcgacgcgtt cgggcgtcat cacggtctga 240
agcgtcgcac ggatctcggc gcgcagctgc tgttgctccg gcgtgtattc cagatccatc 300

```
ggctcaggcc cccattcgca ccggcatgcg tttcaccccg gcaccatgg tggcccgcat      360 ccggtccacc tcgcccacca gctcgatgcg gggataccgg cgcagcagct cctcgaagaa      420
caccgtcgcc tccagtcgcg ccaattgtgc gcccacacaa gaatgttcac cgcagccgaa      480
ggcgatgtgc gggttcgggt ggcgggtcac atcgaattcc tcggagtccg ggccgaatac      540
gtcctcgtcc cggttggccg acccgtagag catcaccacc acctcgccgg cgcggatccg      600
ctgtccgcgg atttcgacgt cggcggtcgc ggtgcgggcc atgtgtacca cgggactgtt      660
ccaccgcaac atctcctcga ccgcaagcgg gatgcgggcg ggctcctcaa cgagcaggcg      720
gtattggtcg ggatgcgcga tcagggccag cgtcccccagc gcgatcaggt tgcgggtggt      780
ttcgttgccg gccaccagca gcagaaaggc gaaattgagc aggtcttcgt cggtcaaccg      840
gtgctcgtcg atctcggcct cggccagcac cgagagcagg tcggcgcgcg gccgcgcgcg      900
gcgtgccgcg atcagccgct ggaagtactc gtagagtgcc ggccgccacc gccgg           955
```

<210> SEQ ID NO 132
<211> LENGTH: 810
<212> TYPE: DNA
<213> ORGANISM: Mycobacterium avium
<400> SEQUENCE: 132

```
ggctttcaca ggaagcgatc tggacaagct tgaaaggtac ttgctcaatc ccgaccacgt       60
aactggggga ccgaaggcga agtggttcga acgaaacggg tgtcacccag tacggcataa      120
aatacaacca agtgatctcg atcgccggag cgaacggaag ggtcatagat gtgacgttcg      180
cctggatacg cggaaacgac ggtgtagtgc gcttggtgac ggcgatccct acgagcaaat      240
gagagaacgt aaagcgttga gacctcgaga gtatgacgtg atcaggctgc tgcggccgct      300 gccgaacac aacctgcctg ccggttcacg cgggactatc gtcatggatt acacgaagga      360
ttcggatagc actctcccgt ccgcgtacga ggtggagttt tcagatgccg acggcgtaac      420
ccaggcgctg gtcacgcttt ccggagatga cctggaagtc gtctggcggc cggatccaga      480
tgcgtagcga ctgtagttgc ggcccgattc agggccacat ggccgtattg tgttgggcca      540
caccgtcata gttgcggtgc gccctctcca cattggtgcg caattcggtg agcgcttctc      600
gcatttgttt gtcggctgct acccatcttt ggtggtactc gcgctcggcg tctgcgccgc      660
gacccagcca ggaaccgtgg agttcggcga tgcattggtc gacggccgcg gcaatttgtt      720
ccgcgctggc agtgaatttc gccagtcggt cggcaaaatg cgacagtgcc tcagggtcga      780
ccgtgtaacg gcggctcatg attccggatc                                       810
```

<210> SEQ ID NO 133
<211> LENGTH: 872
<212> TYPE: DNA
<213> ORGANISM: Mycobacterium avium
<400> SEQUENCE: 133

```
accaacccga tgcgccgaca ccacccaacg acgccgccaa ggccctgcaa gtgctgaaat       60
ctctgccgtc gttcgaggac acccaagctc aggtccaggc cgccatgaac gaaatcactg      120
cggcagcagg caaagtggtc ccctcggtta cgtgggaaac accgcacgag ggatcaggct      180
taggctgcga aaaaccgtat gaacaaacgg acgggcgagg ctacttcctg ccggatcaag      240
ttgccgccaa cgtgtcggtc tccgagcagc agtgggcaac aatccaagag gccgccaaac      300
aggccgcggc caagatcgac gccactgaaa tccaggtgat gcagaacaac cccggaaacc      360
acgacgtcgg cttctacggc cccaccggca tcttcatcaa agtgggttac cggggaaacc      420
```

-continued

```
tcgttgtgtc gggctacacg ggctgccgac taccgcgcga caagaaatag atcgcgcacg    480
agcacgactc ccgagtaggg attcggcgag cgtctctcac cgcgatctga cgaaacacgt    540
tgtggcccaa ggctgagcgc cgaccaatcg ctatgaattc ctgaccctct cgacccttcg    600
gaacacacgt tgagctgacc acgaattgcg ttgcccccag cagatttaaa actcatcgcc    660
gcaggttagg gacagtttcc atccggatca taacctcgcg ggcagtcggt agtttctccc    720
gataacgatc ttttccccgc cgtcgccatc cggttcaagc tcagactctt tggaatcgac    780
ccggctagcg tccagcctga atcagttgcg aaacgagtaa gtcataccgg aatggtgcca    840
ctcggatcgc atggctgagt accgaattcg ct                                  872
```

<210> SEQ ID NO 134
<211> LENGTH: 933
<212> TYPE: DNA
<213> ORGANISM: Mycobacterium avium

<400> SEQUENCE: 134

```
gcgatgttgc gttcccagcc gagctcggcg ctggccccga actccccgcc gtgcagcaac     60
accaccgggt cgccctcgcc cgcctcaagg tagctggtga ccaggccatc gaccgacatc    120
gttttgcgat gaatctccat cgcccgcctt ctctatttga tcgcgatcgg gttcaccggc    180
gaacccactg cccccacaaa cctcaacggc ggtgcgacaa gctggaattc gtagacgccg    240
tcggccgcgc aatcggccgc cagcgcgctg aggtcccagt actcgccgag catcagcccc    300
atgtcgcgca gggtcagcag gtggaagggc aaaaacaccc cgtcgacgcc ggacaccggg    360
tcttcgacct gcaggttgtc cgaggcgacc gcggcgacct cgtggtcatg cagccactgg    420
gcgcatcgcc agtccagccc ggaatacggt tcggtcttgt tccctgtttc caaatatctt    480
gtccaccaac cggtccggat gagcaggatg tcgccgcgct cgatcgtcac gccctgggcg    540
cgcacgacgt catccaattc ctctggggtg atcgggtttc cgtgctccaa gaagacctcc    600
gcgccgcgat ggcgcaccag atccagcagc accccgcgcg acgtgatgcc cttgccgtcc    660
accttctcga tgcccaagcg gcgggcgccc aggctggtca ccgagccggc ggggacgccg    720
ttgtagagca ggtcgtcgta gtagacgtgc gacagcgcat cccattgggt ggccgcctgc    780
agcggcatga tgatcatgtc gtcgttgaac cggaacaggt tgtcgacgaa gtaggggccc    840
atctgcgccg ccgtcgggtt gcggtcccag ccgggtccgt actgggccag cgtggcggcg    900
tcgccgccgt ccacggtcat cacgtggatc ggg                                 933
```

<210> SEQ ID NO 135
<211> LENGTH: 630
<212> TYPE: DNA
<213> ORGANISM: Mycobacterium avium

<400> SEQUENCE: 135

```
cggtcggcgt agccggccat cgcttcgtcg accgagttgt cgaccaccta gatgaggtgg     60
tgcagacctc gctcgccggt ggagccgatg tacatgccgg ggcgtttgcg gaccgcctcc    120
agcccttcca ggacggtgat cgctgaagca ccgtattcgt cttgcgcctt cttcttctgg    180
gcagccacgg tcgggaagct ctccttgggg tttcatgcgg gcggttcctg atcaccgcaa    240
caatcgcatc ctgccagtct accgtgacga ccggtccgca ccgattttct gggcgcgttt    300
ctacccagct aaccgcgccg tgcgcttatt ttcttcgttt gtgccgcgtc ccgacgtgcg    360
tcaaggagat acgcgtcgtc ctggcggctt tcagcgccct gttgaggaag gccccggtgg    420
```

```
ggatggggcc gggctaacga ccgggcctaa ccataggtgt cgcgcggccc gcgcccggcg    480
atgtgccgcg ggccttttgcg ccaggacggc gcagccggac cggtgatctt cagcgaggtc    540
actacgccgt tgccgaccgc ggcggcaatc ttggccaaca gttgcgcctg catcatccgc    600
aactgggtgg cccaggccgt cgactcggcg                                      630
```

<210> SEQ ID NO 136
<211> LENGTH: 1085
<212> TYPE: DNA
<213> ORGANISM: Mycobacterium avium

<400> SEQUENCE: 136

```
gagcggtccg ggtcagtgga catttttcag tcgagacgac aacggtcagc agcgaaccag     60
tacgttcgga gaaggcgaat tggtccgcag gtacgccaag gcgtcctgac gcccgggcgc    120
ttcaagccga tcagcgccgt tgatttgtgg atccgccggc gtcgggccga tcggaaaacg    180
tcgggtactc gacgggtttc gcggaggttt ccccgacgc gacatacttc ggctcctcgg    240
ggtgggaaaa caggttcgac tggtccatgg ttgtccttcc ggatgaagag ttcggccgat    300
acgcatcgct gcttggcgtc ggacgacgat cgaatcgcac ggcgctctga ttcgtggttc    360
gtcggcgatt cgcggtgacc gtaagaatgc ggttccactc cactctacag gcagcccgag    420
ccgcgcctgg cgcgtcgggt cagacggagc ccgggcgtgg ccgcagtcca ggtgcacagc    480
taatgaatcg gcaagtgagg caactatttt caatatatgg tcggtctcat gctaccctga    540
acccgcacgg atgtgattgg tacatccgca tttgatgaga gaagtaagta aatggcacag    600
ggaactgtga aatggttcaa cggtgaaaag ggcttcggct tcatcacccc tgacgacggc    660
acgaaggacc tcttcgtcca ctactccgag atccagggaa gcggctatcg ctcgctcgac    720
gagaaccagc gtgttcagtt cgacgttgag cagggagcca agggacccca ggcggtagga    780
gtcagcaccg tctgagaacg tcacaaacgt cacggtgggg ctggtgcgat tgacttcgca    840
ccagccccac tggttttttcc gacctctgaa cggtcggtgg cgacaacacc cggcggctga    900
ccccggcgcg gccgaccaac cgggataatg accgcatgcg tctcgcgtgg gtgctgcgac    960
tgacgattgc ggcgtcgttg gtcgcggcgg cgggacgcg taccgccgag gccagcccgg   1020
atgtcccgcc ggtcagcgag gccgcgaaag cggccggctt cgtggacatc cgcagcgtca   1080
ttccc                                                              1085
```

<210> SEQ ID NO 137
<211> LENGTH: 18
<212> TYPE: DNA
<213> ORGANISM: Artificial sequence
<220> FEATURE:
<223> OTHER INFORMATION: oligonucleotide primer

<400> SEQUENCE: 137

```
agggatatgc gagcgtca                                                   18
```

<210> SEQ ID NO 138
<211> LENGTH: 19
<212> TYPE: DNA
<213> ORGANISM: Artificial sequence
<220> FEATURE:
<223> OTHER INFORMATION: oligonucleotide primer

<400> SEQUENCE: 138

```
agttcctcgg tcaaccatt                                                  19
```

```
<210> SEQ ID NO 139
<211> LENGTH: 20
<212> TYPE: DNA
<213> ORGANISM: Artificial sequence
<220> FEATURE:
<223> OTHER INFORMATION: oligonucleotide primer

<400> SEQUENCE: 139
tactacttcc cctcgctgga                                              20

<210> SEQ ID NO 140
<211> LENGTH: 20
<212> TYPE: DNA
<213> ORGANISM: Artificial sequence
<220> FEATURE:
<223> OTHER INFORMATION: oligonucleotide primer

<400> SEQUENCE: 140
agtgccatga actccgtcat                                              20

<210> SEQ ID NO 141
<211> LENGTH: 19
<212> TYPE: DNA
<213> ORGANISM: Artificial sequence
<220> FEATURE:
<223> OTHER INFORMATION: oligonucleotide primer

<400> SEQUENCE: 141
atgccgtggt gctgttgat                                               19

<210> SEQ ID NO 142
<211> LENGTH: 20
<212> TYPE: DNA
<213> ORGANISM: Artificial sequence
<220> FEATURE:
<223> OTHER INFORMATION: oligonucleotide primer

<400> SEQUENCE: 142
agtcggagcc ttcttactgc                                              20

<210> SEQ ID NO 143
<211> LENGTH: 20
<212> TYPE: DNA
<213> ORGANISM: Artificial sequencel
<220> FEATURE:
<223> OTHER INFORMATION: oligonucleotide primer

<400> SEQUENCE: 143
gcagtaagaa ggctccgact                                              20

<210> SEQ ID NO 144
<211> LENGTH: 18
<212> TYPE: DNA
<213> ORGANISM: Artificial sequence
<220> FEATURE:
<223> OTHER INFORMATION: oligonucleotide primer

<400> SEQUENCE: 144
tactaccgcc acgcgact                                                18

<210> SEQ ID NO 145
<211> LENGTH: 20
<212> TYPE: DNA
<213> ORGANISM: Artificial sequence
<220> FEATURE:
<223> OTHER INFORMATION: oligonucleotide primer
```

```
<400> SEQUENCE: 145
gaaaaccctc gtccaccata                                              20

<210> SEQ ID NO 146
<211> LENGTH: 18
<212> TYPE: DNA
<213> ORGANISM: Artificial sequence
<220> FEATURE:
<223> OTHER INFORMATION: oligonucleotide primer

<400> SEQUENCE: 146
acgcttcaga ccgtgatg                                                18

<210> SEQ ID NO 147
<211> LENGTH: 20
<212> TYPE: DNA
<213> ORGANISM: Artificial sequence
<220> FEATURE:
<223> OTHER INFORMATION: oligonucleotide primer

<400> SEQUENCE: 147
ggcgtgtatt ccagatccat                                              20

<210> SEQ ID NO 148
<211> LENGTH: 20
<212> TYPE: DNA
<213> ORGANISM: Artificial sequence
<220> FEATURE:
<223> OTHER INFORMATION: oligonucleotide primer

<400> SEQUENCE: 148
cggtgaacat tcttgtgtgg                                              20

<210> SEQ ID NO 149
<211> LENGTH: 18
<212> TYPE: DNA
<213> ORGANISM: Artificial sequence
<220> FEATURE:
<223> OTHER INFORMATION: oligonucleotide primer

<400> SEQUENCE: 149
accgaaggcg aagtggtt                                                18

<210> SEQ ID NO 150
<211> LENGTH: 21
<212> TYPE: DNA
<213> ORGANISM: Artificial sequence
<220> FEATURE:
<223> OTHER INFORMATION: oligonucleotide primer

<400> SEQUENCE: 150
ttctctcatt tgctcgtagg g                                            21

<210> SEQ ID NO 151
<211> LENGTH: 20
<212> TYPE: DNA
<213> ORGANISM: Artificial sequence
<220> FEATURE:
<223> OTHER INFORMATION: oligonucleotide primer

<400> SEQUENCE: 151
ccagatgcgt agcgactgta                                              20

<210> SEQ ID NO 152
<211> LENGTH: 20
```

```
<212> TYPE: DNA
<213> ORGANISM: Artificial sequence
<220> FEATURE:
<223> OTHER INFORMATION: oligonucleotide primer

<400> SEQUENCE: 152
cgacaaacaa atgcgagaag                                                20

<210> SEQ ID NO 153
<211> LENGTH: 19
<212> TYPE: DNA
<213> ORGANISM: Artificial sequence
<220> FEATURE:
<223> OTHER INFORMATION: oligonucleotide primer

<400> SEQUENCE: 153
gggccacacc gtcatagtt                                                 19

<210> SEQ ID NO 154
<211> LENGTH: 20
<212> TYPE: DNA
<213> ORGANISM: Artificial sequence
<220> FEATURE:
<223> OTHER INFORMATION: oligonucleotide primer

<400> SEQUENCE: 154
ccaccaaaga tgggtagcag                                                20

<210> SEQ ID NO 155
<211> LENGTH: 18
<212> TYPE: DNA
<213> ORGANISM: Artificial sequence
<220> FEATURE:
<223> OTHER INFORMATION: oligonucleotide primer

<400> SEQUENCE: 155
gtgcgccctc tccacatt                                                  18

<210> SEQ ID NO 156
<211> LENGTH: 18
<212> TYPE: DNA
<213> ORGANISM: Artificial sequence
<220> FEATURE:
<223> OTHER INFORMATION: oligonucleotide primer

<400> SEQUENCE: 156
ccgaactcca cggttcct                                                  18

<210> SEQ ID NO 157
<211> LENGTH: 18
<212> TYPE: DNA
<213> ORGANISM: Artificial sequence
<220> FEATURE:
<223> OTHER INFORMATION: oligonucleotide primer

<400> SEQUENCE: 157
gctgccggaa cacaacct                                                  18

<210> SEQ ID NO 158
<211> LENGTH: 20
<212> TYPE: DNA
<213> ORGANISM: Artificial sequence
<220> FEATURE:
<223> OTHER INFORMATION: oligonucleotide primer

<400> SEQUENCE: 158
```

-continued ggcatctgaa aactccacct                     20

<210> SEQ ID NO 159
<211> LENGTH: 20
<212> TYPE: DNA
<213> ORGANISM: Artificial sequence
<220> FEATURE:
<223> OTHER INFORMATION: oligonucleotide primer

<400> SEQUENCE: 159
agtgggcaac aatccaagag                     20

<210> SEQ ID NO 160
<211> LENGTH: 18
<212> TYPE: DNA
<213> ORGANISM: Artificial sequence
<220> FEATURE:
<223> OTHER INFORMATION: oligonucleotide primer

<400> SEQUENCE: 160
cccgacacaa cgaggttt                       18

<210> SEQ ID NO 161
<211> LENGTH: 20
<212> TYPE: DNA
<213> ORGANISM: Artificial sequence
<220> FEATURE:
<223> OTHER INFORMATION: oligonucleotide primer

<400> SEQUENCE: 161
acacacgttg agctgaccac                     20

<210> SEQ ID NO 162
<211> LENGTH: 19
<212> TYPE: DNA
<213> ORGANISM: Artificial sequence
<220> FEATURE:
<223> OTHER INFORMATION: oligonucleotide primer

<400> SEQUENCE: 162
tctgagcttg aaccggatg                      19

<210> SEQ ID NO 163
<211> LENGTH: 18
<212> TYPE: DNA
<213> ORGANISM: Artificial sequence
<220> FEATURE:
<223> OTHER INFORMATION: oligonucleotide primer

<400> SEQUENCE: 163
aatctctgcc gtcgttcg                       18

<210> SEQ ID NO 164
<211> LENGTH: 19
<212> TYPE: DNA
<213> ORGANISM: Artificial sequence
<220> FEATURE:
<223> OTHER INFORMATION: oligonucleotide primer

<400> SEQUENCE: 164
gcccgtccgt ttgttcata                      19

<210> SEQ ID NO 165
<211> LENGTH: 19
<212> TYPE: DNA
<213> ORGANISM: Artificial sequence

```
<220> FEATURE:
<223> OTHER INFORMATION: oligonucleotide primer

<400> SEQUENCE: 165
atcgaccgac atcgttttg                                              19

<210> SEQ ID NO 166
<211> LENGTH: 18
<212> TYPE: DNA
<213> ORGANISM: Artificial sequence
<220> FEATURE:
<223> OTHER INFORMATION: oligonucleotide primer

<400> SEQUENCE: 166
gacatggggc tgatgctc                                               18

<210> SEQ ID NO 167
<211> LENGTH: 19
<212> TYPE: DNA
<213> ORGANISM: Artificial sequence
<220> FEATURE:
<223> OTHER INFORMATION: oligonucleotide primer

<400> SEQUENCE: 167
gtggaagggc aaaaacacc                                              19

<210> SEQ ID NO 168
<211> LENGTH: 20
<212> TYPE: DNA
<213> ORGANISM: Artificial sequence
<220> FEATURE:
<223> OTHER INFORMATION: oligonucleotide primer

<400> SEQUENCE: 168
tggaaacagg gaacaagacc                                             20

<210> SEQ ID NO 169
<211> LENGTH: 20
<212> TYPE: DNA
<213> ORGANISM: Artificial sequence
<220> FEATURE:
<223> OTHER INFORMATION: oligonucleotide primer

<400> SEQUENCE: 169
gtttccgtgc tccaagaaga                                             20

<210> SEQ ID NO 170
<211> LENGTH: 20
<212> TYPE: DNA
<213> ORGANISM: Artificial sequence
<220> FEATURE:
<223> OTHER INFORMATION: oligonucleotide primer

<400> SEQUENCE: 170
acgacgacct gctctacaac                                             20

<210> SEQ ID NO 171
<211> LENGTH: 18
<212> TYPE: DNA
<213> ORGANISM: Artificial sequence
<220> FEATURE:
<223> OTHER INFORMATION: oligonucleotide primer

<400> SEQUENCE: 171
caccgcaaca atcgcatc                                               18
```

```
<210> SEQ ID NO 172
<211> LENGTH: 21
<212> TYPE: DNA
<213> ORGANISM: Artificial sequence
<220> FEATURE:
<223> OTHER INFORMATION: oligonucleotide primer

<400> SEQUENCE: 172
cggcacaaac gaagaaaata a                                           21

<210> SEQ ID NO 173
<211> LENGTH: 19
<212> TYPE: DNA
<213> ORGANISM: Artificial sequence
<220> FEATURE:
<223> OTHER INFORMATION: oligonucleotide primer

<400> SEQUENCE: 173
cgggcctaac cataggtgt                                              19

<210> SEQ ID NO 174
<211> LENGTH: 20
<212> TYPE: DNA
<213> ORGANISM: Artificial sequence
<220> FEATURE:
<223> OTHER INFORMATION: oligonucleotide primer

<400> SEQUENCE: 174
cgtagtgacc tcgctgaaga                                             20

<210> SEQ ID NO 175
<211> LENGTH: 20
<212> TYPE: DNA
<213> ORGANISM: Artificial sequence
<220> FEATURE:
<223> OTHER INFORMATION: oligonucleotide primer

<400> SEQUENCE: 175
cactggtttt tccgacctct                                             20

<210> SEQ ID NO 176
<211> LENGTH: 18
<212> TYPE: DNA
<213> ORGANISM: Artificial sequence
<220> FEATURE:
<223> OTHER INFORMATION: oligonucleotide primer

<400> SEQUENCE: 176
caatcgtcag tcgcagca                                               18

<210> SEQ ID NO 177
<211> LENGTH: 18
<212> TYPE: DNA
<213> ORGANISM: Artificial sequence
<220> FEATURE:
<223> OTHER INFORMATION: oligonucleotide primer

<400> SEQUENCE: 177
cgccgttgat ttgtggat                                               18

<210> SEQ ID NO 178
<211> LENGTH: 19
<212> TYPE: DNA
<213> ORGANISM: Artificial sequence
<220> FEATURE:
<223> OTHER INFORMATION: oligonucleotide primer
```

<400> SEQUENCE: 178
ccgaggagcc gaagtatgt                                                  19

<210> SEQ ID NO 179
<211> LENGTH: 19
<212> TYPE: DNA
<213> ORGANISM: Artificial sequence
<220> FEATURE:
<223> OTHER INFORMATION: oligonucleotide primer

<400> SEQUENCE: 179
cgcacggatg tgattggta                                                  19

<210> SEQ ID NO 180
<211> LENGTH: 20
<212> TYPE: DNA
<213> ORGANISM: Artificial sequence
<220> FEATURE:
<223> OTHER INFORMATION: oligonucleotide primer

<400> SEQUENCE: 180
cggagtagtg gacgaagagg                                                 20

<210> SEQ ID NO 181
<211> LENGTH: 18
<212> TYPE: DNA
<213> ORGANISM: Artificial sequence
<220> FEATURE:
<223> OTHER INFORMATION: oligonucleotide primer

<400> SEQUENCE: 181
ggctatcgct cgctcgac                                                   18

<210> SEQ ID NO 182
<211> LENGTH: 21
<212> TYPE: DNA
<213> ORGANISM: Artificial sequence
<220> FEATURE:
<223> OTHER INFORMATION: oligonucleotide primer

<400> SEQUENCE: 182
tgacgtttgt gacgttctca g                                               21

<210> SEQ ID NO 183
<211> LENGTH: 154
<212> TYPE: DNA
<213> ORGANISM: Artificial sequence
<220> FEATURE:
<223> OTHER INFORMATION: oligonucleotide probe

<400> SEQUENCE: 183
agggatatgc gagcgtcacg tatcgcgcct tggccgcgaa ggctggcgtg acgccaagcc     60
tcgtgcagta ctacttcccc tcgctggatg acatcttcgt cgccgccatt cgccgctact    120
ccgagcgcaa cctgcaatgg ttgaccgagg aact                                154

<210> SEQ ID NO 184
<211> LENGTH: 176
<212> TYPE: DNA
<213> ORGANISM: Artificial sequence
<220> FEATURE:
<223> OTHER INFORMATION: oligonucleotide probe

<400> SEQUENCE: 184

```
tactacttcc cctcgctgga tgacatcttc gtcgccgcca ttcgccgcta ctccgagcgc    60
aacctgcaat ggttgaccga ggaacttcag cggcgagccg acgacccact tcatgcgctg   120
tgggagagca gctggcacga gtcgacgagt gcgctgatga cggagttcat ggcact       176
```

```
<210> SEQ ID NO 185
<211> LENGTH: 164
<212> TYPE: DNA
<213> ORGANISM: Artificial sequence
<220> FEATURE:
<223> OTHER INFORMATION: oligonucleotide probe

<400> SEQUENCE: 185
```

```
atgccgtggt gctgttgatc aacggcgttc cgaagctcct tgggttggag gaaagcgtgg    60
gcgtcgatac cgcccacgcc gaattgatcg ccgcgtgcga gcgctttctg gacgccgtcg   120
aacctcgagc caagcctcgc cgtcgcagta agaaggctcc gact                    164
```

```
<210> SEQ ID NO 186
<211> LENGTH: 157
<212> TYPE: DNA
<213> ORGANISM: Artificial sequence
<220> FEATURE:
<223> OTHER INFORMATION: oligonucleotide probe

<400> SEQUENCE: 186
```

```
gcagtaagaa ggctccgact cgccgacgct gactcgtcgc ggcgggcgct tcacgggagg    60
ccttgtgacc gcgctgtacg tccgtataga ctggacgatc gtatagcagg tgcacggcgg   120
gtggaaggcg agcattgtga gtcgcgtggc ggtagta                            157
```

```
<210> SEQ ID NO 187
<211> LENGTH: 152
<212> TYPE: DNA
<213> ORGANISM: Artificial sequence
<220> FEATURE:
<223> OTHER INFORMATION: oligonucleotide probe

<400> SEQUENCE: 187
```

```
gaaaaccctc gtccaccata ttctttgggc catccgacac ccagcaggtt ggccgccgcc    60
agggcgcgga cgcattcgcg caccgcggga ccgccgtcca tctgctcgct gaccgcggcg   120
acgcgttcgg gcgtcatcac ggtctgaagc gt                                 152
```

```
<210> SEQ ID NO 188
<211> LENGTH: 193
<212> TYPE: DNA
<213> ORGANISM: Artificial sequence
<220> FEATURE:
<223> OTHER INFORMATION: oligonucleotide probe

<400> SEQUENCE: 188
```

```
ggcgtgtatt ccagatccat cggctcaggc ccccattcgc accggcatgc gtttcacccc    60
gggcaccatg gtggcccgca tccggtccac ctcgcccacc agctcgatgc ggggataccg   120
gcgcagcagc tcctcgaaga acaccgtcgc ctccagtcgc gccaattgtg cgcccacaca   180
agaatgttca ccg                                                      193
```

```
<210> SEQ ID NO 189
<211> LENGTH: 178
<212> TYPE: DNA
<213> ORGANISM: Artificial sequence
<220> FEATURE:
<223> OTHER INFORMATION: oligonucleotide probe
```

-continued

<400> SEQUENCE: 189

| accgaaggcg aagtggttcg aacgaaacgg gtgtcaccca gtacggcata aaatacaacc | 60 |
| aagtgatctc gatcgccgga gcgaacggaa gggtcataga tgtgacgttc gcctggatac | 120 |
| gcggaaacga cggtgtagtg cgcttggtga cggcgatccc tacgagcaaa tgagagaa | 178 |

<210> SEQ ID NO 190
<211> LENGTH: 139
<212> TYPE: DNA
<213> ORGANISM: Artificial sequence
<220> FEATURE:
<223> OTHER INFORMATION: oligonucleotide probe

<400> SEQUENCE: 190

| ccagatgcgt agcgactgta gttgcggccc gattcagggc cacatggccg tattgtgttg | 60 |
| ggccacaccg tcatagttgc ggtgcgccct ctccacattg gtgcgcaatt cggtgagcgc | 120 |
| ttctcgcatt tgtttgtcg | 139 |

<210> SEQ ID NO 191
<211> LENGTH: 101
<212> TYPE: DNA
<213> ORGANISM: Artificial sequence
<220> FEATURE:
<223> OTHER INFORMATION: oligonucleotide probe

<400> SEQUENCE: 191

| gggccacacc gtcatagttg cggtgcgccc tctccacatt ggtgcgcaat tcggtgagcg | 60 |
| cttctcgcat ttgtttgtcg gctgctaccc atctttggtg g | 101 |

<210> SEQ ID NO 192
<211> LENGTH: 131
<212> TYPE: DNA
<213> ORGANISM: Artificial sequence
<220> FEATURE:
<223> OTHER INFORMATION: oligonucleotide probe

<400> SEQUENCE: 192

| gtgcgccctc tccacattgg tgcgcaattc ggtgagcgct tctcgcattt gtttgtcggc | 60 |
| tgctacccat ctttggtggt actcgcgctc ggcgtctgcg ccgcgaccca gccaggaacc | 120 |
| gtggagttcg g | 131 |

<210> SEQ ID NO 193
<211> LENGTH: 112
<212> TYPE: DNA
<213> ORGANISM: Artificial sequence
<220> FEATURE:
<223> OTHER INFORMATION: oligonucleotide probe

<400> SEQUENCE: 193

| gctgccggaa cacaacctgc ctgccggttc acgcgggact atcgtcatgg attacacgaa | 60 |
| ggattcggat agcactctcc cgtccgcgta cgaggtggag ttttcagatg cc | 112 |

<210> SEQ ID NO 194
<211> LENGTH: 163
<212> TYPE: DNA
<213> ORGANISM: Artificial sequence
<220> FEATURE:
<223> OTHER INFORMATION: oligonucleotide probe

<400> SEQUENCE: 194

```
agtgggcaac aatccaagag gccgccaaac aggccgcggc caagatcgac gccactgaaa      60
tccaggtgat gcagaacaac cccggaaacc acgacgtcgg cttctacggc cccaccggca     120
tcttcatcaa agtgggttac cggggaaacc tcgttgtgtc ggg                       163

<210> SEQ ID NO 195
<211> LENGTH: 163
<212> TYPE: DNA
<213> ORGANISM: Artificial sequence
<220> FEATURE:
<223> OTHER INFORMATION: oligonucleotide probe

<400> SEQUENCE: 195
acacacgttg agctgaccac gaattgcgtt gcccccagca gatttaaaac tcatcgccgc      60
aggttaggga cagtttccat ccggatcata acctcgcggg cagtcggtag tttctcccga    120
taacgatctt ttccccgccg tcgccatccg gttcaagctc aga                       163

<210> SEQ ID NO 196
<211> LENGTH: 159
<212> TYPE: DNA
<213> ORGANISM: Artificial sequence
<220> FEATURE:
<223> OTHER INFORMATION: oligonucleotide probe

<400> SEQUENCE: 196
aatctctgcc gtcgttcgag gacacccaag ctcaggtcca ggccgccatg aacgaaatca      60
ctgcggcagc aggcaaagtg gtcccctcgg ttacgtggga acaccgcac gagggatcag     120 gcttaggctg cgaaaaaccg tatgaacaaa cggacgggc                            159

<210> SEQ ID NO 197
<211> LENGTH: 198
<212> TYPE: DNA
<213> ORGANISM: Artificial sequence
<220> FEATURE:
<223> OTHER INFORMATION: oligonucleotide probe

<400> SEQUENCE: 197
atcgaccgac atcgtttttgc gatgaatctc catcgcccgc cttctctatt tgatcgcgat     60
cgggttcacc ggcgaaccca ctgcccccac aaacctcaac ggcggtgcga caagctggaa    120
ttcgtagacg ccgtcggccg cgcaatcggc cgccagcgcg ctgaggtccc agtactcgcc    180
gagcatcagc cccatgtc                                                   198

<210> SEQ ID NO 198
<211> LENGTH: 152
<212> TYPE: DNA
<213> ORGANISM: Artificial sequence
<220> FEATURE:
<223> OTHER INFORMATION: oligonucleotide probe

<400> SEQUENCE: 198
gtggaagggc aaaaacaccc cgtcgacgcc ggacaccggg tcttcgacct gcaggttgtc      60
cgaggcgacc gcggcgacct cgtggtcatg cagccactgg gcgcatcgcc agtccagccc    120
ggaatacggt tcggtcttgt tccctgtttc ca                                   152

<210> SEQ ID NO 199
<211> LENGTH: 164
<212> TYPE: DNA
<213> ORGANISM: Artificial sequence
<220> FEATURE:
<223> OTHER INFORMATION: oligonucleotide probe
```

<400> SEQUENCE: 199
gtttccgtgc tccaagaaga cctccgcgcc gcgatggcgc accagatcca gcagcacccc    60
gcgcgacgtg atgcccttgc cgtccacctt ctcgatgccc aagcggcggg cgcccaggct   120
ggtcaccgag ccggcgggga cgccgttgta gagcaggtcg tcgt                    164

<210> SEQ ID NO 200
<211> LENGTH: 114
<212> TYPE: DNA
<213> ORGANISM: Artificial sequence
<220> FEATURE:
<223> OTHER INFORMATION: oligonucleotide probe

<400> SEQUENCE: 200
caccgcaaca atcgcatcct gccagtctac cgtgacgacc ggtccgcacc gattttctgg    60
gcgcgtttct acccagctaa ccgcgccgtg cgcttatttt cttcgtttgt gccg         114

<210> SEQ ID NO 201
<211> LENGTH: 105
<212> TYPE: DNA
<213> ORGANISM: Artificial sequence
<220> FEATURE:
<223> OTHER INFORMATION: oligonucleotide probe

<400> SEQUENCE: 201
cgggcctaac cataggtgtc gcgcggcccg cgccggcga tgtgccgcgg gcctttgcgc    60
caggacggcg cagccggacc ggtgatcttc agcgaggtca ctacg                  105

<210> SEQ ID NO 202
<211> LENGTH: 122
<212> TYPE: DNA
<213> ORGANISM: Artificial sequence
<220> FEATURE:
<223> OTHER INFORMATION: oligonucleotide probe

<400> SEQUENCE: 202
cactggtttt tccgacctct gaacggtcgg tggcgacaac accggcggc tgaccccggc    60 gcggccgacc aaccgggata atgaccgcat gcgtctcgcg tgggtgctgc gactgacgat  120
tg                                                                 122

<210> SEQ ID NO 203
<211> LENGTH: 106
<212> TYPE: DNA
<213> ORGANISM: Artificial sequence
<220> FEATURE:
<223> OTHER INFORMATION: oligonucleotide probe

<400> SEQUENCE: 203
cgccgttgat ttgtggatcc gccggcgtcg ggccgatcgg aaaacgtcgg gtactcgacg    60
ggtttcgcgg aggtttcccc cgacgcgaca tacttcggct cctcgg                 106

<210> SEQ ID NO 204
<211> LENGTH: 145
<212> TYPE: DNA
<213> ORGANISM: Artificial sequence
<220> FEATURE:
<223> OTHER INFORMATION: oligonucleotide probe

<400> SEQUENCE: 204
cgcacggatg tgattggtac atccgcattt gatgagagaa gtaagtaaat ggcacaggga    60

```
actgtgaaat ggttcaacgg tgaaaagggc ttcggcttca tcaccoctga cgacggcacg      120 aaggacctct tcgtccacta ctccg                                            145

<210> SEQ ID NO 205
<211> LENGTH: 110
<212> TYPE: DNA
<213> ORGANISM: Artificial sequence
<220> FEATURE:
<223> OTHER INFORMATION: oligonucleotide probe

<400> SEQUENCE: 205
ggctatcgct cgctcgacga gaaccagcgt gttcagttcg acgttgagca gggagccaag       60 ggacccagg cggtaggagt cagcaccgtc tgagaacgtc acaaacgtca                  110
```